US011524981B2

(12) United States Patent
Jung et al.

(10) Patent No.: US 11,524,981 B2
(45) Date of Patent: Dec. 13, 2022

(54) L-TRYPTOPHAN-EXPORTING PROTEIN VARIANT AND METHOD FOR PRODUCING L-TRYPTOPHAN USING THE SAME

(71) Applicant: CJ CHEILJEDANG CORPORATION, Seoul (KR)

(72) Inventors: Moo Young Jung, Seoul (KR); Hyun Ah Kim, Seoul (KR); Chang Il Seo, Seoul (KR); Imsang Lee, Seoul (KR); Ji-won Kim, Seoul (KR); Tae Yeon Kim, Seoul (KR); Sung Kwang Son, Seoul (KR); Ki Yong Cheong, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 17/268,691

(22) PCT Filed: Mar. 20, 2020

(86) PCT No.: PCT/KR2020/003855

§ 371 (c)(1),
(2) Date: Feb. 16, 2021

(87) PCT Pub. No.: WO2020/204427

PCT Pub. Date: Oct. 8, 2020

(65) Prior Publication Data

US 2022/0009973 A1 Jan. 13, 2022

(30) Foreign Application Priority Data

Apr. 5, 2019 (KR) ........................ 10-2019-0040397

(51) Int. Cl.

| | |
|---|---|
| ***C12P 13/22*** | (2006.01) |
| ***C12N 1/21*** | (2006.01) |
| ***C12N 15/74*** | (2006.01) |
| ***C12N 15/77*** | (2006.01) |
| ***C07K 14/195*** | (2006.01) |
| *C12R 1/15* | (2006.01) |
| *C12R 1/19* | (2006.01) |

(52) U.S. Cl.
CPC ............ *C07K 14/195* (2013.01); *C12P 13/22* (2013.01); *C12R 2001/15* (2021.05); *C12R 2001/19* (2021.05)

(58) Field of Classification Search
None
See application file for complete search history.

(56) References Cited

U.S. PATENT DOCUMENTS

2020/0063219 A1* 2/2020 Jung .................... C12P 13/227

FOREIGN PATENT DOCUMENTS

| | | | | |
|---|---|---|---|---|
| EP | 1013765 A1 | | 6/2000 | |
| EP | 1016710 A2 | | 7/2000 | |
| EP | 3561016 A1 | | 10/2019 | |
| KR | 10-1023925 B1 | | 3/2011 | |
| KR | 10-1142885 B1 | | 5/2012 | |
| KR | 10-2018-0089329 A | | 8/2018 | |
| KR | 101968317 B1 | * | 4/2019 | ............. C12P 13/22 |
| WO | 97/23597 A2 | | 7/1997 | |
| WO | WO-2019164348 A1 | * | 8/2019 | ........... C07K 14/195 |

OTHER PUBLICATIONS

GenBank Database Accession No. WP_128385807, Jan. 2019, 1 page (Year: 2019).*
Singh et al., Curr. Protein Pept. Sci. 18:1-11, 2017 (Year: 2017).*
Zhang et al., Structure 26:1474-1485, 2018 (Year: 2018).*
English translation of KR 101968317 B1, obtained from Google Patents on Mar. 21, 2022, 23 pages (Year: 2022).*
English translation of WO 2019/164348 A1 (obtained from Google Patents on Mar. 21, 2022, 23 pages (Year: 2022).*
Palego et al., J. Amino Acids 2016:8952520, 13 pages (Year: 2016).*
Doroshenko et al., "YddG from *Escherichia coli* promotes export of aromatic amino acids," FEMS Microbiol Lett 275: 312-318 (2007).
Zhang et al., "Rational engineering of multiple module pathways for the production of L-phenylalanine in Corynebacterium glutamicum," J Ind Microbiol Biotechnol. 42(5): 787-797 (2015).
NCBI, Accession No. WP_050478745 (2017).
Wang et al., "Genetic engineering of *Escherichia coli* to enhance production of L-tryptophan," Applied Microbiology and Biotechnology, 97: 7587-7596 (2013).
International Search Report issued in corresponding International Patent Application No. PCT/KR2020/003855 dated Jun. 19, 2020.

* cited by examiner

*Primary Examiner* — David Steadman
(74) *Attorney, Agent, or Firm* — Morgan, Lewis & Bockius LLP

(57) ABSTRACT

The present disclosure relates to a protein variant having a tryptophan-exporting activity, an L-tryptophan-producing microorganism expressing the protein variant, and a method for producing L-tryptophan using the microorganism.

10 Claims, 1 Drawing Sheet

Specification includes a Sequence Listing.

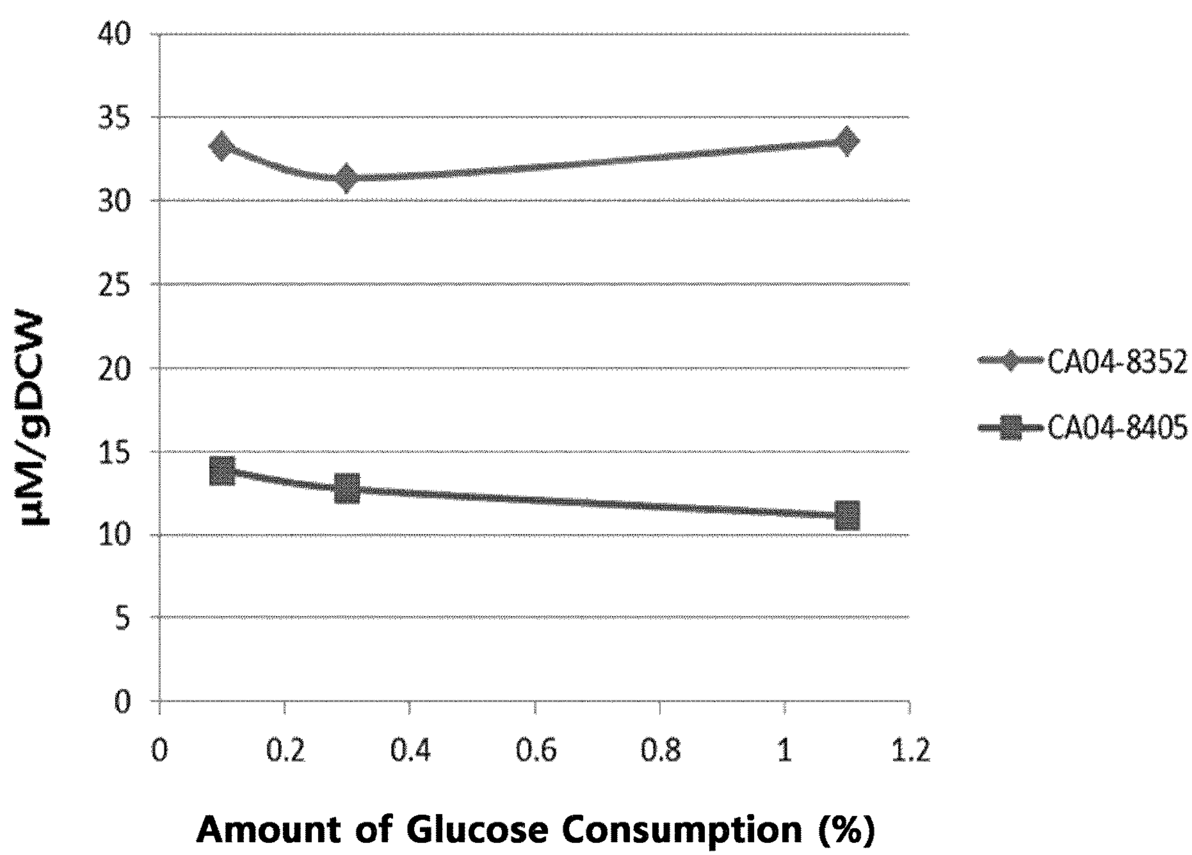
40
35
30
25
20
15
10
5
0
µM/gDCW
0
0.2
0.4
0.6
0.8
1
1.2
Amount of Glucose Consumption (%)
CA04-8352
CA04-8405

SEQUENCE LISTING

<160> NUMBER OF SEQ ID NOS: 147

<210> SEQ ID NO 1
<211> LENGTH: 307
<212> TYPE: PRT
<213> ORGANISM: Artificial Sequence
<220> FEATURE:
<223> OTHER INFORMATION: wex AA seq.

<400> SEQUENCE: 1

```
Met Asn Ser Lys Lys Ala Thr Leu Ile Gly Leu Thr Ala Val Val Leu
1               5                   10                  15

Trp Ser Ser Ile Val Gly Leu Ile Arg Gly Val Ser Glu His Leu Gly
            20                  25                  30

Ala Thr Gly Gly Ala Ala Met Met Tyr Ser Val Ala Ser Leu Phe Leu
        35                  40                  45

Leu Leu Ser Val Gly Phe Pro Lys Leu Gly Ser Phe Pro Lys Lys Tyr
    50                  55                  60

Leu Leu Trp Gly Ser Leu Leu Phe Val Ser Tyr Glu Leu Cys Leu Ser
65                  70                  75                  80

Leu Ser Ile Gly Tyr Ala Asn Thr Gly Arg Gln Ala Ile Glu Val Ser
                85                  90                  95

Met Val Asn Tyr Leu Trp Pro Ala Phe Thr Leu Ile Ala Ala Ile Ala
            100                 105                 110

Phe Asn Arg Gln Arg Ala Asn Trp Met Val Val Pro Gly Phe Ile Leu
        115                 120                 125

Ser Ile Ile Gly Ile Cys Trp Val Leu Gly Gly Asp Gln Gly Leu Asp
    130                 135                 140

Leu Ala Gly Met Leu Gly Asn Val Gln Asp Asn Pro Leu Ser Tyr Gly
145                 150                 155                 160

Leu Ala Phe Leu Gly Ala Val Ile Trp Ala Ala Tyr Cys Thr Val Thr
                165                 170                 175

Ala Arg Leu Ala Lys Gly Lys Asn Gly Val Thr Leu Phe Phe Ile Leu
            180                 185                 190

Val Ala Leu Thr Leu Trp Val Lys Phe Phe Phe Gly Asp His Arg Pro
        195                 200                 205

Met Ser Phe Ser Leu Pro Ala Ile Val Tyr Leu Leu Leu Ala Ala Ala
    210                 215                 220

Ala Met Gly Phe Gly Tyr Ala Ala Trp Asn Val Gly Ile Leu His Gly
225                 230                 235                 240

Asn Val Thr Val Leu Ala Gly Val Ser Tyr Phe Ile Pro Val Phe Ser
                245                 250                 255

Ala Ala Leu Ser Ala Met Val Leu His Ala Pro Leu Pro Arg Ser Phe
            260                 265                 270

Trp Val Gly Ala Ser Leu Val Cys Ala Gly Ser Ile Leu Cys Trp Leu
        275                 280                 285

Ala Thr Arg Ala Arg Arg Ala Ser Ala Ala Gln Glu Asp Ala Val Ala
    290                 295                 300

Asp Cys Leu
305
```

<210> SEQ ID NO 2
<211> LENGTH: 924
<212> TYPE: DNA
<213> ORGANISM: Artificial Sequence
<220> FEATURE:
<223> OTHER INFORMATION: wex NT seq.

<400> SEQUENCE: 2

```
atgaatagca agaaggccac gctgatcgga cttactgcag tggtcctctg gagttccatt      60
gtcggattga ttcgcggcgt cagcgaacat ctcggcgcta ccgggggcgc ggcgatgatg     120
tatagcgttg cctcgctgtt tctgctgttg tcggtcggtt tcccgaaact gggttccttt     180
ccgaaaaaat acctcttgtg gggcagcctg ctgtttgtgt cctacgaact ctgcctgtcg     240
ctctccatcg gttatgccaa tacaggcagg caagcaatcg aagtcagcat ggtcaactat     300
ctgtggccgg cattcacgct catcgccgcc attgcattca accggcagag agcgaactgg     360
atggtggtgc ccggattcat cctctcgatt atcggtatct gctgggtgct gggcggtgac     420
caggggctgg acctggcggg catgcttggc aacgtgcagg acaatccgct cagttatggg     480
ctggcttttt tgggcgccgt gatctgggcc gcctattgca ctgtgacggc ccgcctcgcg     540
aaggggaaga acggagtgac gctgttcttc attcttgtgg cattgacgct ctgggtgaag     600
tttttcttcg gcgatcaccg cccgatgtct ttcagcctgc cggcaattgt ctacctgctc     660
ctggcggcgg ccgcgatggg cttcggctat gcggcatgga atgtcgggat cttgcacggt     720
aacgtgaccg tgctggcggg cgtgtcgtac tttatcccgg ttttttcggc ggcgttgtcc     780
gcgatggtgt tgcatgcgcc gttgccgcga tcgttttggg tgggggcgtc gctggtatgc     840
gccggttcga tactgtgctg gctggcaacc agggccaggc gcgcttcggc cgcgcaagaa     900
gatgcggtgg cggactgttt gtag                                            924
```

<210> SEQ ID NO 3
<211> LENGTH: 35
<212> TYPE: DNA
<213> ORGANISM: Artificial Sequence
<220> FEATURE:
<223> OTHER INFORMATION: wex - 1

<400> SEQUENCE: 3

```
tagaggagac acaacatgaa tagcaagaag gccac                                 35
```

<210> SEQ ID NO 4
<211> LENGTH: 35
<212> TYPE: DNA
<213> ORGANISM: Artificial Sequence
<220> FEATURE:
<223> OTHER INFORMATION: wex - 2

<400> SEQUENCE: 4

```
ggctcttcct gtttagtcta caaacagtcc gccac                                 35
```

<210> SEQ ID NO 5
<211> LENGTH: 35
<212> TYPE: DNA
<213> ORGANISM: Artificial Sequence
<220> FEATURE:
<223> OTHER INFORMATION: PgapA(-wex) - 1

<400> SEQUENCE: 5

```
cccttccggt ttagtttgaa gccagtgtga gttgc                                 35
```

<210> SEQ ID NO 6
<211> LENGTH: 39
<212> TYPE: DNA
<213> ORGANISM: Artificial Sequence
<220> FEATURE:
<223> OTHER INFORMATION: PgapA(-wex) - 2

<400> SEQUENCE: 6
cttcttgcta ttcatgttgt gtctcctcta aagattgta 39

<210> SEQ ID NO 7
<211> LENGTH: 20
<212> TYPE: DNA
<213> ORGANISM: Artificial Sequence
<220> FEATURE:
<223> OTHER INFORMATION: Confirm_PgapA-wex - 1

<400> SEQUENCE: 7
cggattatgc caatgatgtg 20

<210> SEQ ID NO 8
<211> LENGTH: 20
<212> TYPE: DNA
<213> ORGANISM: Artificial Sequence
<220> FEATURE:
<223> OTHER INFORMATION: Confirm_PgapA-wex - 2

<400> SEQUENCE: 8
cacgatcacc aacattcagg 20

<210> SEQ ID NO 9
<211> LENGTH: 314
<212> TYPE: PRT
<213> ORGANISM: Artificial Sequence
<220> FEATURE:
<223> OTHER INFORMATION: Pst AA seq.

<400> SEQUENCE: 9

```
Met Lys Asn Gln Arg Lys Ala Thr Leu Ile Gly Leu Val Ala Ile Val
1               5                   10                  15

Leu Trp Ser Ser Ile Val Gly Leu Ile Arg Gly Val Ser Glu Ser Leu
            20                  25                  30

Gly Ala Thr Gly Gly Ala Val Met Met Tyr Ser Val Ala Ser Val Met
        35                  40                  45

Leu Leu Phe Thr Val Gly Phe Pro Arg Ile Arg Glu Phe Pro Arg Arg
    50                  55                  60

Tyr Leu Val Trp Gly Ser Leu Leu Phe Val Ser Tyr Glu Leu Cys Leu
65                  70                  75                  80

Ala Leu Ser Ile Gly Tyr Ala Asn Ser Ser Arg Gln Ala Ile Glu Val
                85                  90                  95

Gly Met Val Asn Tyr Leu Trp Pro Ala Phe Thr Ile Leu Ala Ala Ile
            100                 105                 110

Leu Phe Asn Arg Gln Gln Ala Asn Leu Leu Ile Val Pro Gly Phe Leu
        115                 120                 125

Ile Ala Ile Leu Gly Ile Cys Trp Val Leu Gly Gly Glu Gln Gly Leu
    130                 135                 140

Asp Leu Ser Gly Met Thr Ala Asn Ile Arg Asp Asn Pro Leu Ser Tyr
145                 150                 155                 160

Gly Leu Ala Phe Ala Gly Ala Val Ile Trp Ala Ala Tyr Cys Thr Val
                165                 170                 175

Thr Thr Arg Ile Ala Gly Gly Lys Asn Gly Val Thr Leu Phe Phe Met
            180                 185                 190

Leu Thr Ala Leu Ala Leu Trp Ala Lys Tyr Leu Ala Ile Gly Gly Glu
        195                 200                 205

Thr Met Glu Phe Ser Tyr His Ala Leu Ile Tyr Leu Val Leu Ala Ala
    210                 215                 220
```

```
Ser Ala Met Gly Phe Gly Tyr Ala Ala Trp Asn Val Gly Ile Leu His
225                 230                 235                 240

Gly Asn Val Thr Val Leu Ala Gly Ala Ser Tyr Phe Ile Pro Val Leu
                245                 250                 255

Ser Ala Ala Leu Ala Ala Val Leu Leu Arg Thr Pro Leu Ser Leu Ser
            260                 265                 270

Phe Trp Gln Gly Ala Ala Met Val Cys Ile Gly Ser Ile Leu Cys Trp
        275                 280                 285

Phe Ala Thr Arg Ala Lys Pro Pro Glu Ser Ala Gln Ser Gly Asp Gln
    290                 295                 300

Ala Ser Ala Thr Thr Pro Arg Arg Asn Gly
305                 310
```

<210> SEQ ID NO 10
<211> LENGTH: 945
<212> TYPE: DNA
<213> ORGANISM: Artificial Sequence
<220> FEATURE:
<223> OTHER INFORMATION: Pst NT seq.

<400> SEQUENCE: 10

```
atgaaaaacc agcgtaaagc gaccctcatc gggctcgttg caattgtctt gtggagctcg     60

atcgtcggcc tgatccgggg cgtcagcgag agcctcggcg cgaccggtgg tgccgtcatg    120

atgtacagcg tcgcatcggt aatgctgttg ttcacggtcg gctttccgcg gatacgggag    180

ttcccccgac gctatcttgt ctggggcagc ctgctgttcg tctcgtacga gctgtgcctt    240

gccctgtcca tcggctacgc caacagcagc cgacaggcca tcgaggtcgg catggtcaat    300

tacctgtggc cggccttcac gatcctggcg gcgatcctgt tcaacaggca gcaggccaac    360

ctgctcatcg ttcccggctt cctcatcgcg atcctcggga tctgctgggt gctcggcggg    420

gaacaggggc tggacctgtc cgggatgacg gcgaacatcc gcgacaatcc cctcagctac    480

gggctggcct tcgccggcgc ggtgatctgg gcggcatact gcacggtgac cacgcggatc    540

gccggcggca agaacggtgt cacgctgttc ttcatgctga cggcattggc gctatgggcc    600

aagtacctgg ccatcggcgg ggaaacgatg gaattcagct accacgcgct gatctacctg    660

gtgctggccg cctccgcgat gggcttcggc tatgcggcgt ggaacgtcgg catcctgcac    720

ggcaatgtca ccgtcctcgc tggtgcttcg tatttcatcc cggtgctgtc cgccgccctg    780

gcggccgtac tgttgcgtac gccgctgtcg ctgtcgttct ggcagggtgc cgccatggtc    840

tgcatcgggt cgatcctctg ctggttcgcc acccgtgcga aaccgccaga atcggcgcag    900

tcgggtgacc aggccagcgc aaccacgccg cgtcgaaacg gataa                    945
```

<210> SEQ ID NO 11
<211> LENGTH: 35
<212> TYPE: DNA
<213> ORGANISM: Artificial Sequence
<220> FEATURE:
<223> OTHER INFORMATION: Pst-1

<400> SEQUENCE: 11

```
tagaggagac acaacatgaa aaaccagcgt aaagc                                35
```

<210> SEQ ID NO 12
<211> LENGTH: 35
<212> TYPE: DNA
<213> ORGANISM: Artificial Sequence
<220> FEATURE:

<223> OTHER INFORMATION: Pst-2

<400> SEQUENCE: 12
ggctcttcct gtttagttta tccgtttcga cgcgg 35

<210> SEQ ID NO 13
<211> LENGTH: 39
<212> TYPE: DNA
<213> ORGANISM: Artificial Sequence
<220> FEATURE:
<223> OTHER INFORMATION: PgapA(-Pst)-2

<400> SEQUENCE: 13
acgctggttt ttcatgttgt gtctcctcta aagattgta 39

<210> SEQ ID NO 14
<211> LENGTH: 303
<212> TYPE: PRT
<213> ORGANISM: Artificial Sequence
<220> FEATURE:
<223> OTHER INFORMATION: Afa AA seq.

<400> SEQUENCE: 14

```
Met Lys Gln Ser Asp Lys Ala Thr Leu Ile Gly Leu Ile Ala Ile Val
1               5                   10                  15

Leu Trp Ser Thr Ile Val Gly Leu Ile Arg Ser Val Ser Asp Ser Leu
            20                  25                  30

Gly Val Thr Gly Gly Ala Ala Leu Ile Tyr Thr Leu Ala Ser Val Phe
        35                  40                  45

Leu Leu Leu Ser Val Gly Trp Val Arg Leu Arg Asp Phe Pro Arg Arg
    50                  55                  60

Tyr Leu Ile Trp Gly Ser Val Leu Phe Val Cys Tyr Glu Leu Cys Leu
65                  70                  75                  80

Ala Leu Ser Ile Gly Tyr Ala His Asn Ser Gln Gln Ala Ile Glu Val
                85                  90                  95

Gly Met Val Asn Tyr Leu Trp Pro Thr Phe Thr Ile Val Ala Ala Ile
            100                 105                 110

Leu Phe Asn Lys Gln Lys Ala Asn Gly Leu Leu Ala Pro Gly Leu Leu
        115                 120                 125

Leu Ser Met Met Gly Ile Ser Trp Ile Leu Gly Gly Glu Gln Gly Leu
    130                 135                 140

Ser Leu His Asn Ile Trp Leu Asn Val Gln Asp Asn Pro Leu Ser Tyr
145                 150                 155                 160

Gly Leu Ala Phe Ser Gly Ala Leu Ile Trp Ala Gly Tyr Ser Thr Met
                165                 170                 175

Thr Ala Arg Ile Ala Gln Gly Lys Asn Gly Ile Thr Leu Phe Phe Met
            180                 185                 190

Leu Thr Ala Ala Ala Leu Trp Val Lys Tyr Leu Val Gln Gly Ala Pro
        195                 200                 205

Ala Met Thr Phe Thr Val Pro Ala Leu Val Tyr Leu Leu Leu Ala Ala
    210                 215                 220

Met Ala Met Gly Phe Gly Tyr Ala Ala Trp Asn Val Gly Ile Leu His
225                 230                 235                 240

Gly Asn Val Thr Ile Leu Ala Gly Ala Ser Tyr Phe Ile Pro Val Phe
                245                 250                 255

Ser Ala Ala Leu Ser Thr Val Leu Leu Gln Ala Pro Leu Thr Leu Thr
            260                 265                 270
```

```
Phe Trp Gln Gly Ser Ser Met Val Cys Leu Gly Ala Leu Leu Cys Trp
        275                 280                 285

Leu Ala Ile Arg Val Arg Lys Pro Arg Ser Leu Lys Ser Ala Ala
    290                 295                 300


<210> SEQ ID NO 15
<211> LENGTH: 912
<212> TYPE: DNA
<213> ORGANISM: Artificial Sequence
<220> FEATURE:
<223> OTHER INFORMATION: Afa NT seq.

<400> SEQUENCE: 15

atgaagcaat ctgataaggc aaccctgatc gggctgatcg ccattgtcct ttggagcacg     60

attgtcggcc tgatacgcag cgtcagcgac tctctgggcg taaccggcgg cgctgccctg    120

atttacaccc tggcctcggt ctttcttctt ttatcagtgg gctgggtacg cttgcgcgac    180

ttcccgcgtc gctacctgat ctggggcagt gtgctgtttg tctgctatga actctgcctg    240

gccctgtcca tcggctatgc ccacaacagc cagcaggcaa ttgaagtggg gatggtcaac    300

tatctgtggc cgacctttac cattgtggcc gccatcttgt tcaataagca aaaagccaat    360

gggctgcttg cacccggcct gctcttgtcc atgatgggaa tcagctggat tctgggcggc    420

gagcaaggct tgagcctgca caacatctgg ctgaatgtgc aggacaatcc cttgagctac    480

ggcctggcct ttagcggcgc gctgatctgg gccggctaca gcaccatgac cgcccgcatc    540

gcccagggca aaaatggcat caccctgttt ttcatgctga cggcagcggc cttgtgggtg    600

aagtacctgg tccaaggtgc tcctgccatg acgtttacgg ttcccgcctt ggtgtatttg    660

ctgctggcgg ccatggcgat gggctttggc tatgccgcct ggaatgtcgg tattttgcat    720

ggcaatgtca ccatcctggc cggcgcttcc tactttattc cggtattttc agccgccctg    780

tccaccgttt tgctgcaagc tccgttgacg ctgaccttct ggcaaggctc gtccatggtg    840

tgtttgggtg ccctgctatg ctggctggcc atccgggttc gcaaaccccg gtcactaaaa    900

agcgctgcct ga                                                        912


<210> SEQ ID NO 16
<211> LENGTH: 35
<212> TYPE: DNA
<213> ORGANISM: Artificial Sequence
<220> FEATURE:
<223> OTHER INFORMATION: Afa-1

<400> SEQUENCE: 16

tagaggagac acaacatgaa gcaatctgat aaggc                                 35


<210> SEQ ID NO 17
<211> LENGTH: 35
<212> TYPE: DNA
<213> ORGANISM: Artificial Sequence
<220> FEATURE:
<223> OTHER INFORMATION: Afa-2

<400> SEQUENCE: 17

gctcttcctg tttagttcag gcagcgcttt ttagt                                 35


<210> SEQ ID NO 18
<211> LENGTH: 39
<212> TYPE: DNA
<213> ORGANISM: Artificial Sequence
<220> FEATURE:
<223> OTHER INFORMATION: PgapA(-Afa)-2
```

<400> SEQUENCE: 18
atcagattgc ttcatgttgt gtctcctcta aagattgta 39

<210> SEQ ID NO 19
<211> LENGTH: 314
<212> TYPE: PRT
<213> ORGANISM: Artificial Sequence
<220> FEATURE:
<223> OTHER INFORMATION: Cne AA seq.

<400> SEQUENCE: 19

```
Met Gln Ser Lys Ser Lys Ala Thr Leu Ile Gly Leu Ile Ala Ile Leu
1               5                   10                  15

Leu Trp Ser Ser Ile Val Gly Leu Ile Arg Gly Val Ser Glu Asn Leu
            20                  25                  30

Gly Ala Thr Gly Gly Ala Ala Met Ile Tyr Thr Val Ala Ser Ala Leu
        35                  40                  45

Leu Leu Leu Thr Val Gly Phe Val Arg Met Gln Asp Phe Pro Arg Arg
    50                  55                  60

Tyr Leu Val Trp Gly Ser Ile Leu Phe Val Ser Tyr Glu Leu Cys Leu
65                  70                  75                  80

Ser Leu Ser Ile Gly Tyr Ala Asn Ser Ser Arg Gln Ala Ile Glu Val
                85                  90                  95

Gly Met Val Asn Tyr Leu Trp Pro Ser Phe Thr Met Leu Cys Ala Ile
            100                 105                 110

Ala Phe Asn Lys Gln Lys Ala Asn Leu Leu Ile Ile Pro Gly Phe Leu
        115                 120                 125

Ile Ala Ile Leu Gly Ile Cys Trp Val Leu Gly Gly Asp Gln Gly Leu
    130                 135                 140

Asp Phe Ala Gly Met Ala Glu Asn Ile Gln Asp Asn Pro Leu Ser Tyr
145                 150                 155                 160

Gly Leu Ala Phe Leu Gly Ala Leu Ile Trp Ala Ala Tyr Cys Thr Val
                165                 170                 175

Thr Asn Arg Ile Ala Glu Gly Arg Asn Gly Ile Thr Leu Phe Phe Met
            180                 185                 190

Leu Thr Ala Leu Ala Leu Trp Ile Lys Tyr Phe Ala Thr Glu Ser Gly
        195                 200                 205

Ser Met Glu Phe Ser Tyr Gln Ala Val Ile Tyr Leu Ala Leu Ala Ala
    210                 215                 220

Ser Ala Met Gly Phe Gly Tyr Ala Ala Trp Asn Val Gly Ile Leu His
225                 230                 235                 240

Gly Asn Val Thr Val Leu Ala Gly Ala Ser Tyr Phe Ile Pro Val Leu
                245                 250                 255

Ser Ala Ala Leu Ala Ala Met Leu Leu Arg Thr Pro Leu Ser Ile Ala
            260                 265                 270

Phe Trp Lys Gly Ala Ser Met Val Cys Ala Gly Ser Ile Leu Cys Trp
        275                 280                 285

Leu Ala Thr Arg Gly Gln Arg Ser Lys Ala Pro Pro Leu Pro Glu Leu
    290                 295                 300

Pro Gln Ser Arg Glu Arg Val Gln Glu Pro
305                 310
```

<210> SEQ ID NO 20
<211> LENGTH: 945
<212> TYPE: DNA

<213> ORGANISM: Artificial Sequence
<220> FEATURE:
<223> OTHER INFORMATION: Cne NT seq.

<400> SEQUENCE: 20

```
atgcaaagca agagcaaagc aactctcatc gggctcatcg cgattctgtt atggagctcg     60

attgtcggcc tgattcgcgg tgtcagcgaa aaccttgggg caaccggtgg ggcggcaatg    120

atctataccg tcgcctcggc cctgctcttg ctgacagtcg gtttcgtcag aatgcaggat    180

tttccccggc gctatctggt ttggggaagc attctgttcg tttcgtacga gctgtgtctt    240

tccttgtcca ttggctacgc caacagcagc aggcaagcca ttgaggtggg gatggtcaac    300

tacttgtggc cgagcttcac catgctgtgt gccatcgcat tcaacaagca gaaggccaac    360

ttgctgatca ttcccggctt cctgatcgcc attctcggga tctgctgggt gcttggcggg    420

gatcagggcc tggacttcgc cgggatggcg gagaacatcc aggacaatcc gctcagctat    480

gggctggcct tccttggtgc cctgatctgg gcggcgtatt gcactgtgac caaccggatt    540

gccgaaggca ggaatggcat cacgctgttc ttcatgctga cagcgctggc gttgtggatc    600

aagtatttcg ccacagagag cgggtcgatg gaatttagct atcaggcagt gatttatctt    660

gcgttggccg cctctgcgat gggattcggc tatgcggcct ggaatgttgg catcctgcat    720

ggcaatgtca ccgtccttgc cggcgcttcc tacttcattc cggtactttc cgccgccctg    780

gcggccatgc tcttgcgtac acccctgtcg atcgccttct ggaagggcgc atccatggta    840

tgtgcggggt cgatcctctg ttggctggca acacgtgggc aacgttccaa ggcacctccg    900

ttgccggaat taccgcagtc gcgcgaacgt gtccaggaac cgtga                    945
```

<210> SEQ ID NO 21
<211> LENGTH: 35
<212> TYPE: DNA
<213> ORGANISM: Artificial Sequence
<220> FEATURE:
<223> OTHER INFORMATION: Cne-1

<400> SEQUENCE: 21

```
tagaggagac acaacatgca aagcaagagc aaagc                                35
```

<210> SEQ ID NO 22
<211> LENGTH: 35
<212> TYPE: DNA
<213> ORGANISM: Artificial Sequence
<220> FEATURE:
<223> OTHER INFORMATION: Cne-2

<400> SEQUENCE: 22

```
ggctcttcct gtttagttca cggttcctgg acacg                                35
```

<210> SEQ ID NO 23
<211> LENGTH: 39
<212> TYPE: DNA
<213> ORGANISM: Artificial Sequence
<220> FEATURE:
<223> OTHER INFORMATION: PgapA(-Cne)-2

<400> SEQUENCE: 23

```
gctcttgctt tgcatgttgt gtctcctcta aagattgta                            39
```

<210> SEQ ID NO 24
<211> LENGTH: 293
<212> TYPE: PRT
<213> ORGANISM: Artificial Sequence
<220> FEATURE:
<223> OTHER INFORMATION: Eco AA seq.

<400> SEQUENCE: 24

```
Met Thr Arg Gln Lys Ala Thr Leu Ile Gly Leu Ile Ala Ile Val Leu
1               5                   10                  15

Trp Ser Thr Met Val Gly Leu Ile Arg Gly Val Ser Glu Gly Leu Gly
            20                  25                  30

Pro Val Gly Gly Ala Ala Ala Ile Tyr Ser Leu Ser Gly Leu Leu Leu
        35                  40                  45

Ile Phe Thr Val Gly Phe Pro Arg Ile Arg Gln Ile Pro Lys Gly Tyr
    50                  55                  60

Leu Leu Ala Gly Ser Leu Leu Phe Val Ser Tyr Glu Ile Cys Leu Ala
65                  70                  75                  80

Leu Ser Leu Gly Tyr Ala Ala Thr His His Gln Ala Ile Glu Val Gly
                85                  90                  95

Met Val Asn Tyr Leu Trp Pro Ser Leu Thr Ile Leu Phe Ala Ile Leu
            100                 105                 110

Phe Asn Gly Gln Lys Thr Asn Trp Leu Ile Val Pro Gly Leu Leu Leu
        115                 120                 125

Ala Leu Val Gly Val Cys Trp Val Leu Gly Gly Asp Asn Gly Leu His
    130                 135                 140

Tyr Asp Glu Ile Ile Asn Asn Ile Thr Thr Ser Pro Leu Ser Tyr Phe
145                 150                 155                 160

Leu Ala Phe Ile Gly Ala Phe Ile Trp Ala Ala Tyr Cys Thr Val Thr
                165                 170                 175

Asn Lys Tyr Ala Arg Gly Phe Asn Gly Ile Thr Val Phe Val Leu Leu
            180                 185                 190

Thr Gly Ala Ser Leu Trp Val Tyr Tyr Phe Leu Thr Pro Gln Pro Glu
        195                 200                 205

Met Ile Phe Ser Thr Pro Val Met Ile Lys Leu Ile Ser Ala Ala Phe
    210                 215                 220

Thr Leu Gly Phe Ala Tyr Ala Ala Trp Asn Val Gly Ile Leu His Gly
225                 230                 235                 240

Asn Val Thr Ile Met Ala Val Gly Ser Tyr Phe Thr Pro Val Leu Ser
                245                 250                 255

Ser Ala Leu Ala Ala Val Leu Leu Ser Ala Pro Leu Ser Phe Ser Phe
            260                 265                 270

Trp Gln Gly Ala Leu Met Val Cys Gly Gly Ser Leu Leu Cys Trp Leu
        275                 280                 285

Ala Thr Arg Arg Gly
    290
```

<210> SEQ ID NO 25
<211> LENGTH: 882
<212> TYPE: DNA
<213> ORGANISM: Artificial Sequence
<220> FEATURE:
<223> OTHER INFORMATION: Eco NT seq.

<400> SEQUENCE: 25

```
atgacacgac aaaaagcaac gctcataggg ctgatagcga tcgtcctgtg gagcacgatg     60

gtaggattga ttcgcggtgt cagtgagggg ctcggcccgg tcggcggcgc agctgctatc    120

tattcattaa gcgggctgct gttaatcttc acggttggat ttccgcgtat tcggcaaatc    180

ccgaaaggct atttactcgc cgggagtctg ttattcgtca gctatgaaat ctgtctggcg    240
```

ctttccttag ggtatgcggc gacccatcat caggcgattg aagtgggtat ggtgaactat 300
ctgtggccca gcctgacaat tctctttgcc attctgttta atggtcagaa aaccaactgg 360
ttgattgtac ctggattatt attagccctc gtcggcgtct gttgggtgtt aggcggtgac 420
aatgggttac attatgatga aatcatcaat aatatcacca ccagcccatt gagttatttc 480
ctggcgttca ttggtgcgtt tatctgggca gcctattgca cagtaacgaa taaatacgca 540
cgcggattta atggaattac cgtttttgtc ctgctaacgg gagcaagtct gtgggtttac 600
tattttctta cgccacaacc agaaatgata tttagcacgc ccgtcatgat taaactcatc 660
tctgcggcat ttaccttagg atttgcttat gctgcatgga atgtcggtat attgcatggc 720
aatgtcacca ttatggcggt aggttcgtat tttacgcctg tactttcctc agcgcttgca 780
gccgtgctgc tcagcgcccc gctgtcgttc tcgttctggc aaggcgcgct gatggtctgc 840
ggcggttccc tgctctgctg gctggcgaca cgtcgtggtt aa 882

<210> SEQ ID NO 26
<211> LENGTH: 35
<212> TYPE: DNA
<213> ORGANISM: Artificial Sequence
<220> FEATURE:
<223> OTHER INFORMATION: Eco-1

<400> SEQUENCE: 26
tagaggagac acaacatgac acgacaaaaa gcaac 35

<210> SEQ ID NO 27
<211> LENGTH: 35
<212> TYPE: DNA
<213> ORGANISM: Artificial Sequence
<220> FEATURE:
<223> OTHER INFORMATION: Eco-2

<400> SEQUENCE: 27
gctcttcctg tttagtttaa ccacgacgtg tcgcc 35

<210> SEQ ID NO 28
<211> LENGTH: 37
<212> TYPE: DNA
<213> ORGANISM: Artificial Sequence
<220> FEATURE:
<223> OTHER INFORMATION: PgapA(-Eco)-2

<400> SEQUENCE: 28
tttttgtcgt gtcatgttgt gtctcctcta aagattg 37

<210> SEQ ID NO 29
<211> LENGTH: 35
<212> TYPE: DNA
<213> ORGANISM: Artificial Sequence
<220> FEATURE:
<223> OTHER INFORMATION: Hrh-3

<400> SEQUENCE: 29
atagagagtg actcaatgaa tagcaagaag gccac 35

<210> SEQ ID NO 30
<211> LENGTH: 33
<212> TYPE: DNA
<213> ORGANISM: Artificial Sequence
<220> FEATURE:
<223> OTHER INFORMATION: Hrh-4

<400> SEQUENCE: 30
tcgagctcgg taccoctaca aacagtccgc cac 33

<210> SEQ ID NO 31
<211> LENGTH: 34
<212> TYPE: DNA
<213> ORGANISM: Artificial Sequence
<220> FEATURE:
<223> OTHER INFORMATION: PyccA - 1

<400> SEQUENCE: 31
ctctagagga tcccottcca gatcaaatgc gtaa 34

<210> SEQ ID NO 32
<211> LENGTH: 35
<212> TYPE: DNA
<213> ORGANISM: Artificial Sequence
<220> FEATURE:
<223> OTHER INFORMATION: PyccA(-Hrh)-2

<400> SEQUENCE: 32
cttcttgcta ttcattgagt cactctctat gacag 35

<210> SEQ ID NO 33
<211> LENGTH: 35
<212> TYPE: DNA
<213> ORGANISM: Artificial Sequence
<220> FEATURE:
<223> OTHER INFORMATION: Pst-3

<400> SEQUENCE: 33
atagagagtg actcaatgaa aaaccagcgt aaagc 35

<210> SEQ ID NO 34
<211> LENGTH: 33
<212> TYPE: DNA
<213> ORGANISM: Artificial Sequence
<220> FEATURE:
<223> OTHER INFORMATION: Pst-4

<400> SEQUENCE: 34
tcgagctcgg taccottatc cgtttcgacg cgg 33

<210> SEQ ID NO 35
<211> LENGTH: 35
<212> TYPE: DNA
<213> ORGANISM: Artificial Sequence
<220> FEATURE:
<223> OTHER INFORMATION: PyccA(-Pst)-2

<400> SEQUENCE: 35
acgctggttt ttcattgagt cactctctat gacag 35

<210> SEQ ID NO 36
<211> LENGTH: 35
<212> TYPE: DNA
<213> ORGANISM: Artificial Sequence
<220> FEATURE:
<223> OTHER INFORMATION: Afa-3

<400> SEQUENCE: 36
atagagagtg actcaatgaa gcaatctgat aaggc 35

<210> SEQ ID NO 37
<211> LENGTH: 34

<212> TYPE: DNA
<213> ORGANISM: Artificial Sequence
<220> FEATURE:
<223> OTHER INFORMATION: Afa-4

<400> SEQUENCE: 37
tcgagctcgg taccctcagg cagcgctttt tagt 34

<210> SEQ ID NO 38
<211> LENGTH: 35
<212> TYPE: DNA
<213> ORGANISM: Artificial Sequence
<220> FEATURE:
<223> OTHER INFORMATION: PyccA(-Afa)-2

<400> SEQUENCE: 38
atcagattgc ttcattgagt cactctctat gacag 35

<210> SEQ ID NO 39
<211> LENGTH: 35
<212> TYPE: DNA
<213> ORGANISM: Artificial Sequence
<220> FEATURE:
<223> OTHER INFORMATION: Cne-3

<400> SEQUENCE: 39
atagagagtg actcaatgca aagcaagagc aaagc 35

<210> SEQ ID NO 40
<211> LENGTH: 33
<212> TYPE: DNA
<213> ORGANISM: Artificial Sequence
<220> FEATURE:
<223> OTHER INFORMATION: Cne-4

<400> SEQUENCE: 40
tcgagctcgg taccctcacg gttcctggac acg 33

<210> SEQ ID NO 41
<211> LENGTH: 35
<212> TYPE: DNA
<213> ORGANISM: Artificial Sequence
<220> FEATURE:
<223> OTHER INFORMATION: PyccA(-Cne)-2

<400> SEQUENCE: 41
gctcttgctt tgcattgagt cactctctat gacag 35

<210> SEQ ID NO 42
<211> LENGTH: 35
<212> TYPE: DNA
<213> ORGANISM: Artificial Sequence
<220> FEATURE:
<223> OTHER INFORMATION: Eco-3

<400> SEQUENCE: 42
atagagagtg actcaatgac acgacaaaaa gcaac 35

<210> SEQ ID NO 43
<211> LENGTH: 34
<212> TYPE: DNA
<213> ORGANISM: Artificial Sequence
<220> FEATURE:
<223> OTHER INFORMATION: Eco-4

<400> SEQUENCE: 43

```
tcgagctcgg tacccttaac cacgacgtgt cgcc                              34


<210> SEQ ID NO 44
<211> LENGTH: 35
<212> TYPE: DNA
<213> ORGANISM: Artificial Sequence
<220> FEATURE:
<223> OTHER INFORMATION: PyccA(-Eco)-2

<400> SEQUENCE: 44

tttttgtcgt gtcattgagt cactctctat gacag                             35


<210> SEQ ID NO 45
<211> LENGTH: 35
<212> TYPE: DNA
<213> ORGANISM: Artificial Sequence
<220> FEATURE:
<223> OTHER INFORMATION: Pspl7-trpE(S38R)_L-1

<400> SEQUENCE: 45

tcgagctcgg tacccaaaca actgcgacgt gtgtc                             35


<210> SEQ ID NO 46
<211> LENGTH: 35
<212> TYPE: DNA
<213> ORGANISM: Artificial Sequence
<220> FEATURE:
<223> OTHER INFORMATION: Pspl7-trpE(S38R)_L-2

<400> SEQUENCE: 46

catgaagcgc cggtacctta atcatttttg ggttc                             35


<210> SEQ ID NO 47
<211> LENGTH: 35
<212> TYPE: DNA
<213> ORGANISM: Artificial Sequence
<220> FEATURE:
<223> OTHER INFORMATION: Pspl7-trpE(S38R)_R-1

<400> SEQUENCE: 47

gccctgttgg aacgcgctga tatcaccacc aagaa                             35


<210> SEQ ID NO 48
<211> LENGTH: 35
<212> TYPE: DNA
<213> ORGANISM: Artificial Sequence
<220> FEATURE:
<223> OTHER INFORMATION: Pspl7-trpE(S38R)_R-2

<400> SEQUENCE: 48

ctctagagga tccccagatg tcaccgttgt aaatg                             35


<210> SEQ ID NO 49
<211> LENGTH: 294
<212> TYPE: DNA
<213> ORGANISM: Artificial Sequence
<220> FEATURE:
<223> OTHER INFORMATION: spl7 promoter seq.

<400> SEQUENCE: 49

ggcgcttcat gtcaacaatc tttaacgttt tcaagttcac aagtcgtgtt caaatggtga    60

caagattgga cactgtgctg aattggcacc aagccctcat aaatgataga tctaaatcga   120

atatcaatat atggtctgtt tattggaacg cgtcccagtg gctgagacgc atccgctaaa   180

gccccaggaa ccctgtgcag aaagaacaaa taatcgtgaa ttttggcagc aacagcaatt   240
```

cctgctacaa ttgaaaacgt gcaaaagcat agattattgg aggagatcaa aaca 294

<210> SEQ ID NO 50
<211> LENGTH: 35
<212> TYPE: DNA
<213> ORGANISM: Artificial Sequence
<220> FEATURE:
<223> OTHER INFORMATION: Pspl7 - 1

<400> SEQUENCE: 50
cccaaaaatg attaaggtac cggcgcttca tgtca 35

<210> SEQ ID NO 51
<211> LENGTH: 37
<212> TYPE: DNA
<213> ORGANISM: Artificial Sequence
<220> FEATURE:
<223> OTHER INFORMATION: Pspl7 - 2

<400> SEQUENCE: 51
gggattcgtg ctcatgatat ctgttttgat ctcctcc 37

<210> SEQ ID NO 52
<211> LENGTH: 35
<212> TYPE: DNA
<213> ORGANISM: Artificial Sequence
<220> FEATURE:
<223> OTHER INFORMATION: trpE (S38R) - 1

<400> SEQUENCE: 52
atcaaaacag atatcatgag cacgaatccc catgt 35

<210> SEQ ID NO 53
<211> LENGTH: 35
<212> TYPE: DNA
<213> ORGANISM: Artificial Sequence
<220> FEATURE:
<223> OTHER INFORMATION: trpE (S38R) - 2

<400> SEQUENCE: 53
gtggtgatat cagcgcgttc caacagggct gcatc 35

<210> SEQ ID NO 54
<211> LENGTH: 19
<212> TYPE: DNA
<213> ORGANISM: Artificial Sequence
<220> FEATURE:
<223> OTHER INFORMATION: Confirm_Pspl7-trpE(S38R) - 1

<400> SEQUENCE: 54
gaagaagagg ctgcagatg 19

<210> SEQ ID NO 55
<211> LENGTH: 18
<212> TYPE: DNA
<213> ORGANISM: Artificial Sequence
<220> FEATURE:
<223> OTHER INFORMATION: Confirm_Pspl7-trpE(S38R) - 2

<400> SEQUENCE: 55
gatcagcgcc atcatgtt 18

<210> SEQ ID NO 56
<211> LENGTH: 35
<212> TYPE: DNA

<213> ORGANISM: Artificial Sequence
<220> FEATURE:
<223> OTHER INFORMATION: Pn-tkt_L - 1

<400> SEQUENCE: 56
tcgagctcgg tacccaaact ttgagtgggt gcgtg 35

<210> SEQ ID NO 57
<211> LENGTH: 35
<212> TYPE: DNA
<213> ORGANISM: Artificial Sequence
<220> FEATURE:
<223> OTHER INFORMATION: Pn-tkt_L - 2

<400> SEQUENCE: 57
tcgagctacg agggcggttc ccagcccttc attag 35

<210> SEQ ID NO 58
<211> LENGTH: 35
<212> TYPE: DNA
<213> ORGANISM: Artificial Sequence
<220> FEATURE:
<223> OTHER INFORMATION: Pn-tkt_R - 1

<400> SEQUENCE: 58
attaacggtt aattgattct ggacgtcatg actac 35

<210> SEQ ID NO 59
<211> LENGTH: 35
<212> TYPE: DNA
<213> ORGANISM: Artificial Sequence
<220> FEATURE:
<223> OTHER INFORMATION: Pn-tkt_R - 2

<400> SEQUENCE: 59
ctctagagga tccccgcctc gatgatgcag tcgtc 35

<210> SEQ ID NO 60
<211> LENGTH: 35
<212> TYPE: DNA
<213> ORGANISM: Artificial Sequence
<220> FEATURE:
<223> OTHER INFORMATION: Pn-tkt - 1

<400> SEQUENCE: 60
gaagggctgg gaaccgccct cgtagctcga gagtt 35

<210> SEQ ID NO 61
<211> LENGTH: 37
<212> TYPE: DNA
<213> ORGANISM: Artificial Sequence
<220> FEATURE:
<223> OTHER INFORMATION: Pn-tkt - 2

<400> SEQUENCE: 61
catgacgtcc agaatcaatt aaccgttaat ggagtcc 37

<210> SEQ ID NO 62
<211> LENGTH: 20
<212> TYPE: DNA
<213> ORGANISM: Artificial Sequence
<220> FEATURE:
<223> OTHER INFORMATION: Confirm_Pn-tkt - 1

<400> SEQUENCE: 62
acccagaacc ccaaattttc 20

<210> SEQ ID NO 63
<211> LENGTH: 19
<212> TYPE: DNA
<213> ORGANISM: Artificial Sequence
<220> FEATURE:
<223> OTHER INFORMATION: Confirm_Pn-tkt - 2

<400> SEQUENCE: 63
ttgagttcga caactttgg 19

<210> SEQ ID NO 64
<211> LENGTH: 70
<212> TYPE: DNA
<213> ORGANISM: Artificial Sequence
<220> FEATURE:
<223> OTHER INFORMATION: primer

<400> SEQUENCE: 64
tgcaatgcat aacaacgcag tcgcactatt tttcactgga gagaagccct gtgtaggctg 60
gagctgcttc 70

<210> SEQ ID NO 65
<211> LENGTH: 70
<212> TYPE: DNA
<213> ORGANISM: Artificial Sequence
<220> FEATURE:
<223> OTHER INFORMATION: primer

<400> SEQUENCE: 65
tgcaatgcat aacaacgcag tcgcactatt tttcactgga gagaagccct gtccatatga 60
atatcctcct 70

<210> SEQ ID NO 66
<211> LENGTH: 20
<212> TYPE: DNA
<213> ORGANISM: Artificial Sequence
<220> FEATURE:
<223> OTHER INFORMATION: primer

<400> SEQUENCE: 66
gggcaggatc tcctgtcatc 20

<210> SEQ ID NO 67
<211> LENGTH: 20
<212> TYPE: DNA
<213> ORGANISM: Artificial Sequence
<220> FEATURE:
<223> OTHER INFORMATION: primer

<400> SEQUENCE: 67
aaatgtcgga taaggcaccg 20

<210> SEQ ID NO 68
<211> LENGTH: 70
<212> TYPE: DNA
<213> ORGANISM: Artificial Sequence
<220> FEATURE:
<223> OTHER INFORMATION: primer

<400> SEQUENCE: 68
tgtaatattc acagggatca ctgtaattaa aataaatgaa ggattatgta gtgtaggctg 60
gagctgcttc 70

<210> SEQ ID NO 69
<211> LENGTH: 70
<212> TYPE: DNA
<213> ORGANISM: Artificial Sequence
<220> FEATURE:
<223> OTHER INFORMATION: primer

<400> SEQUENCE: 69
tgtagggtaa gagagtggct aacatcctta tagccactct gtagtattaa gtccatatga 60
atatcctcct 70

<210> SEQ ID NO 70
<211> LENGTH: 20
<212> TYPE: DNA
<213> ORGANISM: Artificial Sequence
<220> FEATURE:
<223> OTHER INFORMATION: primer

<400> SEQUENCE: 70
acatccttat agccactctg 20

<210> SEQ ID NO 71
<211> LENGTH: 70
<212> TYPE: DNA
<213> ORGANISM: Artificial Sequence
<220> FEATURE:
<223> OTHER INFORMATION: primer

<400> SEQUENCE: 71
tacaaccggg ggaggcattt tgcttccccc gctaacaatg gcgacatatt gtgtaggctg 60
gagctgcttc 70

<210> SEQ ID NO 72
<211> LENGTH: 70
<212> TYPE: DNA
<213> ORGANISM: Artificial Sequence
<220> FEATURE:
<223> OTHER INFORMATION: primer

<400> SEQUENCE: 72
gcattcggtg cacgatgcct gatgcgccac gtcttatcag gcctacaaaa gtccatatga 60
atatcctcct 70

<210> SEQ ID NO 73
<211> LENGTH: 20
<212> TYPE: DNA
<213> ORGANISM: Artificial Sequence
<220> FEATURE:
<223> OTHER INFORMATION: primer

<400> SEQUENCE: 73
aggacggata aggcgttcac 20

<210> SEQ ID NO 74
<211> LENGTH: 26
<212> TYPE: DNA
<213> ORGANISM: Artificial Sequence
<220> FEATURE:
<223> OTHER INFORMATION: trpE - 1

<400> SEQUENCE: 74
gaattcatgc aaacacaaaa accgac 26

<210> SEQ ID NO 75
<211> LENGTH: 25
<212> TYPE: DNA
<213> ORGANISM: Artificial Sequence
<220> FEATURE:
<223> OTHER INFORMATION: trpE - 2

<400> SEQUENCE: 75
gaattctcag aaagtctcct gtgca 25

<210> SEQ ID NO 76
<211> LENGTH: 37
<212> TYPE: DNA
<213> ORGANISM: Artificial Sequence
<220> FEATURE:
<223> OTHER INFORMATION: trpE(P21S) - 1

<400> SEQUENCE: 76
cgcttatcgc gacaattcca ccgcgctttt tcaccag 37

<210> SEQ ID NO 77
<211> LENGTH: 37
<212> TYPE: DNA
<213> ORGANISM: Artificial Sequence
<220> FEATURE:
<223> OTHER INFORMATION: trpE(P21S) - 2

<400> SEQUENCE: 77
ctggtgaaaa agcgcggtgg aattgtcgcg ataagcg 37

<210> SEQ ID NO 78
<211> LENGTH: 35
<212> TYPE: DNA
<213> ORGANISM: Artificial Sequence
<220> FEATURE:
<223> OTHER INFORMATION: primer(wex-1)

<400> SEQUENCE: 78
actctagagg atccccttcc agatcaaatg cgtaa 35

<210> SEQ ID NO 79
<211> LENGTH: 35
<212> TYPE: DNA
<213> ORGANISM: Artificial Sequence
<220> FEATURE:
<223> OTHER INFORMATION: primer(wex-2)

<400> SEQUENCE: 79
attcgagctc ggtaccccta caaacagtcc gccac 35

<210> SEQ ID NO 80
<211> LENGTH: 924
<212> TYPE: DNA
<213> ORGANISM: Artificial Sequence
<220> FEATURE:
<223> OTHER INFORMATION: wex(L79A)

<400> SEQUENCE: 80
atgaatagca agaaggccac gctgatcgga cttactgcag tggtcctctg gagttccatt 60
gtcggattga ttcgcggcgt cagcgaacat ctcggcgcta ccgggggcgc ggcgatgatg 120
tatagcgttg cctcgctgtt tctgctgttg tcggtcggtt tcccgaaact gggttccttt 180
ccgaaaaaat acctcttgtg gggcagcctg ctgtttgtgt cctacgaact ctgcgcatcg 240
ctctccatcg gttatgccaa tacaggcagg caagcaatcg aagtcagcat ggtcaactat 300
ctgtggccgg cattcacgct catcgccgcc attgcattca accggcagag agcgaactgg 360
atggtggtgc ccggattcat cctctcgatt atcggtatct gctgggtgct gggcggtgac 420
caggggctgg acctggcggg catgcttggc aacgtgcagg acaatccgct cagttatggg 480
ctggcttttt tgggcgccgt gatctgggcc gcctattgca ctgtgacggc ccgcctcgcg 540
aaggggaaga acggagtgac gctgttcttc attcttgtgg cattgacgct ctgggtgaag 600
tttttcttcg gcgatcaccg cccgatgtct ttcagcctgc cggcaattgt ctacctgctc 660
ctggcggcgg ccgcgatggg cttcggctat gcggcatgga atgtcgggat cttgcacggt 720
aacgtgaccg tgctggcggg cgtgtcgtac tttatcccgg ttttttcggc ggcgttgtcc 780
gcgatggtgt tgcatgcgcc gttgccgcga tcgttttggg tgggggcgtc gctggtatgc 840
gccggttcga tactgtgctg gctggcaacc agggccaggc gcgcttcggc cgcgcaagaa 900
gatgcggtgg cggactgttt gtag 924

<210> SEQ ID NO 81
<211> LENGTH: 924
<212> TYPE: DNA
<213> ORGANISM: Artificial Sequence
<220> FEATURE:
<223> OTHER INFORMATION: wex(L79V)

<400> SEQUENCE: 81
atgaatagca agaaggccac gctgatcgga cttactgcag tggtcctctg gagttccatt 60
gtcggattga ttcgcggcgt cagcgaacat ctcggcgcta ccgggggcgc ggcgatgatg 120
tatagcgttg cctcgctgtt tctgctgttg tcggtcggtt tcccgaaact gggttccttt 180
ccgaaaaaat acctcttgtg gggcagcctg ctgtttgtgt cctacgaact ctgcgtgtcg 240
ctctccatcg gttatgccaa tacaggcagg caagcaatcg aagtcagcat ggtcaactat 300
ctgtggccgg cattcacgct catcgccgcc attgcattca accggcagag agcgaactgg 360
atggtggtgc ccggattcat cctctcgatt atcggtatct gctgggtgct gggcggtgac 420
caggggctgg acctggcggg catgcttggc aacgtgcagg acaatccgct cagttatggg 480
ctggcttttt tgggcgccgt gatctgggcc gcctattgca ctgtgacggc ccgcctcgcg 540
aaggggaaga acggagtgac gctgttcttc attcttgtgg cattgacgct ctgggtgaag 600
tttttcttcg gcgatcaccg cccgatgtct ttcagcctgc cggcaattgt ctacctgctc 660
ctggcggcgg ccgcgatggg cttcggctat gcggcatgga atgtcgggat cttgcacggt 720
aacgtgaccg tgctggcggg cgtgtcgtac tttatcccgg ttttttcggc ggcgttgtcc 780
gcgatggtgt tgcatgcgcc gttgccgcga tcgttttggg tgggggcgtc gctggtatgc 840
gccggttcga tactgtgctg gctggcaacc agggccaggc gcgcttcggc cgcgcaagaa 900
gatgcggtgg cggactgttt gtag 924

<210> SEQ ID NO 82
<211> LENGTH: 924
<212> TYPE: DNA
<213> ORGANISM: Artificial Sequence
<220> FEATURE:
<223> OTHER INFORMATION: wex(L79I)

<400> SEQUENCE: 82
atgaatagca agaaggccac gctgatcgga cttactgcag tggtcctctg gagttccatt 60
gtcggattga ttcgcggcgt cagcgaacat ctcggcgcta ccgggggcgc ggcgatgatg 120
tatagcgttg cctcgctgtt tctgctgttg tcggtcggtt tcccgaaact gggttccttt 180

```
ccgaaaaaat acctcttgtg gggcagcctg ctgtttgtgt cctacgaact ctgcatctcg    240

ctctccatcg gttatgccaa tacaggcagg caagcaatcg aagtcagcat ggtcaactat    300

ctgtggccgg cattcacgct catcgccgcc attgcattca accggcagag agcgaactgg    360

atggtggtgc ccggattcat cctctcgatt atcggtatct gctgggtgct gggcggtgac    420

caggggctgg acctggcggg catgcttggc aacgtgcagg acaatccgct cagttatggg    480

ctggcttttt tgggcgccgt gatctgggcc gcctattgca ctgtgacggc ccgcctcgcg    540

aaggggaaga acggagtgac gctgttcttc attcttgtgg cattgacgct ctgggtgaag    600

tttttcttcg gcgatcaccg cccgatgtct ttcagcctgc cggcaattgt ctacctgctc    660

ctggcggcgg ccgcgatggg cttcggctat gcggcatgga atgtcgggat cttgcacggt    720

aacgtgaccg tgctggcggg cgtgtcgtac tttatcccgg ttttttcggc ggcgttgtcc    780

gcgatggtgt tgcatgcgcc gttgccgcga tcgttttggg tgggggcgtc gctggtatgc    840

gccggttcga tactgtgctg gctggcaacc agggccaggc gcgcttcggc cgcgcaagaa    900

gatgcggtgg cggactgttt gtag                                           924
```

<210> SEQ ID NO 83
<211> LENGTH: 40
<212> TYPE: DNA
<213> ORGANISM: Artificial Sequence
<220> FEATURE:
<223> OTHER INFORMATION: primer(wex L79A-1)

<400> SEQUENCE: 83

```
gtgtcctacg aactctgcgc atcgctctcc atcggttatg                           40
```

<210> SEQ ID NO 84
<211> LENGTH: 40
<212> TYPE: DNA
<213> ORGANISM: Artificial Sequence
<220> FEATURE:
<223> OTHER INFORMATION: primer(wex L79A-2)

<400> SEQUENCE: 84

```
cataaccgat ggagagcgat gcgcagagtt cgtaggacac                           40
```

<210> SEQ ID NO 85
<211> LENGTH: 40
<212> TYPE: DNA
<213> ORGANISM: Artificial Sequence
<220> FEATURE:
<223> OTHER INFORMATION: primer(wex L79V-1)

<400> SEQUENCE: 85

```
gtgtcctacg aactctgcgt gtcgctctcc atcggttatg                           40
```

<210> SEQ ID NO 86
<211> LENGTH: 40
<212> TYPE: DNA
<213> ORGANISM: Artificial Sequence
<220> FEATURE:
<223> OTHER INFORMATION: primer(wex L79V-2)

<400> SEQUENCE: 86

```
cataaccgat ggagagcgac acgcagagtt cgtaggacac                           40
```

<210> SEQ ID NO 87
<211> LENGTH: 40
<212> TYPE: DNA

<213> ORGANISM: Artificial Sequence
<220> FEATURE:
<223> OTHER INFORMATION: primer(wex L79I-1)

<400> SEQUENCE: 87
gtgtcctacg aactctgcat ctcgctctcc atcggttatg 40

<210> SEQ ID NO 88
<211> LENGTH: 40
<212> TYPE: DNA
<213> ORGANISM: Artificial Sequence
<220> FEATURE:
<223> OTHER INFORMATION: primer(wex L79I-2)

<400> SEQUENCE: 88
cataaccgat ggagagcgag atgcagagtt cgtaggacac 40

<210> SEQ ID NO 89
<211> LENGTH: 924
<212> TYPE: DNA
<213> ORGANISM: Artificial Sequence
<220> FEATURE:
<223> OTHER INFORMATION: wex(S80A)

<400> SEQUENCE: 89
atgaatagca agaaggccac gctgatcgga cttactgcag tggtcctctg gagttccatt 60
gtcggattga ttcgcggcgt cagcgaacat ctcggcgcta ccgggggcgc ggcgatgatg 120
tatagcgttg cctcgctgtt tctgctgttg tcggtcggtt tcccgaaact gggttccttt 180
ccgaaaaaat acctcttgtg gggcagcctg ctgtttgtgt cctacgaact ctgcctggca 240
ctctccatcg gttatgccaa tacaggcagg caagcaatcg aagtcagcat ggtcaactat 300
ctgtggccgg cattcacgct catcgccgcc attgcattca accggcagag agcgaactgg 360
atggtggtgc ccggattcat cctctcgatt atcggtatct gctgggtgct gggcggtgac 420
caggggctgg acctggcggg catgcttggc aacgtgcagg acaatccgct cagttatggg 480
ctggcttttt tgggcgccgt gatctgggcc gcctattgca ctgtgacggc ccgcctcgcg 540
aaggggaaga acggagtgac gctgttcttc attcttgtgg cattgacgct ctgggtgaag 600
tttttcttcg gcgatcaccg cccgatgtct ttcagcctgc cggcaattgt ctacctgctc 660
ctggcggcgg ccgcgatggg cttcggctat gcggcatgga atgtcgggat cttgcacggt 720
aacgtgaccg tgctggcggg cgtgtcgtac tttatcccgg ttttttcggc ggcgttgtcc 780
gcgatggtgt tgcatgcgcc gttgccgcga tcgttttggg tgggggcgtc gctggtatgc 840
gccggttcga tactgtgctg gctggcaacc agggccaggc gcgcttcggc cgcgcaagaa 900
gatgcggtgg cggactgttt gtag 924

<210> SEQ ID NO 90
<211> LENGTH: 924
<212> TYPE: DNA
<213> ORGANISM: Artificial Sequence
<220> FEATURE:
<223> OTHER INFORMATION: wex(S80V)

<400> SEQUENCE: 90
atgaatagca agaaggccac gctgatcgga cttactgcag tggtcctctg gagttccatt 60
gtcggattga ttcgcggcgt cagcgaacat ctcggcgcta ccgggggcgc ggcgatgatg 120
tatagcgttg cctcgctgtt tctgctgttg tcggtcggtt tcccgaaact gggttccttt 180
ccgaaaaaat acctcttgtg gggcagcctg ctgtttgtgt cctacgaact ctgcctggtg 240

```
ctctccatcg gttatgccaa tacaggcagg caagcaatcg aagtcagcat ggtcaactat    300

ctgtggccgg cattcacgct catcgccgcc attgcattca accggcagag agcgaactgg    360

atggtggtgc ccggattcat cctctcgatt atcggtatct gctgggtgct gggcggtgac    420

caggggctgg acctggcggg catgcttggc aacgtgcagg acaatccgct cagttatggg    480

ctggcttttt tgggcgccgt gatctgggcc gcctattgca ctgtgacggc ccgcctcgcg    540

aaggggaaga acggagtgac gctgttcttc attcttgtgg cattgacgct ctgggtgaag    600

tttttcttcg gcgatcaccg cccgatgtct ttcagcctgc cggcaattgt ctacctgctc    660

ctggcggcgg ccgcgatggg cttcggctat gcggcatgga atgtcgggat cttgcacggt    720

aacgtgaccg tgctggcggg cgtgtcgtac tttatcccgg ttttttcggc ggcgttgtcc    780

gcgatggtgt tgcatgcgcc gttgccgcga tcgttttggg tgggggcgtc gctggtatgc    840

gccggttcga tactgtgctg gctggcaacc agggccaggc gcgcttcggc cgcgcaagaa    900

gatgcggtgg cggactgttt gtag                                          924
```

```
<210> SEQ ID NO 91
<211> LENGTH: 924
<212> TYPE: DNA
<213> ORGANISM: Artificial Sequence
<220> FEATURE:
<223> OTHER INFORMATION: wex(S80L)

<400> SEQUENCE: 91

atgaatagca agaaggccac gctgatcgga cttactgcag tggtcctctg gagttccatt     60

gtcggattga ttcgcggcgt cagcgaacat ctcggcgcta ccgggggcgc ggcgatgatg    120

tatagcgttg cctcgctgtt tctgctgttg tcggtcggtt tcccgaaact gggttccttt    180

ccgaaaaaat acctcttgtg ggcagcctg ctgtttgtgt cctacgaact ctgcctgctg    240

ctctccatcg gttatgccaa tacaggcagg caagcaatcg aagtcagcat ggtcaactat    300

ctgtggccgg cattcacgct catcgccgcc attgcattca accggcagag agcgaactgg    360

atggtggtgc ccggattcat cctctcgatt atcggtatct gctgggtgct gggcggtgac    420

caggggctgg acctggcggg catgcttggc aacgtgcagg acaatccgct cagttatggg    480

ctggcttttt tgggcgccgt gatctgggcc gcctattgca ctgtgacggc ccgcctcgcg    540

aaggggaaga acggagtgac gctgttcttc attcttgtgg cattgacgct ctgggtgaag    600

tttttcttcg gcgatcaccg cccgatgtct ttcagcctgc cggcaattgt ctacctgctc    660

ctggcggcgg ccgcgatggg cttcggctat gcggcatgga atgtcgggat cttgcacggt    720

aacgtgaccg tgctggcggg cgtgtcgtac tttatcccgg ttttttcggc ggcgttgtcc    780

gcgatggtgt tgcatgcgcc gttgccgcga tcgttttggg tgggggcgtc gctggtatgc    840

gccggttcga tactgtgctg gctggcaacc agggccaggc gcgcttcggc cgcgcaagaa    900

gatgcggtgg cggactgttt gtag                                          924
```

```
<210> SEQ ID NO 92
<211> LENGTH: 924
<212> TYPE: DNA
<213> ORGANISM: Artificial Sequence
<220> FEATURE:
<223> OTHER INFORMATION: wex(S80I)

<400> SEQUENCE: 92

atgaatagca agaaggccac gctgatcgga cttactgcag tggtcctctg gagttccatt     60
```

```
gtcggattga ttcgcggcgt cagcgaacat ctcggcgcta ccgggggcgc ggcgatgatg    120

tatagcgttg cctcgctgtt tctgctgttg tcggtcggtt tcccgaaact gggttccttt    180

ccgaaaaaat acctcttgtg gggcagcctg ctgtttgtgt cctacgaact ctgcctgatc    240

ctctccatcg gttatgccaa tacaggcagg caagcaatcg aagtcagcat ggtcaactat    300

ctgtggccgg cattcacgct catcgccgcc attgcattca accggcagag agcgaactgg    360

atggtggtgc ccggattcat cctctcgatt atcggtatct gctgggtgct gggcggtgac    420

caggggctgg acctggcggg catgcttggc aacgtgcagg acaatccgct cagttatggg    480

ctggcttttt tgggcgccgt gatctgggcc gcctattgca ctgtgacggc ccgcctcgcg    540

aaggggaaga acggagtgac gctgttcttc attcttgtgg cattgacgct ctgggtgaag    600

tttttcttcg gcgatcaccg cccgatgtct ttcagcctgc cggcaattgt ctacctgctc    660

ctggcggcgg ccgcgatggg cttcggctat gcggcatgga atgtcgggat cttgcacggt    720

aacgtgaccg tgctggcggg cgtgtcgtac tttatcccgg ttttttcggc ggcgttgtcc    780

gcgatggtgt tgcatgcgcc gttgccgcga tcgttttggg tgggggcgtc gctggtatgc    840

gccggttcga tactgtgctg gctggcaacc agggccaggc gcgcttcggc cgcgcaagaa    900

gatgcggtgg cggactgttt gtag                                           924
```

<210> SEQ ID NO 93
<211> LENGTH: 40
<212> TYPE: DNA
<213> ORGANISM: Artificial Sequence
<220> FEATURE:
<223> OTHER INFORMATION: primer(wex S80A-1)

<400> SEQUENCE: 93

```
gtcctacgaa ctctgcctgg cactctccat cggttatgcc                          40
```

<210> SEQ ID NO 94
<211> LENGTH: 40
<212> TYPE: DNA
<213> ORGANISM: Artificial Sequence
<220> FEATURE:
<223> OTHER INFORMATION: primer(wex S80A-2)

<400> SEQUENCE: 94

```
ggcataaccg atggagagtg ccaggcagag ttcgtaggac                          40
```

<210> SEQ ID NO 95
<211> LENGTH: 40
<212> TYPE: DNA
<213> ORGANISM: Artificial Sequence
<220> FEATURE:
<223> OTHER INFORMATION: primer(wex S80V-1)

<400> SEQUENCE: 95

```
gtcctacgaa ctctgcctgg tgctctccat cggttatgcc                          40
```

<210> SEQ ID NO 96
<211> LENGTH: 40
<212> TYPE: DNA
<213> ORGANISM: Artificial Sequence
<220> FEATURE:
<223> OTHER INFORMATION: primer(wex S80V-2)

<400> SEQUENCE: 96

```
ggcataaccg atggagagca ccaggcagag ttcgtaggac                          40
```

<210> SEQ ID NO 97
<211> LENGTH: 40
<212> TYPE: DNA
<213> ORGANISM: Artificial Sequence
<220> FEATURE:
<223> OTHER INFORMATION: primer(wex S80L-1)

<400> SEQUENCE: 97
gtcctacgaa ctctgcctgc tgctctccat cggttatgcc 40

<210> SEQ ID NO 98
<211> LENGTH: 40
<212> TYPE: DNA
<213> ORGANISM: Artificial Sequence
<220> FEATURE:
<223> OTHER INFORMATION: primer(wex S80L-2)

<400> SEQUENCE: 98
ggcataaccg atggagagca gcaggcagag ttcgtaggac 40

<210> SEQ ID NO 99
<211> LENGTH: 40
<212> TYPE: DNA
<213> ORGANISM: Artificial Sequence
<220> FEATURE:
<223> OTHER INFORMATION: primer(wex S80I-1)

<400> SEQUENCE: 99
gtcctacgaa ctctgcctga tcctctccat cggttatgcc 40

<210> SEQ ID NO 100
<211> LENGTH: 40
<212> TYPE: DNA
<213> ORGANISM: Artificial Sequence
<220> FEATURE:
<223> OTHER INFORMATION: primer(wex S80I-2)

<400> SEQUENCE: 100
ggcataaccg atggagagga tcaggcagag ttcgtaggac 40

<210> SEQ ID NO 101
<211> LENGTH: 924
<212> TYPE: DNA
<213> ORGANISM: Artificial Sequence
<220> FEATURE:
<223> OTHER INFORMATION: wex(L81A)

<400> SEQUENCE: 101
atgaatagca agaaggccac gctgatcgga cttactgcag tggtcctctg gagttccatt 60
gtcggattga ttcgcggcgt cagcgaacat ctcggcgcta ccgggggcgc ggcgatgatg 120
tatagcgttg cctcgctgtt tctgctgttg tcggtcggtt tcccgaaact gggttccttt 180
ccgaaaaaat acctcttgtg gggcagcctg ctgtttgtgt cctacgaact ctgcctgtcg 240
gcatccatcg gttatgccaa tacaggcagg caagcaatcg aagtcagcat ggtcaactat 300
ctgtggccgg cattcacgct catcgccgcc attgcattca accggcagag agcgaactgg 360
atggtggtgc ccggattcat cctctcgatt atcggtatct gctgggtgct gggcggtgac 420
caggggctgg acctggcggg catgcttggc aacgtgcagg acaatccgct cagttatggg 480
ctggcttttt tgggcgccgt gatctgggcc gcctattgca ctgtgacggc ccgcctcgcg 540
aaggggaaga acggagtgac gctgttcttc attcttgtgg cattgacgct ctgggtgaag 600
tttttcttcg gcgatcaccg cccgatgtct ttcagcctgc cggcaattgt ctacctgctc 660

```
ctggcggcgg ccgcgatggg cttcggctat gcggcatgga atgtcgggat cttgcacggt    720

aacgtgaccg tgctggcggg cgtgtcgtac tttatcccgg ttttttcggc ggcgttgtcc    780

gcgatggtgt tgcatgcgcc gttgccgcga tcgttttggg tgggggcgtc gctggtatgc    840

gccggttcga tactgtgctg gctggcaacc agggccaggc gcgcttcggc cgcgcaagaa    900

gatgcggtgg cggactgttt gtag                                           924
```

```
<210> SEQ ID NO 102
<211> LENGTH: 924
<212> TYPE: DNA
<213> ORGANISM: Artificial Sequence
<220> FEATURE:
<223> OTHER INFORMATION: wex(L81V)

<400> SEQUENCE: 102

atgaatagca agaaggccac gctgatcgga cttactgcag tggtcctctg gagttccatt     60

gtcggattga ttcgcggcgt cagcgaacat ctcggcgcta ccgggggcgc ggcgatgatg    120

tatagcgttg cctcgctgtt tctgctgttg tcggtcggtt tcccgaaact gggttccttt    180

ccgaaaaaat acctcttgtg gggcagcctg ctgtttgtgt cctacgaact ctgcctgtcg    240

gtgtccatcg gttatgccaa tacaggcagg caagcaatcg aagtcagcat ggtcaactat    300

ctgtggccgg cattcacgct catcgccgcc attgcattca accggcagag agcgaactgg    360

atggtggtgc ccggattcat cctctcgatt atcggtatct gctgggtgct gggcggtgac    420

caggggctgg acctggcggg catgcttggc aacgtgcagg acaatccgct cagttatggg    480

ctggcttttt tgggcgccgt gatctgggcc gcctattgca ctgtgacggc ccgcctcgcg    540

aaggggaaga acggagtgac gctgttcttc attcttgtgg cattgacgct ctgggtgaag    600

tttttcttcg gcgatcaccg cccgatgtct ttcagcctgc cggcaattgt ctacctgctc    660

ctggcggcgg ccgcgatggg cttcggctat gcggcatgga atgtcgggat cttgcacggt    720

aacgtgaccg tgctggcggg cgtgtcgtac tttatcccgg ttttttcggc ggcgttgtcc    780

gcgatggtgt tgcatgcgcc gttgccgcga tcgttttggg tgggggcgtc gctggtatgc    840

gccggttcga tactgtgctg gctggcaacc agggccaggc gcgcttcggc cgcgcaagaa    900

gatgcggtgg cggactgttt gtag                                           924
```

```
<210> SEQ ID NO 103
<211> LENGTH: 924
<212> TYPE: DNA
<213> ORGANISM: Artificial Sequence
<220> FEATURE:
<223> OTHER INFORMATION: wex(L81I)

<400> SEQUENCE: 103

atgaatagca agaaggccac gctgatcgga cttactgcag tggtcctctg gagttccatt     60

gtcggattga ttcgcggcgt cagcgaacat ctcggcgcta ccgggggcgc ggcgatgatg    120

tatagcgttg cctcgctgtt tctgctgttg tcggtcggtt tcccgaaact gggttccttt    180

ccgaaaaaat acctcttgtg gggcagcctg ctgtttgtgt cctacgaact ctgcctgtcg    240

atctccatcg gttatgccaa tacaggcagg caagcaatcg aagtcagcat ggtcaactat    300

ctgtggccgg cattcacgct catcgccgcc attgcattca accggcagag agcgaactgg    360

atggtggtgc ccggattcat cctctcgatt atcggtatct gctgggtgct gggcggtgac    420

caggggctgg acctggcggg catgcttggc aacgtgcagg acaatccgct cagttatggg    480

ctggcttttt tgggcgccgt gatctgggcc gcctattgca ctgtgacggc ccgcctcgcg    540
```

```
aaggggaaga acggagtgac gctgttcttc attcttgtgg cattgacgct ctgggtgaag    600

tttttcttcg gcgatcaccg cccgatgtct ttcagcctgc cggcaattgt ctacctgctc    660

ctggcggcgg ccgcgatggg cttcggctat gcggcatgga atgtcgggat cttgcacggt    720

aacgtgaccg tgctggcggg cgtgtcgtac tttatcccgg ttttttcggc ggcgttgtcc    780

gcgatggtgt tgcatgcgcc gttgccgcga tcgttttggg tgggggcgtc gctggtatgc    840

gccggttcga tactgtgctg gctggcaacc agggccaggc gcgcttcggc cgcgcaagaa    900

gatgcggtgg cggactgttt gtag                                           924


<210> SEQ ID NO 104
<211> LENGTH: 43
<212> TYPE: DNA
<213> ORGANISM: Artificial Sequence
<220> FEATURE:
<223> OTHER INFORMATION: primer(wex L81A-1)

<400> SEQUENCE: 104

cctacgaact ctgcctgtcg gcatccatcg gttatgccaa tac                       43


<210> SEQ ID NO 105
<211> LENGTH: 43
<212> TYPE: DNA
<213> ORGANISM: Artificial Sequence
<220> FEATURE:
<223> OTHER INFORMATION: primer(wex L81A-2)

<400> SEQUENCE: 105

gtattggcat aaccgatgga tgccgacagg cagagttcgt agg                       43


<210> SEQ ID NO 106
<211> LENGTH: 43
<212> TYPE: DNA
<213> ORGANISM: Artificial Sequence
<220> FEATURE:
<223> OTHER INFORMATION: primer(wex L81V-1)

<400> SEQUENCE: 106

cctacgaact ctgcctgtcg gtgtccatcg gttatgccaa tac                       43


<210> SEQ ID NO 107
<211> LENGTH: 43
<212> TYPE: DNA
<213> ORGANISM: Artificial Sequence
<220> FEATURE:
<223> OTHER INFORMATION: primer(wex L81V-2)

<400> SEQUENCE: 107

gtattggcat aaccgatgga caccgacagg cagagttcgt agg                       43


<210> SEQ ID NO 108
<211> LENGTH: 43
<212> TYPE: DNA
<213> ORGANISM: Artificial Sequence
<220> FEATURE:
<223> OTHER INFORMATION: primer(wex L81I-1)

<400> SEQUENCE: 108

cctacgaact ctgcctgtcg atctccatcg gttatgccaa tac                       43


<210> SEQ ID NO 109
<211> LENGTH: 43
<212> TYPE: DNA
```

<213> ORGANISM: Artificial Sequence
<220> FEATURE:
<223> OTHER INFORMATION: primer(wex L81I-2)

<400> SEQUENCE: 109
gtattggcat aaccgatgga gatcgacagg cagagttcgt agg 43

<210> SEQ ID NO 110
<211> LENGTH: 924
<212> TYPE: DNA
<213> ORGANISM: Artificial Sequence
<220> FEATURE:
<223> OTHER INFORMATION: wex(S82A)

<400> SEQUENCE: 110
atgaatagca agaaggccac gctgatcgga cttactgcag tggtcctctg gagttccatt 60
gtcggattga ttcgcggcgt cagcgaacat ctcggcgcta ccgggggcgc ggcgatgatg 120
tatagcgttg cctcgctgtt tctgctgttg tcggtcggtt tcccgaaact gggttccttt 180
ccgaaaaaat acctcttgtg ggcagcctg ctgtttgtgt cctacgaact ctgcctgtcg 240
ctcgcaatcg gttatgccaa tacaggcagg caagcaatcg aagtcagcat ggtcaactat 300
ctgtggccgg cattcacgct catcgccgcc attgcattca accggcagag agcgaactgg 360
atggtggtgc ccggattcat cctctcgatt atcggtatct gctgggtgct gggcggtgac 420
caggggctgg acctggcggg catgcttggc aacgtgcagg acaatccgct cagttatggg 480
ctggcttttt tgggcgccgt gatctgggcc gcctattgca ctgtgacggc ccgcctcgcg 540
aaggggaaga acggagtgac gctgttcttc attcttgtgg cattgacgct ctgggtgaag 600
tttttcttcg gcgatcaccg cccgatgtct ttcagcctgc cggcaattgt ctacctgctc 660
ctggcggcgg ccgcgatggg cttcggctat gcggcatgga atgtcgggat cttgcacggt 720
aacgtgaccg tgctggcggg cgtgtcgtac tttatcccgg ttttttcggc ggcgttgtcc 780
gcgatggtgt tgcatgcgcc gttgccgcga tcgttttggg tgggggcgtc gctggtatgc 840
gccggttcga tactgtgctg gctggcaacc agggccaggc gcgcttcggc cgcgcaagaa 900
gatgcggtgg cggactgttt gtag 924

<210> SEQ ID NO 111
<211> LENGTH: 924
<212> TYPE: DNA
<213> ORGANISM: Artificial Sequence
<220> FEATURE:
<223> OTHER INFORMATION: wex(S82V)

<400> SEQUENCE: 111
atgaatagca agaaggccac gctgatcgga cttactgcag tggtcctctg gagttccatt 60
gtcggattga ttcgcggcgt cagcgaacat ctcggcgcta ccgggggcgc ggcgatgatg 120
tatagcgttg cctcgctgtt tctgctgttg tcggtcggtt tcccgaaact gggttccttt 180
ccgaaaaaat acctcttgtg ggcagcctg ctgtttgtgt cctacgaact ctgcctgtcg 240
ctcgtgatcg gttatgccaa tacaggcagg caagcaatcg aagtcagcat ggtcaactat 300
ctgtggccgg cattcacgct catcgccgcc attgcattca accggcagag agcgaactgg 360
atggtggtgc ccggattcat cctctcgatt atcggtatct gctgggtgct gggcggtgac 420
caggggctgg acctggcggg catgcttggc aacgtgcagg acaatccgct cagttatggg 480
ctggcttttt tgggcgccgt gatctgggcc gcctattgca ctgtgacggc ccgcctcgcg 540
aaggggaaga acggagtgac gctgttcttc attcttgtgg cattgacgct ctgggtgaag 600

```
tttttcttcg gcgatcaccg cccgatgtct ttcagcctgc cggcaattgt ctacctgctc    660

ctggcggcgg ccgcgatggg cttcggctat gcggcatgga atgtcgggat cttgcacggt    720

aacgtgaccg tgctggcggg cgtgtcgtac tttatcccgg ttttttcggc ggcgttgtcc    780

gcgatggtgt tgcatgcgcc gttgccgcga tcgttttggg tgggggcgtc gctggtatgc    840

gccggttcga tactgtgctg gctggcaacc agggccaggc gcgcttcggc cgcgcaagaa    900

gatgcggtgg cggactgttt gtag                                           924
```

```
<210> SEQ ID NO 112
<211> LENGTH: 924
<212> TYPE: DNA
<213> ORGANISM: Artificial Sequence
<220> FEATURE:
<223> OTHER INFORMATION: wex(S82L)

<400> SEQUENCE: 112

atgaatagca agaaggccac gctgatcgga cttactgcag tggtcctctg gagttccatt     60

gtcggattga ttcgcggcgt cagcgaacat ctcggcgcta ccgggggcgc ggcgatgatg    120

tatagcgttg cctcgctgtt tctgctgttg tcggtcggtt tcccgaaact gggttccttt    180

ccgaaaaaat acctcttgtg gggcagcctg ctgtttgtgt cctacgaact ctgcctgtcg    240

ctcctgatcg gttatgccaa tacaggcagg caagcaatcg aagtcagcat ggtcaactat    300

ctgtggccgg cattcacgct catcgccgcc attgcattca accggcagag agcgaactgg    360

atggtggtgc ccggattcat cctctcgatt atcggtatct gctgggtgct gggcggtgac    420

caggggctgg acctggcggg catgcttggc aacgtgcagg acaatccgct cagttatggg    480

ctggcttttt tgggcgccgt gatctgggcc gcctattgca ctgtgacggc ccgcctcgcg    540

aaggggaaga acggagtgac gctgttcttc attcttgtgg cattgacgct ctgggtgaag    600

tttttcttcg gcgatcaccg cccgatgtct ttcagcctgc cggcaattgt ctacctgctc    660

ctggcggcgg ccgcgatggg cttcggctat gcggcatgga atgtcgggat cttgcacggt    720

aacgtgaccg tgctggcggg cgtgtcgtac tttatcccgg ttttttcggc ggcgttgtcc    780

gcgatggtgt tgcatgcgcc gttgccgcga tcgttttggg tgggggcgtc gctggtatgc    840

gccggttcga tactgtgctg gctggcaacc agggccaggc gcgcttcggc cgcgcaagaa    900

gatgcggtgg cggactgttt gtag                                           924
```

```
<210> SEQ ID NO 113
<211> LENGTH: 924
<212> TYPE: DNA
<213> ORGANISM: Artificial Sequence
<220> FEATURE:
<223> OTHER INFORMATION: wex(S82I)

<400> SEQUENCE: 113

atgaatagca agaaggccac gctgatcgga cttactgcag tggtcctctg gagttccatt     60

gtcggattga ttcgcggcgt cagcgaacat ctcggcgcta ccgggggcgc ggcgatgatg    120

tatagcgttg cctcgctgtt tctgctgttg tcggtcggtt tcccgaaact gggttccttt    180

ccgaaaaaat acctcttgtg gggcagcctg ctgtttgtgt cctacgaact ctgcctgtcg    240

ctcatcatcg gttatgccaa tacaggcagg caagcaatcg aagtcagcat ggtcaactat    300

ctgtggccgg cattcacgct catcgccgcc attgcattca accggcagag agcgaactgg    360

atggtggtgc ccggattcat cctctcgatt atcggtatct gctgggtgct gggcggtgac    420
```

-continued

```
caggggctgg acctggcggg catgcttggc aacgtgcagg acaatccgct cagttatggg    480

ctggcttttt tgggcgccgt gatctgggcc gcctattgca ctgtgacggc ccgcctcgcg    540

aaggggaaga acggagtgac gctgttcttc attcttgtgg cattgacgct ctgggtgaag    600

tttttcttcg gcgatcaccg cccgatgtct ttcagcctgc cggcaattgt ctacctgctc    660

ctggcggcgg ccgcgatggg cttcggctat gcggcatgga atgtcgggat cttgcacggt    720

aacgtgaccg tgctggcggg cgtgtcgtac tttatcccgg ttttttcggc ggcgttgtcc    780

gcgatggtgt tgcatgcgcc gttgccgcga tcgttttggg tgggggcgtc gctggtatgc    840

gccggttcga tactgtgctg gctggcaacc agggccaggc gcgcttcggc cgcgcaagaa    900

gatgcggtgg cggactgttt gtag                                           924
```

```
<210> SEQ ID NO 114
<211> LENGTH: 41
<212> TYPE: DNA
<213> ORGANISM: Artificial Sequence
<220> FEATURE:
<223> OTHER INFORMATION: primer(wex S82A-1)

<400> SEQUENCE: 114

cgaactctgc ctgtcgctcg caatcggtta tgccaataca g                         41


<210> SEQ ID NO 115
<211> LENGTH: 41
<212> TYPE: DNA
<213> ORGANISM: Artificial Sequence
<220> FEATURE:
<223> OTHER INFORMATION: primer(wex S82A-2)

<400> SEQUENCE: 115

ctgtattggc ataaccgatt gcgagcgaca ggcagagttc g                         41


<210> SEQ ID NO 116
<211> LENGTH: 41
<212> TYPE: DNA
<213> ORGANISM: Artificial Sequence
<220> FEATURE:
<223> OTHER INFORMATION: primer(wex S82V-1)

<400> SEQUENCE: 116

cgaactctgc ctgtcgctcg tgatcggtta tgccaataca g                         41


<210> SEQ ID NO 117
<211> LENGTH: 41
<212> TYPE: DNA
<213> ORGANISM: Artificial Sequence
<220> FEATURE:
<223> OTHER INFORMATION: primer(wex S82V-2)

<400> SEQUENCE: 117

ctgtattggc ataaccgatc acgagcgaca ggcagagttc g                         41


<210> SEQ ID NO 118
<211> LENGTH: 41
<212> TYPE: DNA
<213> ORGANISM: Artificial Sequence
<220> FEATURE:
<223> OTHER INFORMATION: primer(wex S82L-1)

<400> SEQUENCE: 118

cgaactctgc ctgtcgctcc tgatcggtta tgccaataca g                         41
```

<210> SEQ ID NO 119
<211> LENGTH: 41
<212> TYPE: DNA
<213> ORGANISM: Artificial Sequence
<220> FEATURE:
<223> OTHER INFORMATION: primer(wex S82L-2)

<400> SEQUENCE: 119
ctgtattggc ataaccgatc aggagcgaca ggcagagttc g 41

<210> SEQ ID NO 120
<211> LENGTH: 41
<212> TYPE: DNA
<213> ORGANISM: Artificial Sequence
<220> FEATURE:
<223> OTHER INFORMATION: primer(wex S82I-1)

<400> SEQUENCE: 120
cgaactctgc ctgtcgctca tcatcggtta tgccaataca g 41

<210> SEQ ID NO 121
<211> LENGTH: 41
<212> TYPE: DNA
<213> ORGANISM: Artificial Sequence
<220> FEATURE:
<223> OTHER INFORMATION: primer(wex S82I-2)

<400> SEQUENCE: 121
ctgtattggc ataaccgatg atgagcgaca ggcagagttc g 41

<210> SEQ ID NO 122
<211> LENGTH: 924
<212> TYPE: DNA
<213> ORGANISM: Artificial Sequence
<220> FEATURE:
<223> OTHER INFORMATION: wex(I83A)

<400> SEQUENCE: 122
atgaatagca agaaggccac gctgatcgga cttactgcag tggtcctctg gagttccatt 60
gtcggattga ttcgcggcgt cagcgaacat ctcggcgcta ccgggggcgc ggcgatgatg 120
tatagcgttg cctcgctgtt tctgctgttg tcggtcggtt tcccgaaact gggttccttt 180
ccgaaaaaat acctcttgtg gggcagcctg ctgtttgtgt cctacgaact ctgcctgtcg 240
ctctccgcag gttatgccaa tacaggcagg caagcaatcg aagtcagcat ggtcaactat 300
ctgtggccgg cattcacgct catcgccgcc attgcattca accggcagag agcgaactgg 360
atggtggtgc ccggattcat cctctcgatt atcggtatct gctgggtgct gggcggtgac 420
caggggctgg acctggcggg catgcttggc aacgtgcagg acaatccgct cagttatggg 480
ctggcttttt tgggcgccgt gatctgggcc gcctattgca ctgtgacggc ccgcctcgcg 540
aaggggaaga acggagtgac gctgttcttc attcttgtgg cattgacgct ctgggtgaag 600
tttttcttcg gcgatcaccg cccgatgtct ttcagcctgc cggcaattgt ctacctgctc 660
ctggcggcgg ccgcgatggg cttcggctat gcggcatgga atgtcgggat cttgcacggt 720
aacgtgaccg tgctggcggg cgtgtcgtac tttatcccgg ttttttcggc ggcgttgtcc 780
gcgatggtgt tgcatgcgcc gttgccgcga tcgttttggg tgggggcgtc gctggtatgc 840
gccggttcga tactgtgctg gctggcaacc agggccaggc gcgcttcggc cgcgcaagaa 900
gatgcggtgg cggactgttt gtag 924

<210> SEQ ID NO 123

<211> LENGTH: 924
<212> TYPE: DNA
<213> ORGANISM: Artificial Sequence
<220> FEATURE:
<223> OTHER INFORMATION: wex(I83V)

<400> SEQUENCE: 123

```
atgaatagca agaaggccac gctgatcgga cttactgcag tggtcctctg gagttccatt     60
gtcggattga ttcgcggcgt cagcgaacat ctcggcgcta ccgggggcgc ggcgatgatg    120
tatagcgttg cctcgctgtt tctgctgttg tcggtcggtt tcccgaaact gggttccttt    180
ccgaaaaaat acctcttgtg gggcagcctg ctgtttgtgt cctacgaact ctgcctgtcg    240
ctctccgtgg gttatgccaa tacaggcagg caagcaatcg aagtcagcat ggtcaactat    300
ctgtggccgg cattcacgct catcgccgcc attgcattca accggcagag agcgaactgg    360
atggtggtgc ccggattcat cctctcgatt atcggtatct gctgggtgct gggcggtgac    420
caggggctgg acctggcggg catgcttggc aacgtgcagg acaatccgct cagttatggg    480
ctggcttttt tgggcgccgt gatctgggcc gcctattgca ctgtgacggc ccgcctcgcg    540
aaggggaaga acggagtgac gctgttcttc attcttgtgg cattgacgct ctgggtgaag    600
tttttcttcg gcgatcaccg cccgatgtct ttcagcctgc cggcaattgt ctacctgctc    660
ctggcggcgg ccgcgatggg cttcggctat gcggcatgga atgtcgggat cttgcacggt    720
aacgtgaccg tgctggcggg cgtgtcgtac tttatcccgg tttttcggc ggcgttgtcc    780
gcgatggtgt tgcatgcgcc gttgccgcga tcgttttggg tgggggcgtc gctggtatgc    840
gccggttcga tactgtgctg gctggcaacc agggccaggc gcgcttcggc cgcgcaagaa    900
gatgcggtgg cggactgttt gtag                                           924
```

<210> SEQ ID NO 124
<211> LENGTH: 924
<212> TYPE: DNA
<213> ORGANISM: Artificial Sequence
<220> FEATURE:
<223> OTHER INFORMATION: wex(I83L)

<400> SEQUENCE: 124

```
atgaatagca agaaggccac gctgatcgga cttactgcag tggtcctctg gagttccatt     60
gtcggattga ttcgcggcgt cagcgaacat ctcggcgcta ccgggggcgc ggcgatgatg    120
tatagcgttg cctcgctgtt tctgctgttg tcggtcggtt tcccgaaact gggttccttt    180
ccgaaaaaat acctcttgtg gggcagcctg ctgtttgtgt cctacgaact ctgcctgtcg    240
ctctccctgg gttatgccaa tacaggcagg caagcaatcg aagtcagcat ggtcaactat    300
ctgtggccgg cattcacgct catcgccgcc attgcattca accggcagag agcgaactgg    360
atggtggtgc ccggattcat cctctcgatt atcggtatct gctgggtgct gggcggtgac    420
caggggctgg acctggcggg catgcttggc aacgtgcagg acaatccgct cagttatggg    480
ctggcttttt tgggcgccgt gatctgggcc gcctattgca ctgtgacggc ccgcctcgcg    540
aaggggaaga acggagtgac gctgttcttc attcttgtgg cattgacgct ctgggtgaag    600
tttttcttcg gcgatcaccg cccgatgtct ttcagcctgc cggcaattgt ctacctgctc    660
ctggcggcgg ccgcgatggg cttcggctat gcggcatgga atgtcgggat cttgcacggt    720
aacgtgaccg tgctggcggg cgtgtcgtac tttatcccgg tttttcggc ggcgttgtcc    780
gcgatggtgt tgcatgcgcc gttgccgcga tcgttttggg tgggggcgtc gctggtatgc    840
gccggttcga tactgtgctg gctggcaacc agggccaggc gcgcttcggc cgcgcaagaa    900
```

gatgcggtgg cggactgttt gtag 924

<210> SEQ ID NO 125
<211> LENGTH: 45
<212> TYPE: DNA
<213> ORGANISM: Artificial Sequence
<220> FEATURE:
<223> OTHER INFORMATION: primer(wex I83A-1)

<400> SEQUENCE: 125
gaactctgcc tgtcgctctc cgcaggttat gccaatacag gcagg 45

<210> SEQ ID NO 126
<211> LENGTH: 45
<212> TYPE: DNA
<213> ORGANISM: Artificial Sequence
<220> FEATURE:
<223> OTHER INFORMATION: primer(wex I83A-2)

<400> SEQUENCE: 126
cctgcctgta ttggcataac ctgcggagag cgacaggcag agttc 45

<210> SEQ ID NO 127
<211> LENGTH: 45
<212> TYPE: DNA
<213> ORGANISM: Artificial Sequence
<220> FEATURE:
<223> OTHER INFORMATION: primer(wex I83V-1)

<400> SEQUENCE: 127
gaactctgcc tgtcgctctc cgtgggttat gccaatacag gcagg 45

<210> SEQ ID NO 128
<211> LENGTH: 45
<212> TYPE: DNA
<213> ORGANISM: Artificial Sequence
<220> FEATURE:
<223> OTHER INFORMATION: primer(wex I83V-2)

<400> SEQUENCE: 128
cctgcctgta ttggcataac ccacggagag cgacaggcag agttc 45

<210> SEQ ID NO 129
<211> LENGTH: 45
<212> TYPE: DNA
<213> ORGANISM: Artificial Sequence
<220> FEATURE:
<223> OTHER INFORMATION: primer(wex I83L-1)

<400> SEQUENCE: 129
gaactctgcc tgtcgctctc cctgggttat gccaatacag gcagg 45

<210> SEQ ID NO 130
<211> LENGTH: 45
<212> TYPE: DNA
<213> ORGANISM: Artificial Sequence
<220> FEATURE:
<223> OTHER INFORMATION: primer(wex I83L-2)

<400> SEQUENCE: 130
cctgcctgta ttggcataac ccagggagag cgacaggcag agttc 45

<210> SEQ ID NO 131
<211> LENGTH: 307
<212> TYPE: PRT

<213> ORGANISM: Artificial Sequence
<220> FEATURE:
<223> OTHER INFORMATION: wex L79A

<400> SEQUENCE: 131

```
Met Asn Ser Lys Lys Ala Thr Leu Ile Gly Leu Thr Ala Val Val Leu
1               5                   10                  15

Trp Ser Ser Ile Val Gly Leu Ile Arg Gly Val Ser Glu His Leu Gly
            20                  25                  30

Ala Thr Gly Gly Ala Ala Met Met Tyr Ser Val Ala Ser Leu Phe Leu
        35                  40                  45

Leu Leu Ser Val Gly Phe Pro Lys Leu Gly Ser Phe Pro Lys Lys Tyr
    50                  55                  60

Leu Leu Trp Gly Ser Leu Leu Phe Val Ser Tyr Glu Leu Cys Ala Ser
65                  70                  75                  80

Leu Ser Ile Gly Tyr Ala Asn Thr Gly Arg Gln Ala Ile Glu Val Ser
                85                  90                  95

Met Val Asn Tyr Leu Trp Pro Ala Phe Thr Leu Ile Ala Ala Ile Ala
            100                 105                 110

Phe Asn Arg Gln Arg Ala Asn Trp Met Val Val Pro Gly Phe Ile Leu
        115                 120                 125

Ser Ile Ile Gly Ile Cys Trp Val Leu Gly Gly Asp Gln Gly Leu Asp
    130                 135                 140

Leu Ala Gly Met Leu Gly Asn Val Gln Asp Asn Pro Leu Ser Tyr Gly
145                 150                 155                 160

Leu Ala Phe Leu Gly Ala Val Ile Trp Ala Ala Tyr Cys Thr Val Thr
                165                 170                 175

Ala Arg Leu Ala Lys Gly Lys Asn Gly Val Thr Leu Phe Phe Ile Leu
            180                 185                 190

Val Ala Leu Thr Leu Trp Val Lys Phe Phe Phe Gly Asp His Arg Pro
        195                 200                 205

Met Ser Phe Ser Leu Pro Ala Ile Val Tyr Leu Leu Leu Ala Ala Ala
    210                 215                 220

Ala Met Gly Phe Gly Tyr Ala Ala Trp Asn Val Gly Ile Leu His Gly
225                 230                 235                 240

Asn Val Thr Val Leu Ala Gly Val Ser Tyr Phe Ile Pro Val Phe Ser
                245                 250                 255

Ala Ala Leu Ser Ala Met Val Leu His Ala Pro Leu Pro Arg Ser Phe
            260                 265                 270

Trp Val Gly Ala Ser Leu Val Cys Ala Gly Ser Ile Leu Cys Trp Leu
        275                 280                 285

Ala Thr Arg Ala Arg Arg Ala Ser Ala Ala Gln Glu Asp Ala Val Ala
    290                 295                 300

Asp Cys Leu
305
```

<210> SEQ ID NO 132
<211> LENGTH: 307
<212> TYPE: PRT
<213> ORGANISM: Artificial Sequence
<220> FEATURE:
<223> OTHER INFORMATION: wex L79V

<400> SEQUENCE: 132

```
Met Asn Ser Lys Lys Ala Thr Leu Ile Gly Leu Thr Ala Val Val Leu
1               5                   10                  15
```

```
Trp Ser Ser Ile Val Gly Leu Ile Arg Gly Val Ser Glu His Leu Gly
            20                  25                  30

Ala Thr Gly Gly Ala Ala Met Met Tyr Ser Val Ala Ser Leu Phe Leu
        35                  40                  45

Leu Leu Ser Val Gly Phe Pro Lys Leu Gly Ser Phe Pro Lys Lys Tyr
    50                  55                  60

Leu Leu Trp Gly Ser Leu Leu Phe Val Ser Tyr Glu Leu Cys Val Ser
65                  70                  75                  80

Leu Ser Ile Gly Tyr Ala Asn Thr Gly Arg Gln Ala Ile Glu Val Ser
                85                  90                  95

Met Val Asn Tyr Leu Trp Pro Ala Phe Thr Leu Ile Ala Ala Ile Ala
            100                 105                 110

Phe Asn Arg Gln Arg Ala Asn Trp Met Val Val Pro Gly Phe Ile Leu
        115                 120                 125

Ser Ile Ile Gly Ile Cys Trp Val Leu Gly Gly Asp Gln Gly Leu Asp
    130                 135                 140

Leu Ala Gly Met Leu Gly Asn Val Gln Asp Asn Pro Leu Ser Tyr Gly
145                 150                 155                 160

Leu Ala Phe Leu Gly Ala Val Ile Trp Ala Ala Tyr Cys Thr Val Thr
                165                 170                 175

Ala Arg Leu Ala Lys Gly Lys Asn Gly Val Thr Leu Phe Phe Ile Leu
            180                 185                 190

Val Ala Leu Thr Leu Trp Val Lys Phe Phe Phe Gly Asp His Arg Pro
        195                 200                 205

Met Ser Phe Ser Leu Pro Ala Ile Val Tyr Leu Leu Leu Ala Ala Ala
    210                 215                 220

Ala Met Gly Phe Gly Tyr Ala Ala Trp Asn Val Gly Ile Leu His Gly
225                 230                 235                 240

Asn Val Thr Val Leu Ala Gly Val Ser Tyr Phe Ile Pro Val Phe Ser
                245                 250                 255

Ala Ala Leu Ser Ala Met Val Leu His Ala Pro Leu Pro Arg Ser Phe
            260                 265                 270

Trp Val Gly Ala Ser Leu Val Cys Ala Gly Ser Ile Leu Cys Trp Leu
        275                 280                 285

Ala Thr Arg Ala Arg Arg Ala Ser Ala Ala Gln Glu Asp Ala Val Ala
    290                 295                 300

Asp Cys Leu
305


<210> SEQ ID NO 133
<211> LENGTH: 307
<212> TYPE: PRT
<213> ORGANISM: Artificial Sequence
<220> FEATURE:
<223> OTHER INFORMATION: wex L79I

<400> SEQUENCE: 133

Met Asn Ser Lys Lys Ala Thr Leu Ile Gly Leu Thr Ala Val Val Leu
1               5                   10                  15

Trp Ser Ser Ile Val Gly Leu Ile Arg Gly Val Ser Glu His Leu Gly
            20                  25                  30

Ala Thr Gly Gly Ala Ala Met Met Tyr Ser Val Ala Ser Leu Phe Leu
        35                  40                  45

Leu Leu Ser Val Gly Phe Pro Lys Leu Gly Ser Phe Pro Lys Lys Tyr
    50                  55                  60
```

```
Leu Leu Trp Gly Ser Leu Leu Phe Val Ser Tyr Glu Leu Cys Ile Ser
65                  70                  75                  80

Leu Ser Ile Gly Tyr Ala Asn Thr Gly Arg Gln Ala Ile Glu Val Ser
                85                  90                  95

Met Val Asn Tyr Leu Trp Pro Ala Phe Thr Leu Ile Ala Ala Ile Ala
            100                 105                 110

Phe Asn Arg Gln Arg Ala Asn Trp Met Val Val Pro Gly Phe Ile Leu
        115                 120                 125

Ser Ile Ile Gly Ile Cys Trp Val Leu Gly Gly Asp Gln Gly Leu Asp
    130                 135                 140

Leu Ala Gly Met Leu Gly Asn Val Gln Asp Asn Pro Leu Ser Tyr Gly
145                 150                 155                 160

Leu Ala Phe Leu Gly Ala Val Ile Trp Ala Ala Tyr Cys Thr Val Thr
                165                 170                 175

Ala Arg Leu Ala Lys Gly Lys Asn Gly Val Thr Leu Phe Phe Ile Leu
            180                 185                 190

Val Ala Leu Thr Leu Trp Val Lys Phe Phe Phe Gly Asp His Arg Pro
        195                 200                 205

Met Ser Phe Ser Leu Pro Ala Ile Val Tyr Leu Leu Leu Ala Ala Ala
    210                 215                 220

Ala Met Gly Phe Gly Tyr Ala Ala Trp Asn Val Gly Ile Leu His Gly
225                 230                 235                 240

Asn Val Thr Val Leu Ala Gly Val Ser Tyr Phe Ile Pro Val Phe Ser
                245                 250                 255

Ala Ala Leu Ser Ala Met Val Leu His Ala Pro Leu Pro Arg Ser Phe
            260                 265                 270

Trp Val Gly Ala Ser Leu Val Cys Ala Gly Ser Ile Leu Cys Trp Leu
        275                 280                 285

Ala Thr Arg Ala Arg Arg Ala Ser Ala Ala Gln Glu Asp Ala Val Ala
    290                 295                 300

Asp Cys Leu
305
```

<210> SEQ ID NO 134
<211> LENGTH: 307
<212> TYPE: PRT
<213> ORGANISM: Artificial Sequence
<220> FEATURE:
<223> OTHER INFORMATION: wex S80A

<400> SEQUENCE: 134

```
Met Asn Ser Lys Lys Ala Thr Leu Ile Gly Leu Thr Ala Val Val Leu
1               5                   10                  15

Trp Ser Ser Ile Val Gly Leu Ile Arg Gly Val Ser Glu His Leu Gly
            20                  25                  30

Ala Thr Gly Gly Ala Ala Met Met Tyr Ser Val Ala Ser Leu Phe Leu
        35                  40                  45

Leu Leu Ser Val Gly Phe Pro Lys Leu Gly Ser Phe Pro Lys Lys Tyr
    50                  55                  60

Leu Leu Trp Gly Ser Leu Leu Phe Val Ser Tyr Glu Leu Cys Leu Ala
65                  70                  75                  80

Leu Ser Ile Gly Tyr Ala Asn Thr Gly Arg Gln Ala Ile Glu Val Ser
                85                  90                  95

Met Val Asn Tyr Leu Trp Pro Ala Phe Thr Leu Ile Ala Ala Ile Ala
            100                 105                 110
```

```
Phe Asn Arg Gln Arg Ala Asn Trp Met Val Val Pro Gly Phe Ile Leu
        115                 120                 125

Ser Ile Ile Gly Ile Cys Trp Val Leu Gly Gly Asp Gln Gly Leu Asp
    130                 135                 140

Leu Ala Gly Met Leu Gly Asn Val Gln Asp Asn Pro Leu Ser Tyr Gly
145                 150                 155                 160

Leu Ala Phe Leu Gly Ala Val Ile Trp Ala Ala Tyr Cys Thr Val Thr
                165                 170                 175

Ala Arg Leu Ala Lys Gly Lys Asn Gly Val Thr Leu Phe Phe Ile Leu
            180                 185                 190

Val Ala Leu Thr Leu Trp Val Lys Phe Phe Phe Gly Asp His Arg Pro
        195                 200                 205

Met Ser Phe Ser Leu Pro Ala Ile Val Tyr Leu Leu Leu Ala Ala Ala
    210                 215                 220

Ala Met Gly Phe Gly Tyr Ala Ala Trp Asn Val Gly Ile Leu His Gly
225                 230                 235                 240

Asn Val Thr Val Leu Ala Gly Val Ser Tyr Phe Ile Pro Val Phe Ser
                245                 250                 255

Ala Ala Leu Ser Ala Met Val Leu His Ala Pro Leu Pro Arg Ser Phe
            260                 265                 270

Trp Val Gly Ala Ser Leu Val Cys Ala Gly Ser Ile Leu Cys Trp Leu
        275                 280                 285

Ala Thr Arg Ala Arg Arg Ala Ser Ala Ala Gln Glu Asp Ala Val Ala
    290                 295                 300

Asp Cys Leu
305


<210> SEQ ID NO 135
<211> LENGTH: 307
<212> TYPE: PRT
<213> ORGANISM: Artificial Sequence
<220> FEATURE:
<223> OTHER INFORMATION: wex S80V

<400> SEQUENCE: 135

Met Asn Ser Lys Lys Ala Thr Leu Ile Gly Leu Thr Ala Val Val Leu
1               5                   10                  15

Trp Ser Ser Ile Val Gly Leu Ile Arg Gly Val Ser Glu His Leu Gly
            20                  25                  30

Ala Thr Gly Gly Ala Ala Met Met Tyr Ser Val Ala Ser Leu Phe Leu
        35                  40                  45

Leu Leu Ser Val Gly Phe Pro Lys Leu Gly Ser Phe Pro Lys Lys Tyr
    50                  55                  60

Leu Leu Trp Gly Ser Leu Leu Phe Val Ser Tyr Glu Leu Cys Leu Val
65                  70                  75                  80

Leu Ser Ile Gly Tyr Ala Asn Thr Gly Arg Gln Ala Ile Glu Val Ser
                85                  90                  95

Met Val Asn Tyr Leu Trp Pro Ala Phe Thr Leu Ile Ala Ala Ile Ala
            100                 105                 110

Phe Asn Arg Gln Arg Ala Asn Trp Met Val Val Pro Gly Phe Ile Leu
        115                 120                 125

Ser Ile Ile Gly Ile Cys Trp Val Leu Gly Gly Asp Gln Gly Leu Asp
    130                 135                 140

Leu Ala Gly Met Leu Gly Asn Val Gln Asp Asn Pro Leu Ser Tyr Gly
145                 150                 155                 160
```

```
Leu Ala Phe Leu Gly Ala Val Ile Trp Ala Ala Tyr Cys Thr Val Thr
                165                 170                 175

Ala Arg Leu Ala Lys Gly Lys Asn Gly Val Thr Leu Phe Phe Ile Leu
            180                 185                 190

Val Ala Leu Thr Leu Trp Val Lys Phe Phe Phe Gly Asp His Arg Pro
        195                 200                 205

Met Ser Phe Ser Leu Pro Ala Ile Val Tyr Leu Leu Leu Ala Ala Ala
    210                 215                 220

Ala Met Gly Phe Gly Tyr Ala Ala Trp Asn Val Gly Ile Leu His Gly
225                 230                 235                 240

Asn Val Thr Val Leu Ala Gly Val Ser Tyr Phe Ile Pro Val Phe Ser
                245                 250                 255

Ala Ala Leu Ser Ala Met Val Leu His Ala Pro Leu Pro Arg Ser Phe
            260                 265                 270

Trp Val Gly Ala Ser Leu Val Cys Ala Gly Ser Ile Leu Cys Trp Leu
        275                 280                 285

Ala Thr Arg Ala Arg Arg Ala Ser Ala Ala Gln Glu Asp Ala Val Ala
    290                 295                 300

Asp Cys Leu
305


<210> SEQ ID NO 136
<211> LENGTH: 307
<212> TYPE: PRT
<213> ORGANISM: Artificial Sequence
<220> FEATURE:
<223> OTHER INFORMATION: wex S80L

<400> SEQUENCE: 136

Met Asn Ser Lys Lys Ala Thr Leu Ile Gly Leu Thr Ala Val Val Leu
1               5                   10                  15

Trp Ser Ser Ile Val Gly Leu Ile Arg Gly Val Ser Glu His Leu Gly
            20                  25                  30

Ala Thr Gly Gly Ala Ala Met Met Tyr Ser Val Ala Ser Leu Phe Leu
        35                  40                  45

Leu Leu Ser Val Gly Phe Pro Lys Leu Gly Ser Phe Pro Lys Lys Tyr
    50                  55                  60

Leu Leu Trp Gly Ser Leu Leu Phe Val Ser Tyr Glu Leu Cys Leu Leu
65                  70                  75                  80

Leu Ser Ile Gly Tyr Ala Asn Thr Gly Arg Gln Ala Ile Glu Val Ser
                85                  90                  95

Met Val Asn Tyr Leu Trp Pro Ala Phe Thr Leu Ile Ala Ala Ile Ala
            100                 105                 110

Phe Asn Arg Gln Arg Ala Asn Trp Met Val Val Pro Gly Phe Ile Leu
        115                 120                 125

Ser Ile Ile Gly Ile Cys Trp Val Leu Gly Gly Asp Gln Gly Leu Asp
    130                 135                 140

Leu Ala Gly Met Leu Gly Asn Val Gln Asp Asn Pro Leu Ser Tyr Gly
145                 150                 155                 160

Leu Ala Phe Leu Gly Ala Val Ile Trp Ala Ala Tyr Cys Thr Val Thr
                165                 170                 175

Ala Arg Leu Ala Lys Gly Lys Asn Gly Val Thr Leu Phe Phe Ile Leu
            180                 185                 190

Val Ala Leu Thr Leu Trp Val Lys Phe Phe Phe Gly Asp His Arg Pro
        195                 200                 205
```

```
Met Ser Phe Ser Leu Pro Ala Ile Val Tyr Leu Leu Leu Ala Ala Ala
    210                 215                 220

Ala Met Gly Phe Gly Tyr Ala Ala Trp Asn Val Gly Ile Leu His Gly
225                 230                 235                 240

Asn Val Thr Val Leu Ala Gly Val Ser Tyr Phe Ile Pro Val Phe Ser
                245                 250                 255

Ala Ala Leu Ser Ala Met Val Leu His Ala Pro Leu Pro Arg Ser Phe
            260                 265                 270

Trp Val Gly Ala Ser Leu Val Cys Ala Gly Ser Ile Leu Cys Trp Leu
        275                 280                 285

Ala Thr Arg Ala Arg Arg Ala Ser Ala Ala Gln Glu Asp Ala Val Ala
    290                 295                 300

Asp Cys Leu
305


<210> SEQ ID NO 137
<211> LENGTH: 307
<212> TYPE: PRT
<213> ORGANISM: Artificial Sequence
<220> FEATURE:
<223> OTHER INFORMATION: wex S80I

<400> SEQUENCE: 137

Met Asn Ser Lys Lys Ala Thr Leu Ile Gly Leu Thr Ala Val Val Leu
1               5                   10                  15

Trp Ser Ser Ile Val Gly Leu Ile Arg Gly Val Ser Glu His Leu Gly
            20                  25                  30

Ala Thr Gly Gly Ala Ala Met Met Tyr Ser Val Ala Ser Leu Phe Leu
        35                  40                  45

Leu Leu Ser Val Gly Phe Pro Lys Leu Gly Ser Phe Pro Lys Lys Tyr
    50                  55                  60

Leu Leu Trp Gly Ser Leu Leu Phe Val Ser Tyr Glu Leu Cys Leu Ile
65                  70                  75                  80

Leu Ser Ile Gly Tyr Ala Asn Thr Gly Arg Gln Ala Ile Glu Val Ser
                85                  90                  95

Met Val Asn Tyr Leu Trp Pro Ala Phe Thr Leu Ile Ala Ala Ile Ala
            100                 105                 110

Phe Asn Arg Gln Arg Ala Asn Trp Met Val Val Pro Gly Phe Ile Leu
        115                 120                 125

Ser Ile Ile Gly Ile Cys Trp Val Leu Gly Gly Asp Gln Gly Leu Asp
    130                 135                 140

Leu Ala Gly Met Leu Gly Asn Val Gln Asp Asn Pro Leu Ser Tyr Gly
145                 150                 155                 160

Leu Ala Phe Leu Gly Ala Val Ile Trp Ala Ala Tyr Cys Thr Val Thr
                165                 170                 175

Ala Arg Leu Ala Lys Gly Lys Asn Gly Val Thr Leu Phe Phe Ile Leu
            180                 185                 190

Val Ala Leu Thr Leu Trp Val Lys Phe Phe Phe Gly Asp His Arg Pro
        195                 200                 205

Met Ser Phe Ser Leu Pro Ala Ile Val Tyr Leu Leu Leu Ala Ala Ala
    210                 215                 220

Ala Met Gly Phe Gly Tyr Ala Ala Trp Asn Val Gly Ile Leu His Gly
225                 230                 235                 240

Asn Val Thr Val Leu Ala Gly Val Ser Tyr Phe Ile Pro Val Phe Ser
                245                 250                 255
```

```
Ala Ala Leu Ser Ala Met Val Leu His Ala Pro Leu Pro Arg Ser Phe
            260                 265                 270

Trp Val Gly Ala Ser Leu Val Cys Ala Gly Ser Ile Leu Cys Trp Leu
        275                 280                 285

Ala Thr Arg Ala Arg Arg Ala Ser Ala Ala Gln Glu Asp Ala Val Ala
    290                 295                 300

Asp Cys Leu
305


<210> SEQ ID NO 138
<211> LENGTH: 307
<212> TYPE: PRT
<213> ORGANISM: Artificial Sequence
<220> FEATURE:
<223> OTHER INFORMATION: wex L81A

<400> SEQUENCE: 138

Met Asn Ser Lys Lys Ala Thr Leu Ile Gly Leu Thr Ala Val Val Leu
1               5                   10                  15

Trp Ser Ser Ile Val Gly Leu Ile Arg Gly Val Ser Glu His Leu Gly
            20                  25                  30

Ala Thr Gly Gly Ala Ala Met Met Tyr Ser Val Ala Ser Leu Phe Leu
        35                  40                  45

Leu Leu Ser Val Gly Phe Pro Lys Leu Gly Ser Phe Pro Lys Lys Tyr
    50                  55                  60

Leu Leu Trp Gly Ser Leu Leu Phe Val Ser Tyr Glu Leu Cys Leu Ser
65                  70                  75                  80

Ala Ser Ile Gly Tyr Ala Asn Thr Gly Arg Gln Ala Ile Glu Val Ser
                85                  90                  95

Met Val Asn Tyr Leu Trp Pro Ala Phe Thr Leu Ile Ala Ala Ile Ala
            100                 105                 110

Phe Asn Arg Gln Arg Ala Asn Trp Met Val Val Pro Gly Phe Ile Leu
        115                 120                 125

Ser Ile Ile Gly Ile Cys Trp Val Leu Gly Gly Asp Gln Gly Leu Asp
    130                 135                 140

Leu Ala Gly Met Leu Gly Asn Val Gln Asp Asn Pro Leu Ser Tyr Gly
145                 150                 155                 160

Leu Ala Phe Leu Gly Ala Val Ile Trp Ala Ala Tyr Cys Thr Val Thr
                165                 170                 175

Ala Arg Leu Ala Lys Gly Lys Asn Gly Val Thr Leu Phe Phe Ile Leu
            180                 185                 190

Val Ala Leu Thr Leu Trp Val Lys Phe Phe Phe Gly Asp His Arg Pro
        195                 200                 205

Met Ser Phe Ser Leu Pro Ala Ile Val Tyr Leu Leu Leu Ala Ala Ala
    210                 215                 220

Ala Met Gly Phe Gly Tyr Ala Ala Trp Asn Val Gly Ile Leu His Gly
225                 230                 235                 240

Asn Val Thr Val Leu Ala Gly Val Ser Tyr Phe Ile Pro Val Phe Ser
                245                 250                 255

Ala Ala Leu Ser Ala Met Val Leu His Ala Pro Leu Pro Arg Ser Phe
            260                 265                 270

Trp Val Gly Ala Ser Leu Val Cys Ala Gly Ser Ile Leu Cys Trp Leu
        275                 280                 285

Ala Thr Arg Ala Arg Arg Ala Ser Ala Ala Gln Glu Asp Ala Val Ala
    290                 295                 300
```

```
Asp Cys Leu
305


<210> SEQ ID NO 139
<211> LENGTH: 307
<212> TYPE: PRT
<213> ORGANISM: Artificial Sequence
<220> FEATURE:
<223> OTHER INFORMATION: wex L81V

<400> SEQUENCE: 139

Met Asn Ser Lys Lys Ala Thr Leu Ile Gly Leu Thr Ala Val Val Leu
1               5                   10                  15

Trp Ser Ser Ile Val Gly Leu Ile Arg Gly Val Ser Glu His Leu Gly
            20                  25                  30

Ala Thr Gly Gly Ala Ala Met Met Tyr Ser Val Ala Ser Leu Phe Leu
        35                  40                  45

Leu Leu Ser Val Gly Phe Pro Lys Leu Gly Ser Phe Pro Lys Lys Tyr
    50                  55                  60

Leu Leu Trp Gly Ser Leu Leu Phe Val Ser Tyr Glu Leu Cys Leu Ser
65                  70                  75                  80

Val Ser Ile Gly Tyr Ala Asn Thr Gly Arg Gln Ala Ile Glu Val Ser
                85                  90                  95

Met Val Asn Tyr Leu Trp Pro Ala Phe Thr Leu Ile Ala Ala Ile Ala
            100                 105                 110

Phe Asn Arg Gln Arg Ala Asn Trp Met Val Val Pro Gly Phe Ile Leu
        115                 120                 125

Ser Ile Ile Gly Ile Cys Trp Val Leu Gly Gly Asp Gln Gly Leu Asp
    130                 135                 140

Leu Ala Gly Met Leu Gly Asn Val Gln Asp Asn Pro Leu Ser Tyr Gly
145                 150                 155                 160

Leu Ala Phe Leu Gly Ala Val Ile Trp Ala Ala Tyr Cys Thr Val Thr
                165                 170                 175

Ala Arg Leu Ala Lys Gly Lys Asn Gly Val Thr Leu Phe Phe Ile Leu
            180                 185                 190

Val Ala Leu Thr Leu Trp Val Lys Phe Phe Phe Gly Asp His Arg Pro
        195                 200                 205

Met Ser Phe Ser Leu Pro Ala Ile Val Tyr Leu Leu Leu Ala Ala Ala
    210                 215                 220

Ala Met Gly Phe Gly Tyr Ala Ala Trp Asn Val Gly Ile Leu His Gly
225                 230                 235                 240

Asn Val Thr Val Leu Ala Gly Val Ser Tyr Phe Ile Pro Val Phe Ser
                245                 250                 255

Ala Ala Leu Ser Ala Met Val Leu His Ala Pro Leu Pro Arg Ser Phe
            260                 265                 270

Trp Val Gly Ala Ser Leu Val Cys Ala Gly Ser Ile Leu Cys Trp Leu
        275                 280                 285

Ala Thr Arg Ala Arg Arg Ala Ser Ala Ala Gln Glu Asp Ala Val Ala
    290                 295                 300

Asp Cys Leu
305


<210> SEQ ID NO 140
<211> LENGTH: 307
<212> TYPE: PRT
<213> ORGANISM: Artificial Sequence
<220> FEATURE:
```

<223> OTHER INFORMATION: wex L81I

<400> SEQUENCE: 140

Met Asn Ser Lys Lys Ala Thr Leu Ile Gly Leu Thr Ala Val Val Leu
1 5 10 15

Trp Ser Ser Ile Val Gly Leu Ile Arg Gly Val Ser Glu His Leu Gly
20 25 30

Ala Thr Gly Gly Ala Ala Met Met Tyr Ser Val Ala Ser Leu Phe Leu
35 40 45

Leu Leu Ser Val Gly Phe Pro Lys Leu Gly Ser Phe Pro Lys Lys Tyr
50 55 60

Leu Leu Trp Gly Ser Leu Leu Phe Val Ser Tyr Glu Leu Cys Leu Ser
65 70 75 80

Ile Ser Ile Gly Tyr Ala Asn Thr Gly Arg Gln Ala Ile Glu Val Ser
85 90 95

Met Val Asn Tyr Leu Trp Pro Ala Phe Thr Leu Ile Ala Ala Ile Ala
100 105 110

Phe Asn Arg Gln Arg Ala Asn Trp Met Val Val Pro Gly Phe Ile Leu
115 120 125

Ser Ile Ile Gly Ile Cys Trp Val Leu Gly Gly Asp Gln Gly Leu Asp
130 135 140

Leu Ala Gly Met Leu Gly Asn Val Gln Asp Asn Pro Leu Ser Tyr Gly
145 150 155 160

Leu Ala Phe Leu Gly Ala Val Ile Trp Ala Ala Tyr Cys Thr Val Thr
165 170 175

Ala Arg Leu Ala Lys Gly Lys Asn Gly Val Thr Leu Phe Phe Ile Leu
180 185 190

Val Ala Leu Thr Leu Trp Val Lys Phe Phe Phe Gly Asp His Arg Pro
195 200 205

Met Ser Phe Ser Leu Pro Ala Ile Val Tyr Leu Leu Leu Ala Ala Ala
210 215 220

Ala Met Gly Phe Gly Tyr Ala Ala Trp Asn Val Gly Ile Leu His Gly
225 230 235 240

Asn Val Thr Val Leu Ala Gly Val Ser Tyr Phe Ile Pro Val Phe Ser
245 250 255

Ala Ala Leu Ser Ala Met Val Leu His Ala Pro Leu Pro Arg Ser Phe
260 265 270

Trp Val Gly Ala Ser Leu Val Cys Ala Gly Ser Ile Leu Cys Trp Leu
275 280 285

Ala Thr Arg Ala Arg Arg Ala Ser Ala Ala Gln Glu Asp Ala Val Ala
290 295 300

Asp Cys Leu
305

<210> SEQ ID NO 141
<211> LENGTH: 307
<212> TYPE: PRT
<213> ORGANISM: Artificial Sequence
<220> FEATURE:
<223> OTHER INFORMATION: wex S82A

<400> SEQUENCE: 141

Met Asn Ser Lys Lys Ala Thr Leu Ile Gly Leu Thr Ala Val Val Leu
1 5 10 15

Trp Ser Ser Ile Val Gly Leu Ile Arg Gly Val Ser Glu His Leu Gly
20 25 30

```
Ala Thr Gly Gly Ala Ala Met Met Tyr Ser Val Ala Ser Leu Phe Leu
        35                  40                  45

Leu Leu Ser Val Gly Phe Pro Lys Leu Gly Ser Phe Pro Lys Lys Tyr
    50                  55                  60

Leu Leu Trp Gly Ser Leu Leu Phe Val Ser Tyr Glu Leu Cys Leu Ser
65                  70                  75                  80

Leu Ala Ile Gly Tyr Ala Asn Thr Gly Arg Gln Ala Ile Glu Val Ser
                85                  90                  95

Met Val Asn Tyr Leu Trp Pro Ala Phe Thr Leu Ile Ala Ala Ile Ala
            100                 105                 110

Phe Asn Arg Gln Arg Ala Asn Trp Met Val Val Pro Gly Phe Ile Leu
        115                 120                 125

Ser Ile Ile Gly Ile Cys Trp Val Leu Gly Gly Asp Gln Gly Leu Asp
    130                 135                 140

Leu Ala Gly Met Leu Gly Asn Val Gln Asp Asn Pro Leu Ser Tyr Gly
145                 150                 155                 160

Leu Ala Phe Leu Gly Ala Val Ile Trp Ala Ala Tyr Cys Thr Val Thr
                165                 170                 175

Ala Arg Leu Ala Lys Gly Lys Asn Gly Val Thr Leu Phe Phe Ile Leu
            180                 185                 190

Val Ala Leu Thr Leu Trp Val Lys Phe Phe Phe Gly Asp His Arg Pro
        195                 200                 205

Met Ser Phe Ser Leu Pro Ala Ile Val Tyr Leu Leu Leu Ala Ala Ala
    210                 215                 220

Ala Met Gly Phe Gly Tyr Ala Ala Trp Asn Val Gly Ile Leu His Gly
225                 230                 235                 240

Asn Val Thr Val Leu Ala Gly Val Ser Tyr Phe Ile Pro Val Phe Ser
                245                 250                 255

Ala Ala Leu Ser Ala Met Val Leu His Ala Pro Leu Pro Arg Ser Phe
            260                 265                 270

Trp Val Gly Ala Ser Leu Val Cys Ala Gly Ser Ile Leu Cys Trp Leu
        275                 280                 285

Ala Thr Arg Ala Arg Arg Ala Ser Ala Ala Gln Glu Asp Ala Val Ala
    290                 295                 300

Asp Cys Leu
305


<210> SEQ ID NO 142
<211> LENGTH: 307
<212> TYPE: PRT
<213> ORGANISM: Artificial Sequence
<220> FEATURE:
<223> OTHER INFORMATION: wex S82V

<400> SEQUENCE: 142

Met Asn Ser Lys Lys Ala Thr Leu Ile Gly Leu Thr Ala Val Val Leu
1               5                   10                  15

Trp Ser Ser Ile Val Gly Leu Ile Arg Gly Val Ser Glu His Leu Gly
            20                  25                  30

Ala Thr Gly Gly Ala Ala Met Met Tyr Ser Val Ala Ser Leu Phe Leu
        35                  40                  45

Leu Leu Ser Val Gly Phe Pro Lys Leu Gly Ser Phe Pro Lys Lys Tyr
    50                  55                  60

Leu Leu Trp Gly Ser Leu Leu Phe Val Ser Tyr Glu Leu Cys Leu Ser
65                  70                  75                  80
```

```
Leu Val Ile Gly Tyr Ala Asn Thr Gly Arg Gln Ala Ile Glu Val Ser
                85                  90                  95

Met Val Asn Tyr Leu Trp Pro Ala Phe Thr Leu Ile Ala Ala Ile Ala
            100                 105                 110

Phe Asn Arg Gln Arg Ala Asn Trp Met Val Val Pro Gly Phe Ile Leu
        115                 120                 125

Ser Ile Ile Gly Ile Cys Trp Val Leu Gly Gly Asp Gln Gly Leu Asp
    130                 135                 140

Leu Ala Gly Met Leu Gly Asn Val Gln Asp Asn Pro Leu Ser Tyr Gly
145                 150                 155                 160

Leu Ala Phe Leu Gly Ala Val Ile Trp Ala Ala Tyr Cys Thr Val Thr
                165                 170                 175

Ala Arg Leu Ala Lys Gly Lys Asn Gly Val Thr Leu Phe Phe Ile Leu
            180                 185                 190

Val Ala Leu Thr Leu Trp Val Lys Phe Phe Phe Gly Asp His Arg Pro
        195                 200                 205

Met Ser Phe Ser Leu Pro Ala Ile Val Tyr Leu Leu Leu Ala Ala Ala
    210                 215                 220

Ala Met Gly Phe Gly Tyr Ala Ala Trp Asn Val Gly Ile Leu His Gly
225                 230                 235                 240

Asn Val Thr Val Leu Ala Gly Val Ser Tyr Phe Ile Pro Val Phe Ser
                245                 250                 255

Ala Ala Leu Ser Ala Met Val Leu His Ala Pro Leu Pro Arg Ser Phe
            260                 265                 270

Trp Val Gly Ala Ser Leu Val Cys Ala Gly Ser Ile Leu Cys Trp Leu
        275                 280                 285

Ala Thr Arg Ala Arg Arg Ala Ser Ala Ala Gln Glu Asp Ala Val Ala
    290                 295                 300

Asp Cys Leu
305


<210> SEQ ID NO 143
<211> LENGTH: 307
<212> TYPE: PRT
<213> ORGANISM: Artificial Sequence
<220> FEATURE:
<223> OTHER INFORMATION: wex S82L

<400> SEQUENCE: 143

Met Asn Ser Lys Lys Ala Thr Leu Ile Gly Leu Thr Ala Val Val Leu
1               5                   10                  15

Trp Ser Ser Ile Val Gly Leu Ile Arg Gly Val Ser Glu His Leu Gly
            20                  25                  30

Ala Thr Gly Gly Ala Ala Met Met Tyr Ser Val Ala Ser Leu Phe Leu
        35                  40                  45

Leu Leu Ser Val Gly Phe Pro Lys Leu Gly Ser Phe Pro Lys Lys Tyr
    50                  55                  60

Leu Leu Trp Gly Ser Leu Leu Phe Val Ser Tyr Glu Leu Cys Leu Ser
65                  70                  75                  80

Leu Leu Ile Gly Tyr Ala Asn Thr Gly Arg Gln Ala Ile Glu Val Ser
                85                  90                  95

Met Val Asn Tyr Leu Trp Pro Ala Phe Thr Leu Ile Ala Ala Ile Ala
            100                 105                 110

Phe Asn Arg Gln Arg Ala Asn Trp Met Val Val Pro Gly Phe Ile Leu
        115                 120                 125
```

```
Ser Ile Ile Gly Ile Cys Trp Val Leu Gly Gly Asp Gln Gly Leu Asp
    130                 135                 140

Leu Ala Gly Met Leu Gly Asn Val Gln Asp Asn Pro Leu Ser Tyr Gly
145                 150                 155                 160

Leu Ala Phe Leu Gly Ala Val Ile Trp Ala Ala Tyr Cys Thr Val Thr
                165                 170                 175

Ala Arg Leu Ala Lys Gly Lys Asn Gly Val Thr Leu Phe Phe Ile Leu
            180                 185                 190

Val Ala Leu Thr Leu Trp Val Lys Phe Phe Phe Gly Asp His Arg Pro
        195                 200                 205

Met Ser Phe Ser Leu Pro Ala Ile Val Tyr Leu Leu Leu Ala Ala Ala
    210                 215                 220

Ala Met Gly Phe Gly Tyr Ala Ala Trp Asn Val Gly Ile Leu His Gly
225                 230                 235                 240

Asn Val Thr Val Leu Ala Gly Val Ser Tyr Phe Ile Pro Val Phe Ser
                245                 250                 255

Ala Ala Leu Ser Ala Met Val Leu His Ala Pro Leu Pro Arg Ser Phe
            260                 265                 270

Trp Val Gly Ala Ser Leu Val Cys Ala Gly Ser Ile Leu Cys Trp Leu
        275                 280                 285

Ala Thr Arg Ala Arg Arg Ala Ser Ala Ala Gln Glu Asp Ala Val Ala
    290                 295                 300

Asp Cys Leu
305


<210> SEQ ID NO 144
<211> LENGTH: 307
<212> TYPE: PRT
<213> ORGANISM: Artificial Sequence
<220> FEATURE:
<223> OTHER INFORMATION: wex S82I

<400> SEQUENCE: 144

Met Asn Ser Lys Lys Ala Thr Leu Ile Gly Leu Thr Ala Val Val Leu
1               5                   10                  15

Trp Ser Ser Ile Val Gly Leu Ile Arg Gly Val Ser Glu His Leu Gly
            20                  25                  30

Ala Thr Gly Gly Ala Ala Met Met Tyr Ser Val Ala Ser Leu Phe Leu
        35                  40                  45

Leu Leu Ser Val Gly Phe Pro Lys Leu Gly Ser Phe Pro Lys Lys Tyr
    50                  55                  60

Leu Leu Trp Gly Ser Leu Leu Phe Val Ser Tyr Glu Leu Cys Leu Ser
65                  70                  75                  80

Leu Ile Ile Gly Tyr Ala Asn Thr Gly Arg Gln Ala Ile Glu Val Ser
                85                  90                  95

Met Val Asn Tyr Leu Trp Pro Ala Phe Thr Leu Ile Ala Ala Ile Ala
            100                 105                 110

Phe Asn Arg Gln Arg Ala Asn Trp Met Val Val Pro Gly Phe Ile Leu
        115                 120                 125

Ser Ile Ile Gly Ile Cys Trp Val Leu Gly Gly Asp Gln Gly Leu Asp
    130                 135                 140

Leu Ala Gly Met Leu Gly Asn Val Gln Asp Asn Pro Leu Ser Tyr Gly
145                 150                 155                 160

Leu Ala Phe Leu Gly Ala Val Ile Trp Ala Ala Tyr Cys Thr Val Thr
                165                 170                 175
```

```
Ala Arg Leu Ala Lys Gly Lys Asn Gly Val Thr Leu Phe Phe Ile Leu
            180                 185                 190

Val Ala Leu Thr Leu Trp Val Lys Phe Phe Phe Gly Asp His Arg Pro
        195                 200                 205

Met Ser Phe Ser Leu Pro Ala Ile Val Tyr Leu Leu Leu Ala Ala Ala
    210                 215                 220

Ala Met Gly Phe Gly Tyr Ala Ala Trp Asn Val Gly Ile Leu His Gly
225                 230                 235                 240

Asn Val Thr Val Leu Ala Gly Val Ser Tyr Phe Ile Pro Val Phe Ser
                245                 250                 255

Ala Ala Leu Ser Ala Met Val Leu His Ala Pro Leu Pro Arg Ser Phe
            260                 265                 270

Trp Val Gly Ala Ser Leu Val Cys Ala Gly Ser Ile Leu Cys Trp Leu
        275                 280                 285

Ala Thr Arg Ala Arg Arg Ala Ser Ala Ala Gln Glu Asp Ala Val Ala
    290                 295                 300

Asp Cys Leu
305


<210> SEQ ID NO 145
<211> LENGTH: 307
<212> TYPE: PRT
<213> ORGANISM: Artificial Sequence
<220> FEATURE:
<223> OTHER INFORMATION: wex I83A

<400> SEQUENCE: 145

Met Asn Ser Lys Lys Ala Thr Leu Ile Gly Leu Thr Ala Val Val Leu
1               5                   10                  15

Trp Ser Ser Ile Val Gly Leu Ile Arg Gly Val Ser Glu His Leu Gly
            20                  25                  30

Ala Thr Gly Gly Ala Ala Met Met Tyr Ser Val Ala Ser Leu Phe Leu
        35                  40                  45

Leu Leu Ser Val Gly Phe Pro Lys Leu Gly Ser Phe Pro Lys Lys Tyr
    50                  55                  60

Leu Leu Trp Gly Ser Leu Leu Phe Val Ser Tyr Glu Leu Cys Leu Ser
65                  70                  75                  80

Leu Ser Ala Gly Tyr Ala Asn Thr Gly Arg Gln Ala Ile Glu Val Ser
                85                  90                  95

Met Val Asn Tyr Leu Trp Pro Ala Phe Thr Leu Ile Ala Ala Ile Ala
            100                 105                 110

Phe Asn Arg Gln Arg Ala Asn Trp Met Val Val Pro Gly Phe Ile Leu
        115                 120                 125

Ser Ile Ile Gly Ile Cys Trp Val Leu Gly Gly Asp Gln Gly Leu Asp
    130                 135                 140

Leu Ala Gly Met Leu Gly Asn Val Gln Asp Asn Pro Leu Ser Tyr Gly
145                 150                 155                 160

Leu Ala Phe Leu Gly Ala Val Ile Trp Ala Ala Tyr Cys Thr Val Thr
                165                 170                 175

Ala Arg Leu Ala Lys Gly Lys Asn Gly Val Thr Leu Phe Phe Ile Leu
            180                 185                 190

Val Ala Leu Thr Leu Trp Val Lys Phe Phe Phe Gly Asp His Arg Pro
        195                 200                 205

Met Ser Phe Ser Leu Pro Ala Ile Val Tyr Leu Leu Leu Ala Ala Ala
    210                 215                 220
```

```
Ala Met Gly Phe Gly Tyr Ala Ala Trp Asn Val Gly Ile Leu His Gly
225                 230                 235                 240

Asn Val Thr Val Leu Ala Gly Val Ser Tyr Phe Ile Pro Val Phe Ser
                245                 250                 255

Ala Ala Leu Ser Ala Met Val Leu His Ala Pro Leu Pro Arg Ser Phe
            260                 265                 270

Trp Val Gly Ala Ser Leu Val Cys Ala Gly Ser Ile Leu Cys Trp Leu
        275                 280                 285

Ala Thr Arg Ala Arg Arg Ala Ser Ala Ala Gln Glu Asp Ala Val Ala
    290                 295                 300

Asp Cys Leu
305


<210> SEQ ID NO 146
<211> LENGTH: 307
<212> TYPE: PRT
<213> ORGANISM: Artificial Sequence
<220> FEATURE:
<223> OTHER INFORMATION: wex I83V

<400> SEQUENCE: 146

Met Asn Ser Lys Lys Ala Thr Leu Ile Gly Leu Thr Ala Val Val Leu
1               5                   10                  15

Trp Ser Ser Ile Val Gly Leu Ile Arg Gly Val Ser Glu His Leu Gly
            20                  25                  30

Ala Thr Gly Gly Ala Ala Met Met Tyr Ser Val Ala Ser Leu Phe Leu
        35                  40                  45

Leu Leu Ser Val Gly Phe Pro Lys Leu Gly Ser Phe Pro Lys Lys Tyr
    50                  55                  60

Leu Leu Trp Gly Ser Leu Leu Phe Val Ser Tyr Glu Leu Cys Leu Ser
65                  70                  75                  80

Leu Ser Val Gly Tyr Ala Asn Thr Gly Arg Gln Ala Ile Glu Val Ser
                85                  90                  95

Met Val Asn Tyr Leu Trp Pro Ala Phe Thr Leu Ile Ala Ala Ile Ala
            100                 105                 110

Phe Asn Arg Gln Arg Ala Asn Trp Met Val Val Pro Gly Phe Ile Leu
        115                 120                 125

Ser Ile Ile Gly Ile Cys Trp Val Leu Gly Gly Asp Gln Gly Leu Asp
    130                 135                 140

Leu Ala Gly Met Leu Gly Asn Val Gln Asp Asn Pro Leu Ser Tyr Gly
145                 150                 155                 160

Leu Ala Phe Leu Gly Ala Val Ile Trp Ala Ala Tyr Cys Thr Val Thr
                165                 170                 175

Ala Arg Leu Ala Lys Gly Lys Asn Gly Val Thr Leu Phe Phe Ile Leu
            180                 185                 190

Val Ala Leu Thr Leu Trp Val Lys Phe Phe Phe Gly Asp His Arg Pro
        195                 200                 205

Met Ser Phe Ser Leu Pro Ala Ile Val Tyr Leu Leu Leu Ala Ala Ala
    210                 215                 220

Ala Met Gly Phe Gly Tyr Ala Ala Trp Asn Val Gly Ile Leu His Gly
225                 230                 235                 240

Asn Val Thr Val Leu Ala Gly Val Ser Tyr Phe Ile Pro Val Phe Ser
                245                 250                 255

Ala Ala Leu Ser Ala Met Val Leu His Ala Pro Leu Pro Arg Ser Phe
            260                 265                 270
```

Trp Val Gly Ala Ser Leu Val Cys Ala Gly Ser Ile Leu Cys Trp Leu
275 280 285

Ala Thr Arg Ala Arg Arg Ala Ser Ala Ala Gln Glu Asp Ala Val Ala
290 295 300

Asp Cys Leu
305

<210> SEQ ID NO 147
<211> LENGTH: 307
<212> TYPE: PRT
<213> ORGANISM: Artificial Sequence
<220> FEATURE:
<223> OTHER INFORMATION: wex I83L

<400> SEQUENCE: 147

Met Asn Ser Lys Lys Ala Thr Leu Ile Gly Leu Thr Ala Val Val Leu
1 5 10 15

Trp Ser Ser Ile Val Gly Leu Ile Arg Gly Val Ser Glu His Leu Gly
20 25 30

Ala Thr Gly Gly Ala Ala Met Met Tyr Ser Val Ala Ser Leu Phe Leu
35 40 45

Leu Leu Ser Val Gly Phe Pro Lys Leu Gly Ser Phe Pro Lys Lys Tyr
50 55 60

Leu Leu Trp Gly Ser Leu Leu Phe Val Ser Tyr Glu Leu Cys Leu Ser
65 70 75 80

Leu Ser Leu Gly Tyr Ala Asn Thr Gly Arg Gln Ala Ile Glu Val Ser
85 90 95

Met Val Asn Tyr Leu Trp Pro Ala Phe Thr Leu Ile Ala Ala Ile Ala
100 105 110

Phe Asn Arg Gln Arg Ala Asn Trp Met Val Val Pro Gly Phe Ile Leu
115 120 125

Ser Ile Ile Gly Ile Cys Trp Val Leu Gly Gly Asp Gln Gly Leu Asp
130 135 140

Leu Ala Gly Met Leu Gly Asn Val Gln Asp Asn Pro Leu Ser Tyr Gly
145 150 155 160

Leu Ala Phe Leu Gly Ala Val Ile Trp Ala Ala Tyr Cys Thr Val Thr
165 170 175

Ala Arg Leu Ala Lys Gly Lys Asn Gly Val Thr Leu Phe Phe Ile Leu
180 185 190

Val Ala Leu Thr Leu Trp Val Lys Phe Phe Phe Gly Asp His Arg Pro
195 200 205

Met Ser Phe Ser Leu Pro Ala Ile Val Tyr Leu Leu Leu Ala Ala Ala
210 215 220

Ala Met Gly Phe Gly Tyr Ala Ala Trp Asn Val Gly Ile Leu His Gly
225 230 235 240

Asn Val Thr Val Leu Ala Gly Val Ser Tyr Phe Ile Pro Val Phe Ser
245 250 255

Ala Ala Leu Ser Ala Met Val Leu His Ala Pro Leu Pro Arg Ser Phe
260 265 270

-continued

```
Trp Val Gly Ala Ser Leu Val Cys Ala Gly Ser Ile Leu Cys Trp Leu
        275                 280                 285

Ala Thr Arg Ala Arg Arg Ala Ser Ala Ala Gln Glu Asp Ala Val Ala
    290                 295                 300

Asp Cys Leu
305
```

L-TRYPTOPHAN-EXPORTING PROTEIN VARIANT AND METHOD FOR PRODUCING L-TRYPTOPHAN USING THE SAME

SEQUENCE LISTING SUBMISSION VIA EFS-WEB

A computer readable text file, entitled "SequenceListing.txt" created on Feb. 22, 2021, with a file size of 100 kb contains the sequence listing for this application and is hereby incorporated by reference in its entirety.

TECHNICAL FIELD

The present disclosure relates to a novel protein variant having a tryptophan-exporting activity, an L-tryptophan-producing microorganism expressing the protein variant, and a method for producing L-tryptophan using the microorganism.

BACKGROUND ART

Tryptophan, which is an essential amino add, has been widely used as a raw material for feed additives, medicines (e.g., infusion solutions), health food materials, etc. At present, a direct fermentation method using a microorganism is mainly used for the production of L-tryptophan.

Previously, selective strains which exhibit resistance to analogues through chemical or physical mutation had mainly been used as the microorganism used for the production of L-tryptophan. However, as the rapid development of genetic recombination technology and the molecular-level regulatory mechanisms were identified in the 1990s, recombinant strains are mainly used by utilizing genetic engineering techniques.

Meanwhile, the expression of a gene exporting a particular amino add has contributed to an increase in productivity of the corresponding amino add in microorganisms. The enhancement of the expression of the L-lysine-exporting gene (lysE) in a microorganism of the genus *Corynebacterium* has improved the productivity of lysine (WO 9723597A2). Additionally, the enhancement of the rhtC gene in *E. coli* has improved the resistance to L-threonine, and simultaneously, has also improved the productivity of L-homoserine, L-threonine, and L-leucine (EP1013765A1). Additionally, Patent No. EP1016710B1 discloses that the productivity of L-glutamic add, L-lysine, L-threonine, L-alanine, L-histidine, L-proline, L-arginine, L-valine, and L-isoleucine was improved by the enhancement of yahN, yeaS, yfiK, and yggA genes, whose functions in *E. coli* have not yet been identified.

However, exporting proteins showing specificity to L-tryptophan has not been reported up to date. Although the yddG gene of *E. coli* is known, it shows higher specificity to L-phenylalanine than to L-tryptophan (*FEMS Microbiol Lett* 275 (2007), 312 to 318). Additionally, in a microorganism of the genus *Corynebacterium* which is mainly used as a producing strain for L-amino add fermentation, genes that export L-tryptophan or an aromatic amino add have never been reported (*J Ind Microbiol Biotechnol.* 2015 May; 42(5): 787 to 797).

DISCLOSURE

Technical Problem

The inventors of the present disclosure have succeeded in expressing a novel tryptophan-exporting protein having specificity to L-tryptophan in an L-tryptophan-producing microorganism, and as a result, they have discovered that the amount of L-tryptophan production was significantly improved. In addition, through the introduction of mutations to further improve the ability to export a corresponding membrane protein, they have confirmed that the amount of L-tryptophan production was significantly improved. Thereby, the present disclosure has been completed.

Technical Solution

An object of the present disclosure is to provide a protein variant having an L-tryptophan-exporting activity, in which at least one amino add selected from the amino adds corresponding to those at positions 79 to 83 in an amino add sequence of SEQ ID NO: 1 is substituted with a hydrophobic or aliphatic amino acid.

Another object of the present disclosure is to provide a polynucleotide encoding the variant; and a vector including the polynucleotide.

Still another object of the present disclosure is to provide an L-tryptophan-producing microorganism, which expresses the protein variant.

Still another object of the present disclosure is to provide a method for producing L-tryptophan, including culturing the microorganism in a medium.

Still another object of the present disclosure is to provide a use of the protein variant for increasing L-tryptophan production.

Advantageous Effects of the Invention

The inventors of the present disclosure have discovered a novel exporting gene having specificity to L-tryptophan and have attempted to express the gene in an L-tryptophan-producing microorganism. As a result, they have confirmed that the microorganism can significantly improve the amount of L-tryptophan production compared to its parent strain, in which the gene is not expressed, and have also discovered a protein variant encoded by the gene, which allows the microorganism to more significantly improve the amount of L-tryptophan production, thereby confirming that L-tryptophan can be effectively produced through the same.

BRIEF DESCRIPTION OF DRAWINGS

The FIGURE shows the intracellular concentrations of tryptophan in CA04-8352 and CA04-8405, which are modified strains of *Corynebacterium glutamicum*, according to glucose consumption.

DETAILED DESCRIPTION OF THE INVENTION

Hereinafter, the present disclosure will be described in more detail. Meanwhile, each description and embodiment disclosed in the present disclosure may be applied herein to describe each of different descriptions and embodiments. In other words, all combinations of various components disclosed in the present disclosure are included within the scope of the present disclosure. Further, the scope of the present disclosure should not be limited by the detailed description provided below.

An aspect of the present disclosure provides a protein variant having an L-tryptophan-exporting ability, in which the protein variant includes at least one mutation in an amino acid sequence of SEQ ID NO: 1.

The mutation may include those in which at least one amino acid selected from the $79^{th}$ amino acid to the $83^{rd}$ amino acid from the N-terminus of the amino add sequence of SEQ ID NO: 1 is substituted with a different amino add.

The protein variant may be a protein variant having an L-tryptophan-exporting activity, in which at least one amino add selected from the amino acids at positions 79 to 83 in an amino acid sequence of SEQ ID NO: 1 is substituted with a different amino add. Specifically, the protein variant may be a protein variant having an L-tryptophan-exporting activity, in which at least one amino add selected from the amino adds at positions 79 to 83 in an amino add sequence of SEQ ID NO: 1 is substituted with a hydrophobic amino add or aliphatic amino acid.

As used herein, the term "L-tryptophan", which is one of a-amino acids, refers to an essential amino add that is not synthesized in vivo and is an aromatic L-amino acid having a chemical formula of $C_{11}H_{12}N_2O_2$.

In the present disclosure, "protein having an L-tryptophan-exporting ability" or "protein having an L-tryptophan-exporting activity" refers to a membrane protein which has an activity of specifically exporting L-tryptophan outside a cell.

The protein having an L-tryptophan-exporting activity may be a *Herbaspirillum rhizosphaerae*-derived protein having an L-tryptophan-exporting activity. The *Herbaspirillum rhizosphaerae*-derived protein having an L-tryptophan-exporting activity may be, for example, a protein including an amino add sequence of SEQ ID NO: 1. The protein including an amino acid sequence of SEQ ID NO: 1 may be used interchangeably with a protein having an amino acid sequence of SEQ ID NO: 1 and a protein consisting of an amino acid sequence of SEQ ID NO: 1.

In particular, "*Herbaspirillum rhizosphaerae*" is a gram negative bacterium belonging to the genus *Herbaspirillum*. In Korea, *Herbaspirillum rhizosphaerae*, as a strain isolated from Ulleung island, etc., can be isolated from the rhizosphere in the soil.

Additionally, although the protein of the present disclosure, which has an L-tryptophan-exporting activity, was defined as a protein including the amino acid sequence of SEQ ID NO: 1, it does not exclude an addition of a meaningless sequence upstream or downstream of the amino acid sequence of SEQ ID NO: 1, a mutation that may occur naturally, or a silent mutation thereof, and it is apparent to those skilled in the art that any protein, which has an activity identical or corresponding to the protein including the amino add sequence of SEQ ID NO: 1, belongs to the protein of the present disclosure, which has an L-tryptophan-exporting activity. Specifically, for example, the protein of the present disclosure, which has an L-tryptophan-exporting activity, may be a protein consisting of the amino acid sequence of SEQ ID NO: 1, or a protein consisting of an amino acid sequence having a homology or identity to the amino add sequence of SEQ ID NO: 1 of 80%, 90%, 95%, 97%, or higher. Additionally, it is apparent that any protein having an amino add sequence with deletion, modification, substitution, or addition in part of the sequence can also belong to the scope of the proteins of the present disclosure to be mutated, as long as the protein has an amino add sequence with any of the above homologies or identities and exhibits an effect corresponding to the above protein.

That is, in the present disclosure, even in a case where it is described as "protein or polypeptide having an amino add sequence of a particular SEQ ID NO" or "protein or polypeptide consisting of an amino add sequence of a particular SEQ ID NO", it is apparent that any protein having an amino add sequence with deletion, modification, substitution, or addition in part of the sequence can also be used in the present disclosure, as long as the protein has an activity identical or corresponding to that of the polypeptide consisting of the amino acid sequence of the corresponding SEQ ID NO. For example, it is apparent that the "polypeptide consisting of the amino add sequence of SEQ ID NO: 1" can also belong to the "polypeptide consisting of the amino add sequence of SEQ ID NO: 1", as long as the polypeptide has an activity identical or corresponding thereto.

The protein variant having an L-tryptophan-exporting ability provided in the present disclosure may refer to a variant in which, among the proteins having the L-tryptophan protein exporting ability described above, an amino add at a specific position thereof is substituted and the resulting L-tryptophan-exporting ability exceeds 100% compared to that of the protein before mutation.

As used herein, the term "variant" refers to a protein, in which at least one amino add in the conservative substitution and/or modification is different from that of the recited sequence, but the functions or properties of the protein are maintained. A variant differs from the sequence identified by several amino acid substitutions, deletions, or additions. Such a variant can be identified by modifying one or more amino adds in the amino add sequence of the protein above and by evaluating the properties of the modified protein above. That is, the ability of a variant may be increased, unchanged, or reduced compared to that of its native protein. Additionally, some variants may include those in which one or more parts (e.g., an N-terminal leader sequence or a transmembrane domain) are removed. Other variants may include variants in which part of the N-terminus and/or C-terminus of a mature protein is removed. The term "variant" may also be used interchangeably with "modification", "modified protein", "modified polypeptide", "mutant", "mutein", "divergent", "variant", etc., but the term to be used is not limited thereto and any term may be used, as long as it is used in a sense of being mutated. For the purpose of the present disclosure, the variant may refer to those in which the activity of a mutated protein is increased compared to that of natural wild-type or unmodified proteins, but the variant is not limited thereto.

As used herein, the term "conservative substitution" refers to substitution of one amino add with a different amino add that has similar structural and/or chemical properties. The variant may have, for example, one or more conservative substitutions while still retaining one or more biological activities. Such amino acid substitutions may generally occur based on similarity in polarity, charge, solubility, hydrophobicity, hydrophilicity, and/or amphipathic nature of residues. For example, among the electrically charged amino acids, positively-charged (basic) amino adds include arginine, lysine, and histidine; negatively-charged (acidic) amino adds include glutamic add and aspartic add. Among the uncharged amino adds, nonpolar amino acids include glycine, alanine, valine, leucine, isoleucine, methionine, phenylalanine, tryptophan, and proline; polar or hydrophilic amino adds include serine, threonine, cysteine, tyrosine, asparagine, and glutamine; and aromatic amino adds include phenylalanine, tryptophan, and tyrosine.

Further, a variant may include deletion or addition of amino adds that have a minimal influence on properties and a secondary structure of a polypeptide. For example, a polypeptide may be conjugated to a signal (or leader) sequence at the N-terminus of a protein, which co-translationally or post-translationally directs transfer of the protein. In addition, the polypeptide may also be conjugated to another sequence or a linker for identification, purification, or synthesis of the polypeptide.

The "substitution with a different amino add" is not limited as long as the substituted amino add is different from that before substitution. That is, the "substitution with a different amino add" is not limited as long as the $79^{th}$ amino acid from the N-terminus of an amino add sequence of SEQ ID NO: 1 (i.e., leucine) is substituted with an amino add other than leucine; the $80^{th}$ amino acid from the N-terminus of an amino add sequence of SEQ ID NO: 1 (i.e., serine) is substituted with an amino acid other than serine; the $81^{st}$ amino add from the N-terminus of an amino add sequence of SEQ ID NO: 1 (i.e., leucine) is substituted with an amino acid other than leucine; the $82^{nd}$ amino add from the N-terminus of an amino add sequence of SEQ ID NO: 1 (i.e., serine) is substituted with an amino add other than serine; or the $83^{rd}$ amino acid from the N-terminus of an amino acid sequence of SEQ ID NO: 1 (i.e., isoleucine) is substituted with an amino add other than isoleucine. Meanwhile, when it is expressed as "a particular amino add is substituted" in the present disclosure, it is obvious that the amino add is substituted with an amino add different from the amino add before the substitution, even if it is not specifically stated that the amino add has been substituted with a different amino acid.

Alternatively, the protein variant may be a variant, in which at least one amino add among the amino acids at positions 79 to 83 in an amino add sequence of SEQ ID NO: 1 is substituted with an amino add other than the amino add before substitution, excluding acidic amino adds and basic amino acids. Alternatively, the protein variant may be a variant having an uncharged amino add, in which the substituted amino add is different from the amino acid before substitution, but the protein variant is not limited thereto.

Alternatively, the protein variant may be a variant, in which at least one amino add among the amino acids at positions 79 to 83 in an amino add sequence of SEQ ID NO: 1 is substituted with an amino add between a hydrophobic amino add and an aliphatic amino acid that is different from the amino add before substitution. Specifically, the protein variant may be a variant, in which at least one amino add among the amino adds at positions 79 to 83 in an amino add sequence of SEQ ID NO: 1 is substituted with any one amino add between a hydrophobic (nonpolar) amino add and an aliphatic amino add. The aliphatic amino add may be, for example, an amino add selected from the group consisting of glycine, alanine, valine, leucine, and isoleucine, but the aliphatic amino add is not limited thereto. The hydrophobic (nonpolar) amino acid may be, for example, an amino add selected from the group consisting of glycine, methionine, alanine, valine, leucine, isoleucine, proline, phenylalanine, tyrosine, and tryptophan, but the hydrophobic (nonpolar) amino add is not limited thereto.

Alternatively, the protein variant may be a variant, in which at least one amino add among the amino acids at positions 79 to 83 in an amino add sequence of SEQ ID NO: 1 is substituted with an amino acid different from the amino add before substitution, among small-sized amino adds, but the protein variant is not limited thereto.

As used herein, the term "small-sized amino acids" includes amino adds with a relatively small size among the 20 amino adds (i.e., glycine, alanine, serine, threonine, cysteine, valine, leucine, isoleucine, proline, and asparagine), and specifically, may refer to glycine, alanine, serine, threonine, cysteine, valine, leucine, isoleucine, and proline, but the small-sized amino acids are not limited thereto; and more specifically, the small-sized amino adds may refer to glycine, alanine, valine, leucine, isoleucine, serine, and threonine, but the small-sized amino adds are not limited thereto.

Alternatively, the protein variant may be a variant, in which at least one amino add among the amino acids at positions 79 to 83 in an amino add sequence of SEQ ID NO: 1 is substituted with an amino acid selected from the group consisting of alanine, valine, leucine, and isoleucine, but the protein variant is not limited thereto.

Specifically, the substitution with a different amino add in the protein variant may be one or more substitutions selected from the substitutions, which consists of: a substitution in which the $79^{th}$ amino add in the amino acid sequence of SEQ ID NO: 1 (i.e., leucine) is substituted with alanine, valine, or isoleucine; a substitution in which the $80^{th}$ amino add in the amino acid sequence of SEQ ID NO: 1 (i.e., serine) is substituted with alanine, valine, leucine, or isoleucine; a substitution in which the $81^{st}$ amino add in the amino add sequence of SEQ ID NO: 1 (i.e., leucine) is substituted with alanine, valine, or isoleucine; a substitution in which the $82^{nd}$ amino add in the amino add sequence of SEQ ID NO: 1 (i.e., serine) is substituted with alanine, valine, leucine, or isoleucine; and a substitution in which the $83^{rd}$ amino acid in the amino add sequence of SEQ ID NO: 1 (i.e., isoleucine) is substituted with alanine, valine, or leucine, but the substitution is not limited thereto.

The protein variants of the present disclosure, as such, have an enhanced L-tryptophan-exporting ability compared to the protein before mutation.

It is obvious that the protein variants of the present disclosure, in which at least one amino add among the amino adds at positions 79 to 83 from the N-terminus of SEQ ID NO: 1 is substituted with a different amino add, include protein variants in which the amino adds at positions corresponding to the positions of 79 to 83 are substituted with a different amino add.

One of ordinary skill in the art will be able to identify whether or not an amino add at any position in any sequence is an amino add corresponding to the amino acids at positions 79 to 83 of SEQ ID NO: 1, by comparing any sequence with the SEQ ID NO: 1 of the present disclosure by applying a method of confirming sequence alignment, homology, or identity known in the art.

Therefore, although not otherwise described herein, it is obvious that the description relating to the "amino adds at positions 79 to 83 of SEQ ID NO: 1" can also be applied to the description of the "amino acids corresponding to the amino acids at positions 79 to 83 of SEQ ID NO: 1" in any sequence, for example, a sequence having the identity to the SEQ ID NO: 1 of 50%, 60%, 70%, 80%, or 90% or higher.

For example, the protein variant of the present disclosure may be a protein variant in which an amino acid corresponding to the amino adds at positions 79 to 83 is substituted with a different amino add and has the identity to the SEQ ID NO: 1 of 70%, 80%, 90%, or 95%, but the protein variant of the present disclosure is not limited thereto.

The protein variant, in which one or more amino adds among the amino acids at positions 79 to 83 in an amino add sequence of SEQ ID NO: 1 are substituted with a different amino acid, may be a protein variant which includes any one amino add sequence among the SEQ ID NOS: 131 to 147; specifically, may be a protein variant which consists essentially of any one amino add sequence among the SEQ ID NOS: 131 to 147; and more specifically, may be a protein variant which consists of any one amino acid sequence among the SEQ ID NOS: 131 to 147, but the protein variant of the present disclosure is not limited thereto.

Additionally, the protein variant may include any one amino add sequence among the SEQ ID NOS: 131 to 147; or an amino add sequence, in which at least one amino add selected from the amino acids at positions 79 to 83 in an amino acid sequence of SEQ ID NO: 1 is fixed and which has a homology or identity to SEQ ID NO: 1 of 80% or higher, but the protein variant is not limited thereto. Specifically, the mutant polypeptide of the present disclosure may include a polypeptide which has a homology or identity to any one amino add sequence of SEQ ID NOS: 131 to 147 of at least 80%, 90%, 95%, 96%, 97%, 98%, or 99%. Additionally, it is apparent that any protein, which has an amino add sequence with deletion, modification, substitution, or addition in part of the sequence other than the amino add positions of 79 to 83, can also be included within the scope of the present disclosure, as long as the protein has any of the above homologies or identities and exhibits an effect corresponding to the protein above.

As used herein, the term "homology" or "identity" refers to a degree of relevance between two given amino add sequences or nucleotide sequences and it may be expressed as a percentage. These terms "homology" and "identity" may often be used interchangeably.

Sequence homology or identity of conserved polynucleotides or polypeptides can be determined by standard alignment algorithm, and default gap penalties established by a program being used may be used together. Actually, homologous or identical sequences may hybridize to each other along at least about 50%, 60%, 70%, 80%, or 90% of the entire sequence or the entire length under moderate or highly stringent conditions. In hybridization, polynucleotides including a degenerate codon instead of a codon are also considered.

Whether any two polynucleotide- or polypeptide sequences have a homology, similarity, or identity may be determined using computer algorithms known in the art, e.g., "FASTA" program using default parameters introduced by Pearson et al. (1988) [*Proc. Natl. Acad. Sci. USA* 85: 2444]. Alternatively, Needleman-Wunsch algorithm (1970, *J. Mol. Biol.* 48: 443-453) performed in a Needleman program of The European Molecular Biology Open Software Suite of EMBOSS package (Rice et al., 2000, *Trends Genet.* 16: 276-277) (version 5.0.0 or a later version) may be used to determine the same (including GCG program package (Devereux, J., et al., *Nucleic Acids Research* 12: 387 (1984)), BLASTP, BLASTN, FASTA (Atschul, [S.] [F.,] [ET AL., *J MOLEC BIOL* 215]: 403 (1990); Guide to Huge Computers, Martin J. Bishop, [ED.,] Academic Press, San Diego, 1994, and [CARILLO ETA/.](1988) SIAM *J Applied Math* 48: 1073). For example, the homology, similarity, or identity may be determined using BLAST from the National Center for Biotechnology Information database or ClustalW.

The homology, similarity, or identity between polynucleotides or polypeptides, for example, may be determined by comparing the given sequence information using a GAP computer program, such as a program introduced by Needleman et al. (*J Mol Biol.* 48: 443 (1970)) as disclosed by Smith and Waterman (*Adv. Appl. Math* (1981) 2: 482). In brief, the GAP program defines homology, similarity, or identity as the number of similar aligned symbols (i.e., nucleotides or amino adds) divided by the total number of the symbols in a shorter of the two sequences. The default parameters for the GAP program may include: (1) a binary comparison matrix (including a value 1 for identity and a value 0 for non-identity) and the weighted comparison matrix of Gribskov, et al., (*Nucl. Acids Res.* 14: 6745 (1986)) as described by Schwartz and Dayhoff, eds. (Atlas Of Protein Sequence And Structure, National Biomedical Research Foundation, pp. 353-358 (1979) or EDNAFULL (EMBOSS version of NCBI NUC4.4) substitution matrix); (2) a penalty of 3.0 for each gap and an additional 0.10 penalty for each symbol in each gap (or a gap open penalty of 10 and a gap extension penalty of 0.5); and (3) no penalty for end gaps.

Additionally, whether any two polynucleotide- or polypeptide sequences have a homology, similarity, or identity may be confirmed by comparing these sequences by southern hybridization experiments to be performed under defined strict conditions, and the appropriate hybridization conditions to be defined may be determined within the scope of the art and by a method well known to those skilled in the art (e.g., J. Sambrook et al., *Molecular Cloning, A Laboratory Manual,* 2nd Edition, Cold Spring Harbor Laboratory press, Cold Spring Harbor, N.Y., 1989; F. M. Ausubel et al., *Current Protocols in Molecular Biology*, John Wiley & Sons, Inc., New York).

As used herein, the term "to be expressed/expressing" with regard to a protein refers to a state in which a target protein is introduced into a microorganism or a target protein is modified to be expressed in a microorganism. When the target protein is a protein present in a microorganism, the term refers to a state in which the activity of the protein is enhanced compared to the activity of its endogenous protein or that before its modification. For the purpose of the present disclosure, "target protein" may be a variant of the protein having an L-tryptophan-exporting ability described above.

Specifically, the term "introduction of a protein" means that a microorganism exhibits an activity of a particular protein which was not originally possessed therein, or the microorganism exhibits enhanced activity compared to its endogenous activity or the activity of the protein before modification. For example, the term "introduction of a protein" may mean that a polynucleotide encoding a particular protein is introduced into the chromosome of a microorganism; or a vector including a polynucleotide encoding a particular protein is introduced into a microorganism and thereby allows the activity of the particular protein to be exhibited. Additionally, the term "enhancement of activity" means that the activity of a particular protein is enhanced compared to its endogenous activity or the activity before its modification. The term "endogenous activity" refers to the activity of a particular protein originally possessed by a parent strain before modification, in a case where the trait of the microorganism is altered due to genetic mutation caused by a natural or artificial factor.

Specifically, in the present disclosure, the enhancement of an activity may be achieved by one or more methods selected from the group, which consists of: a method for increasing the intracellular copy number of a gene encoding the protein variant; a method for introducing a mutation to the expression control sequence of a gene encoding the protein variant; a method for replacing the expression control sequence of a gene encoding the protein variant having an L-tryptophan-exporting activity with a sequence having a strong activity; a method for replacing a gene encoding a native protein having an L-tryptophan-exporting activity on the chromosome with a gene encoding the protein variant; a method for further introducing a mutation to a gene encoding the protein having an L-tryptophan-exporting activity such that the activity of the protein variant is enhanced; and a method for introducing a protein variant into a microorganism, but the method for enhancing an activity is not limited thereto.

In the above, the method for increasing the copy number of a gene may be performed in a form where the gene is operably linked to a vector or by inserting the gene into the chromosome of a host cell, but the method is not particularly limited thereto. Specifically, the copy number of a gene may be increased by introducing a vector into a host cell, where the vector, to which a polynucleotide encoding the protein of the present disclosure is operably linked and which can replicate and function regardless of the host cell, is introduced into the host cell. Alternatively, the copy number of a gene may be increased by introducing the vector, to which a polynucleotide is operably linked and which can insert the polynucleotide into the chromosome of a host cell, into the chromosome of the host cell. The insertion of a polynucleotide into the chromosome may be achieved by a method known in the art (e.g., homologous recombination).

Then, the modification of the expression control sequence for increasing the expression of a polynucleotide may be performed by inducing a mutation in the sequence of a nucleic add by deletion, insertion, non-conservative or conservative substitution, or a combination thereof so as to further enhance the activity of the expression control sequence; or by replacing the expression control sequence with a nucleic acid sequence with a stronger activity, but the method of modification of the expression control sequence is not particularly limited thereto. The expression control sequence may include a promoter, an operator sequence, a sequence encoding a ribosome-binding site, sequences controlling the termination of transcription and translation, etc., but the expression control sequence is not particularly limited thereto.

A strong promoter may be linked to an upstream region of the expression unit of the polynucleotide instead of the original promoter, but is not limited thereto. Examples of the strong promoter known in the art may include cj1 to cj7 promoters (KR Patent No. 10-0620092), a lac promoter, a trp promoter, a trc promoter, a tac promoter, a lambda phage PR promoter, a $P_L$ promoter, a tet promoter, a gapA promoter, a SPL7 promoter, SPL13 (sm3) promoter (KR Patent No. 10-1783170), an O2 promoter (KR Patent No. 10-1632642), a tkt promoter, a yccA promoter, etc., but the strong promoter is not limited thereto.

Further, the modification of a polynucleotide sequence on the chromosome may be performed by inducing a mutation on the expression control sequence by deletion, insertion, non-conservative or conservative substitution, or a combination thereof so as to further enhance the activity of the polynucleotide sequence; or by replacing the polynucleotide sequence with a polynucleotide sequence improved to have a stronger activity, but the modification method of the polynucleotide sequence is not particularly limited thereto.

The introduction and enhancement of a protein activity as described above may generally increase the activity or concentration of the corresponding protein by at least 1%, at least 10%, at least 25%, at least 50%, at least 75%, at least 100%, at least 150%, at least 200%, at least 300%, at least 400%, or at least 500%, and at most 1,000% or 2,000%, based on the activity or concentration of the protein in a wild-type or unmodified microorganism strain, but the range of increase is not limited thereto.

Another aspect of the present disclosure provides a polynucleotide which encodes the protein variant above.

As used herein, the term "polynucleotide" refers to a DNA or RNA strand having more than a certain length as a nucleotide polymer, which is a long chain of nucleotide monomers connected by a covalent bond, and more specifically, refers to a polynucleotide fragment encoding the protein variant.

The polynucleotide encoding the protein variant of the present disclosure may include any polynucleotide sequence without limitation as long as the polynucleotide sequence encodes a protein variant having an L-tryptophan-exporting ability.

In the present disclosure, the gene encoding the amino acid sequence of the protein having an L-tryptophan-exporting ability may be a wex gene, may be derived from *Herbaspirillum rhizosphaerae*, specifically, may be a nucleotide sequence encoding the amino acid sequence of SEQ ID NO: 1, and more specifically, may be a nucleotide sequence including the nucleotide sequence of SEQ ID NO: 2, but the gene is not limited thereto.

Considering codon degeneracy and the codons preferred in a bioorganism where the polypeptide is to be expressed, various modifications may be performed in the coding region of the polynucleotide encoding the protein variant of the present disclosure within the scope not altering the amino acid sequence of the polypeptide. Specifically, any polynucleotide sequence encoding a protein variant, in which at least one amino add selected from the amino adds at positions 79 to 83 in an amino acid sequence of SEQ ID NO: 1 is substituted with a different amino acid, may be included without limitation. For example, the polynucleotide of the present disclosure may be the protein variant of the present disclosure, and specifically a polynucleotide sequence encoding a protein, which includes an amino add sequence of any one of the SEQ ID NOS: 131 to 147, or a polypeptide having a homology or identity to the protein, but the polynucleotide of the present disclosure is not limited thereto, and more specifically, may be one which includes any one polynucleotide sequence among the polynucleotide sequences of SEQ ID NOS: 80, 81, 82, 89, 90, 91, 92, 101, 102, 103, 110, 111, 112, 113, 122, 123, and 124, but the polynucleotide of the present disclosure is not limited thereto. The homology and identity are the same as described above.

Additionally, any sequence which encodes a protein variant, in which at least one amino add selected from the amino adds at positions 79 to 83 in an amino acid sequence of SEQ ID NO: 1 is substituted with a different amino add, by hybridizing with any probe that can be prepared from known gene sequences (e.g., complementary sequences to all or part of the above polynucleotide sequence) under stringent conditions, may be included without limitation.

The term "stringent conditions" refers to conditions which enables specific hybridization between polynucleotides. Such conditions are specifically described in references (e.g., J Sambrook et al., supra). For example, the conditions may include performing hybridization between genes having a high homology, a homology of 40% or higher, specifically 90% or higher, more specifically 95% or higher, even more specifically 97% or higher, and most specifically 99% or higher, while not performing hybridization between genes having a homology of lower than the homologies described above; or performing conventional washing conditions for southern hybridization, i.e., washing once, specifically, twice or three times at a salt concentration and temperature corresponding to 60° C., 1×SSC, and 0.1% SDS, specifically 60° C., 0.1×SSC, and 0.1% SDS, and more specifically 68° C., 0.1×SSC, and 0.1% SDS. However, hybridization conditions are not limited thereto, but may be appropriately adjusted by those skilled in the art according to the purpose.

Hybridization requires that two polynucleotides include complementary sequences, although mismatches between bases are possible depending on the stringency of the hybridization. The term "complementary" is used to describe the relationship between mutually-hybridizable nucleotide bases. For example, with respect to DNA, adenosine is complementary to thymine, and cytosine is complementary to guanine. Accordingly, the present disclosure may also include isolated polynucleotide fragments complementary to the entire sequence as well as substantially similar polynucleotide sequences.

Specifically, polynucleotides having a homology can be detected at a $T_m$ value of 55° C. using hybridization conditions that include a hybridization step and using the conditions described above. Additionally, the $T_m$ value may be 60° C., 63° C., or 65° C., but the temperature is not limited thereto and may be appropriately adjusted by those skilled in the art according to the purpose.

The stringency suitable for the hybridization of polynucleotides depends on the length and degree of complementarity of the polynucleotides, and the variables are well known in the art (see Sambrook et al., supra, 9.50 to 9.51 and 11.7 to 11.8).

Still another aspect of the present disclosure provides a vector which includes a polynucleotide encoding the protein variant.

As used herein, the term "vector" refers to a DNA construct including a nucleotide sequence of a polynucleotide encoding a target protein, which is operably linked to a suitable control sequence so that the target protein can be expressed in a suitable host. The control sequence includes a promoter capable of initiating transcription, any operator sequence for controlling the transcription, a sequence encoding an appropriate mRNA ribosome-binding site, and a sequence for controlling the termination of transcription and translation. The vector, after being transformed into a suitable host cell, may be replicated or function irrespective of the host genome, or may be integrated into the host genome itself.

The vector used in the present disclosure is not particularly limited, but any vector known in the art may be used. Examples of vectors conventionally used may include a natural or recombinant plasmid, cosmid, virus, and bacteriophage. For example, pWE15, M13, MBL3, MBL4, IXII, ASHII, APII, t10, t11, Charon4A, Charon21A, etc. may be used as a phage vector or cosmid vector, and those based on pBR, pUC, pBluescriptII, pGEM, pTZ, pCL, pET, etc. may be used as a plasmid vector. Specifically, vectors such as pDZ, pACYC177, pACYC184, pCL, pECCG117, pUC19, pBR322, pMW118, pCC1BAC, etc. may be used.

For example, the polynucleotide encoding a target protein in the chromosome may be replaced with a mutated polynucleotide through a vector for intracellular chromosomal insertion. The insertion of a polynucleotide into the chromosome may be performed using any method known in the art (e.g., homologous recombination), but the method is not limited thereto. The vector may further include a selection marker for confirming its successful insertion into the chromosome. A selection marker is used for selection of cells transformed with the vector, i.e., to confirm whether the target nucleic add molecule has been successfully inserted, and markers which confer selectable phenotypes (e.g., drug resistance, auxotrophy, resistance to cytotoxic agents, expression of surface proteins, etc.) may be used. Under the circumstances where selective agents are treated, only the cells capable of expressing the selection markers can survive or express other phenotypic traits, thereby enabling easy selection of the transformed cells.

Still another object of the present disclosure is to provide an L-tryptophan-producing microorganism, which expresses the protein variant having an L-tryptophan-exporting activity.

As used herein, the term, "L-tryptophan-producing microorganism" refers to a microorganism which can produce L-tryptophan from carbon sources in a medium in an excess amount compared to that of a wild-type or unmodified microorganism.

Additionally, the L-tryptophan-producing microorganism may be a recombinant microorganism. Specifically, the microorganism may be a microorganism of the genus *Enterobacter*, a microorganism of the genus *Escherichia*, a microorganism of the genus *Erwinia*, a microorganism of the genus *Serratia*, a microorganism of the genus *Providencia*, a microorganism of the genus *Corynebacterium*, or a microorganism of the genus *Brevibacterium*, but the type of the microorganism is not particularly limited as long as the microorganism can produce L-tryptophan. More specifically, the microorganism may be a microorganism of the genus *Corynebacterium* or a microorganism of the genus *Escherichia*.

Even more specifically, the microorganism of the genus *Escherichia* may be *Escherichia coli* and the microorganism of the genus *Corynebacterium* may be *Corynebacterium glutamicum*, but any microorganism of the genus *Escherichia* or the genus *Corynebacterium*, in which a protein having an L-tryptophan-exporting activity is introduced or the activity is enhanced and thus the amount of L-tryptophan production can be increased, can be included without limitation.

In the microorganisms described above, the amount of L-tryptophan production may be increased using a method of increasing L-tryptophan biosynthesis by enhancing the expression of a tktA gene or by blocking branched pathways in the L-tryptophan biosynthesis pathway for continuous supply of precursors (e.g., erythrose-4-phosphate; E4P) and efficient energy utilization, or using a method of utilizing a lesser amount of ATP, etc.

Specifically, in the present disclosure, the parent strain of the L-tryptophan-producing microorganism, which expresses the protein or protein variant having an L-tryptophan-exporting activity or which is modified so that the protein or protein variant having an L-tryptophan-exporting activity can be expressed, is not particularly limited as long as the parent strain is an L-tryptophan-producing microorganism. The L-tryptophan-producing microorganism may be a microorganism in which the activity of a gene in a competitive pathway, a regulator in a directional pathway of an L-tryptophan operon, a gene for importing L-tryptophan, or a gene for importing and decomposing L-tryptophan is weakened or inactivated, so as to enhance the L-tryptophan biosynthesis pathway; and/or may be a microorganism in which the activity of an L-tryptophan operon is overexpressed. Specifically, the activity of trpR (i.e., a gene for regulating an enzyme group of tryptophan synthesis, which inhibits the expression of L-tryptophan biosynthesis genes (trpEDCBA)) or the activity of Mtr (i.e., a membrane protein that imports extracellular L-tryptophan into a cell) may be weakened or removed compared to their endogenous activity.

To achieve the above object, still another aspect of the present disclosure provides a method for producing tryptophan, which includes culturing an L-tryptophan-producing microorganism expressing the protein variant in a medium.

The L-tryptophan, the protein which has an L-tryptophan-exporting activity and includes the amino add sequence of SEQ ID NO: 1, the expression of the protein and the microorganism are the same as described above.

As used herein, the term "culture" means that the microorganism is grown under appropriately controlled environmental conditions. The culture process of the present disclosure can be performed in a suitable culture medium and culture conditions known in the art. Such a culture process may be easily adjusted for use by those skilled in the art according to the strain to be selected. Specifically, the culture process may be performed in batch culture, continuous culture, and fed-batch culture known in the art, but the culture process is not limited thereto.

As used herein, the term "medium" refers to a mixture of materials which contains nutrient materials required for the culture of the microorganism as a main ingredient, and it supplies nutrient materials, growth factors, etc. along with material that is essential for survival and growth. Specifically, as the medium and other culture conditions used for culturing the microorganism of the present disclosure, any medium used for conventional culture of microorganisms may be used without particular limitation. However, the microorganism of the present disclosure may be cultured under aerobic conditions in a conventional medium containing an appropriate carbon source, nitrogen source, phosphorus source, inorganic compound, amino add, and/or vitamin, etc while adjusting temperature, pH, etc.

In the present disclosure, the carbon source may include carbohydrates (e.g., glucose, fructose, sucrose, maltose, etc.); sugar alcohols (e.g., mannitol, sorbitol, etc.); organic acids (e.g., pyruvic add, lactic add, citric add, etc.); amino acids (e.g., glutamic acid, methionine, lysine, etc.), etc. Additionally, the carbon source may include natural organic nutrients (e.g., starch hydrolysate, molasses, blackstrap molasses, rice bran, cassava, sugar cane molasses, corn steep liquor, etc.). Specifically, carbohydrates such as glucose and sterilized pretreated molasses (i.e., molasses converted to reducing sugar) may be used, and in addition, various other carbon sources in an appropriate amount may be used without limitation. These carbon sources may be used alone or in a combination of two or more kinds, but the carbon sources are not limited thereto.

Examples of the nitrogen source may include inorganic nitrogen sources (e.g., ammonia, ammonium sulfate, ammonium chloride, ammonium acetate, ammonium phosphate, ammonium carbonate, ammonium nitrate, etc.); amino adds (e.g., glutamic add, methionine, glutamine, etc.); and organic nitrogen sources (e.g., peptone, N-Z amine, a meat extract, an yeast extract, a malt extract, corn steep liquor, a casein hydrolysate, fish or a decomposition product thereof, defatted soybean cake or a decomposition product thereof, etc.). These nitrogen sources may be used alone or in a combination of two or more kinds, but the nitrogen sources are not limited thereto.

Examples of the phosphorus source may include potassium dihydrogen phosphate, dipotassium hydrogen phosphate, corresponding sodium-containing salts, etc. Examples of the inorganic compound may include sodium chloride, calcium chloride, iron chloride, magnesium sulfate, iron sulfate, manganese sulfate, calcium carbonate, etc. Additionally, in addition thereto, amino adds, vitamins, and/or appropriate precursors may be included. These constituting ingredients or precursors may be added to a medium in batch culture or continuous culture, but are not limited thereto.

In the present disclosure, the pH of a medium may be adjusted during the culture of a microorganism by adding a compound (e.g., ammonium hydroxide, potassium hydroxide, ammonia, phosphoric add, sulfuric add, etc.) to the medium in an appropriate manner. Additionally, during the culture, an antifoaming agent (e.g., fatty add polyglycol ester) may be added to prevent foam generation. Additionally, oxygen or oxygen-containing gas may be injected into the medium in order to maintain an aerobic state of the medium; or nitrogen, hydrogen, or carbon dioxide gas may be injected into the medium without gas injection in order to maintain an anaerobic or microaerobic state of the medium, but the gas is not limited thereto.

The medium temperature may be in a range from 20° C. to 50° C., and specifically in a range from 30° C. to 37° C., but the medium temperature is not limited thereto. The culture may be continued until useful materials are obtained in desired amounts, and specifically for 10 hours to 100 hours, but the culture period is not limited thereto.

The production method may include recovering L-tryptophan from the cultured medium or the microorganism.

In the step of recovering tryptophan, the desired L-tryptophan may be recovered from the medium using the method of the present disclosure for culturing a microorganism, for example, using a suitable method known in the art according to a batch culture process, continuous culture process, or fed-batch culture process. For example, methods such as centrifugation, filtration, treatment with a protein crystallization precipitant (salting-out method), extraction, ultrasonic disruption, ultrafiltration, dialysis, various kinds of chromatographies (e.g., molecular sieve chromatography (gel filtration), adsorption chromatography, ion-exchange chromatography, affinity chromatography, etc.), and HPLC may be used alone or in combination, but the methods are not limited thereto.

The production method may include a purification process. In the purification process, the recovered L-tryptophan can be purified using an appropriate purification method known in the art.

Still another aspect of the present disclosure provides a method for increasing the L-tryptophan-exporting ability of a microorganism, which includes modifying the microorganism so that a protein variant having an L-tryptophan-exporting activity, in which at least one amino add selected from the amino adds at positions 79 to 83 in an amino add sequence of SEQ ID NO: 1 is substituted with a different amino acid, can be expressed in the microorganism.

Still another aspect of the present disclosure provides a use of the protein variant for increasing an L-tryptophan-exporting ability.

Still another aspect of the present disclosure provides a use of the protein variant for increasing an L-tryptophan-producing ability.

Since the protein variant of the present disclosure can increase the L-tryptophan-exporting ability of a microorganism, it can be used for increasing the production of L-tryptophan. The protein variant and other amino adds are the same as described above.

DETAILED DESCRIPTION OF THE INVENTION

Hereinafter, the present disclosure will be described in detail through exemplary embodiments. However, these exemplary embodiments are provided for the purpose of illustration only and are not intended to limit the scope of the present disclosure.

EXAMPLE 1

Screening and Selection of Exporting Gene

As a result of a PSI-BLAST screen based on NCBI and KEGG databases with the amino add sequence of YdeD (i.e., an EamA family derived from *E. coli*) as a query sequence, 30 candidate genes, which are considered as membrane proteins capable of exporting tryptophan, and bioorganisms possessing these genes were selected. Among them, five kinds of bioorganisms were selected in consideration of biosafety levels, which are applicable to producing strains, and availability as shown in Table 1 below.

TABLE 1

Microorganisms expected to possess membrane protein capable of exporting aromatic amino acids

| No. | Strain | Protein Registration No. | Genome Registration No. | Biosafety Level |
|---|---|---|---|---|
| 1 | *Herbaspirillum rhizosphaerae* (KCTC12558) | WP_050478745.1 | NZ_LFLU01000012.1 | 1 |
| 2 | *Pseudomonas stutzeri* (KCTC22466) | WP_037022429.1 | NC_018177.1 | 1 |
| 3 | *Alcaligenes faecalis* (KCTC2678) | WP_045930186.1 | NZ_CP013119.1 | 1 |
| 4 | *Cupriavidus necator* (KCTC22469) | WP_011616478.1 | AM260480.1 | 1 |
| 5 | *Escherichia coli* str. K-12 substr. MG1655 | WP_000198205.1 | NC_000913.3 | 1 |

EXAMPLE 2

Preparation of Microorganism of the Genus *Corynebacterium* Where Gene Derived from *Herbaspirillum rhizosphaerae* is Introduced The gene encoding the membrane protein derived from *Herbaspirillum rhizosphaerae* selected in Example 1 has the amino acid sequence of SEQ ID NO: 1. The informations on the gene encoding the membrane protein and adjacent nucleotide sequences thereof (Registration No. NZ_LFLU01000012.1) were obtained from NIH GenBank.

Primers for inserting a *Herbaspirillum rhizosphaerae*-derived gene into the genomic DNA of *Corynebacterium glutamicum* were synthesized based on the obtained information of the nucleotide sequences. To amplify the *Herbaspirillum rhizosphaerae*-derived gene, PCR was performed using the chromosomal DNA of a *Herbaspirillum rhizosphaerae* strain as a template along with the primers of SEQ ID NO: 3 and SEQ ID NO: 4. Solg™ Pfu-X DNA polymerase was used as the polymerase, and PCR was performed as follows: denaturation at 95° C. for 2 minutes; 27 cycles of denaturation at 95° C. for 20 seconds, annealing at 62° C. for 40 seconds, and polymerization at 72° C. for 1 minute; and polymerization at 72° C. for 5 minutes.

As a result, a 956 bp gene fragment which includes the 924 bp gene (SEQ ID NO: 2) was obtained.

```
(wex - 1)
                                        SEQ ID NO: 3
TAGAGGAGACACAACATGAATAGCAAGAAGGCCAC

(wex - 2)
                                        SEQ ID NO: 4
ggctcttcctgtttAGTCTACAAACAGTCCGCCAC
```

To obtain the gapA promoter derived from *Corynebacterium glutamicum*, PCR was performed using the genomic DNA of *Corynebacterium glutamicum* as a template along with the primers of SEQ ID NO: 5 and SEQ ID NO: 6. Solg™ Pfu-X DNA polymerase (SolGent Co., Ltd.) was used as the polymerase, and PCR was performed as follows: denaturation at 95° C. for 2 minutes; 27 cycles of denaturation at 95° C. for 20 seconds, annealing at 62° C. for 40 seconds, and polymerization at 72° C. for 30 seconds; and polymerization at 72° C. for 5 minutes.

```
(PgapA - 1)
                                        SEQ ID NO: 5
cccttccggtttAGTTTGAAGCCAGTGTGAGTTGC

(PgapA(-wex) - 2)
                                        SEQ ID NO: 6
CTTCTTGCTATTCATGTTGTGTCTCCTCTAAAGATTGTA
```

The amplified gapA promoter region, the gene fragments derived from *Herbaspirillum rhizosphaerae*, and the pDZTn vector (KR Patent No. 10-1126041), which was cleaved with ScaI restriction enzyme, were cloned by the Gibson assembly method (D G Gibson et al., *NATURE METHODS*, VOL. 6 NO. 5, MAY 2009, NEBuilder HiFi DNA Assembly Master Mix), and thereby a recombinant plasmid was obtained. The recombinant plasmid was named as pDZTn-PgapA-Hrh. The cloning was performed by mixing the Gibson assembly reagent and each of the gene fragments in a calculated number of moles followed by incubating at 50° C. for one hour.

The prepared pDZTn-PgapA-Hrh vector was transformed into a wild-type *Corynebacterium glutamicum* ATCC13869 strain by electroporation (*Appl. Microbiol. Biotechnol.* (1999) 52: 541 to 545) and then subjected to a secondary crossover to obtain a strain in which one copy of the PgapA-Hrh gene is inserted between transposon genes in the chromosome. The corresponding genetic manipulation was confirmed through genome sequencing and a PCR method using the primers of SEQ ID NO: 7 and SEQ ID NO: 8, each of which can respectively amplify the external region of the upstream region and downstream region for homologous recombination where the corresponding gene is inserted.

```
(Confirm_PgapA-wex - 1)
                                  SEQ ID NO: 7
CGGATTATGCCAATGATGTG

(Confirm_PgapA-wex - 2)
                                  SEQ ID NO: 8
CACGATCACCAACATTCAGG
```

The thus-obtained strain was named as *Corynebacterium glutamicum* ATCC13869::PgapA-Hrh.

EXAMPLE 3

Preparation of Microorganism of the Genus *Corynebacterium* Where Gene Derived From *Pseudomonas stutzeri* is Introduced The gene encoding the membrane protein derived from *Pseudomonas stutzeri* selected in Example 1 has the amino add sequence of SEQ ID NO: 9. The informations on the corresponding gene and adjacent nucleotide sequences thereof (Registration No. NC_018177.1) were obtained from NIH GenBank.

Primers for inserting a *Pseudomonas stutzeri*-derived gene into the genomic DNA of *Corynebacterium glutamicum* were synthesized based on the obtained information of the nucleotide sequences. To amplify the *Pseudomonas stutzeri*-derived gene, PCR was performed in the same manner as in Example 2 using the chromosomal DNA of a *Pseudomonas stutzeri* strain as a template along with the primers of SEQ ID NO: 11 and SEQ ID NO: 12.

As a result, a 977 bp gene fragment which includes the 945 bp exporter gene (SEQ ID NO: 10) was obtained.

```
(Pst-1)
                                  SEQ ID NO: 11
TAGAGGAGACACAACATGAAAAACCAGCGTAAAGC

(Pst-2)
                                  SEQ ID NO: 12
ggctcttcctgtttAGTTTATCCGTTTCGACGCGG
```

For the use of gapA promoter derived from *Corynebacterium glutamicum*, PCR was performed in the same manner as in Example 2 using the genomic DNA of *Corynebacterium glutamicum* ATCC13869 as a template along with the primers of SEQ ID NO: 5 and SEQ ID NO: 13.

```
(PgapA(-Pst)-2)
                                  SEQ ID NO: 13
ACGCTGGTTTTTCATGTTGTGTCTCCTCTAAAGATTGTA
```

The amplified gapA promoter region, the gene fragments derived from *Pseudomonas stutzeri*, and the pDZTn vector, which was cleaved with ScaI restriction enzyme, were cloned by the Gibson assembly method, and thereby a recombinant plasmid was obtained. The recombinant plasmid was named as pDZTn-PgapA-Pst. The cloning was performed by mixing the Gibson assembly reagent and each of the gene fragments in a calculated number of moles followed by incubating at 50° C. for one hour.

The prepared pDZTn-PgapA-Pst vector was transformed into a wild-type *Corynebacterium glutamicum* ATCC13869 strain by electroporation (*Appl. Microbiol. Biotechnol.* (1999) 52: 541 to 545) and then subjected to a secondary crossover to obtain a strain in which one copy of the PgapA-Pst gene is inserted between transposon genes in the chromosome. The corresponding genetic manipulation was confirmed through genome sequencing and PCR method using the primers of SEQ ID NO: 7 and SEQ ID NO: 8, each of which can respectively amplify the external region of the upstream region and downstream region for homologous recombination where the corresponding gene is inserted.

The thus-obtained strain was named as *Corynebacterium glutamicum* ATCC13869::PgapA-Pst.

EXAMPLE 4

Preparation of Microorganism of the Genus *Corynebacterium* Where Gene Derived from *Alcaligenes faecalis* is Introduced The gene encoding the membrane protein derived from *Alcaligenes faecalis* selected in Example 1 has the amino add sequence of SEQ ID NO: 14. The informations on the corresponding gene and adjacent nucleotide sequences thereof (Registration No. NZ_CP013119.1) were obtained from NIH GenBank.

Primers for inserting an *Alcaligenes faecalis*-derived gene into the genomic DNA of *Corynebacterium glutamicum* were synthesized based on the obtained information of the nucleotide sequences. To amplify the *Alcaligenes faecalis*-derived gene, PCR was performed in the same manner as in Example 2 using the chromosomal DNA of an *Alcaligenes faecalis* strain as a template along with the primers of SEQ ID NO: 16 and SEQ ID NO: 17.

As a result, a 943 bp gene fragment which includes the 912 bp exporter gene (SEQ ID NO: 15) was obtained.

```
(Afa-1)
                                  SEQ ID NO: 16
TAGAGGAGACACAACATGAAGCAATCTGATAAGGC

(Afa-2)
                                  SEQ ID NO: 17
gctcttcctgtttAGTTCAGGCAGCGCTTTTTAGT
```

To obtain the gapA promoter derived from *Corynebacterium glutamicum*, PCR was performed in the same manner as in Example 2 using the genomic DNA of *Corynebacterium glutamicum* as a template along with the primers of SEQ ID NO: 5 and SEQ ID NO: 18.

```
(PgapA(-Afa)-2)
                                          SEQ ID NO: 18
ATCAGATTGCTTCATGTTGTGTCTCCTCTAAAGATTGTA
```

The amplified gapA promoter region, gene fragments derived from *Alcaligenes faecalis*, and the pDZTn vector, which was cleaved with ScaI restriction enzyme, were cloned by the Gibson assembly method, and thereby a recombinant plasmid was obtained. The recombinant plasmid was named as pDZTn-PgapA-Afa. The cloning was performed by mixing the Gibson assembly reagent and each of the gene fragments in a calculated number of moles followed by incubating at 50° C. for one hour.

The prepared pDZTn-PgapA-Afa vector was transformed into a wild-type *Corynebacterium glutamicum* ATCC13869 strain by electroporation and then subjected to a secondary crossover to obtain a strain in which one copy of the PgapA-Afa gene is inserted between transposon genes in the chromosome. The corresponding genetic manipulation was confirmed through genome sequencing and PCR method using the primers of SEQ ID NO: 7 and SEQ ID NO: 8, each of which can respectively amplify the external region of the upstream region and downstream region for homologous recombination where the corresponding gene is inserted.

The thus-obtained strain was named as *Corynebacterium glutamicum* ATCC13869::PgapA-Afa.

EXAMPLE 5

Preparation of Microorganism of the Genus *Corynebacterium* Where Gene Derived from *Cupriavidus necator* is Introduced The gene encoding the membrane protein derived from *Cupriavidus necator* selected in Example 1 has the amino add sequence of SEQ ID NO: 19. The informations on the corresponding gene and adjacent nucleotide sequences thereof (Registration No. AM260480.1) were obtained from NIH GenBank.

Primers for inserting a *Cupriavidus necator*-derived gene into the genomic DNA of *Corynebacterium glutamicum* were synthesized based on the obtained information of the nucleotide sequences. To amplify the *Cupriavidus necator*-derived gene, PCR was performed in the same manner as in Example 2 using the chromosomal DNA of the *Cupriavidus necator* strain as a template along with the primers of SEQ ID NO: 21 and SEQ ID NO: 22.

As a result, a 977 bp gene fragment which includes the 945 bp exporter gene derived from *Cupriavidus necator* (SEQ ID NO: 20) was obtained.

```
(Cne-1)
                                          SEQ ID NO: 21
TAGAGGAGACACAACATGCAAAGCAAGAGCAAAGC

(Cne-2)
                                          SEQ ID NO: 22
ggctcttcctgtttAGTTCACGGTTCCTGGACACG
```

To obtain the gapA promoter derived from *Corynebacterium glutamicum*, PCR was performed in the same manner as in Example 2 using the genomic DNA of *Corynebacterium glutamicum* as a template along with the primers of SEQ ID NO: 5 and SEQ ID NO: 23.

```
(PgapA(-Cne)-2)
                                          SEQ ID NO: 23
GCTCTTGCTTTGCATGTTGTGTCTCCTCTAAAGATTGTA
```

The amplified gapA promoter region, gene fragments derived from *Cupriavidus necator*, and the pDZTn vector, which was cleaved with ScaI restriction enzyme, were cloned by the Gibson assembly method, and thereby a recombinant plasmid was obtained. The recombinant plasmid was named as pDZTn-PgapA-Cne. The cloning was performed by mixing the Gibson assembly reagent and each of the gene fragments in a calculated number of moles followed by incubating at 50° C. for one hour.

The prepared pDZTn-PgapA-Cne vector was transformed into a wild-type *Corynebacterium glutamicum* ATCC13869 strain by electroporation and then subjected to a secondary crossover to obtain a strain in which one copy of the PgapA-Cne gene is inserted between transposon genes in the chromosome. The corresponding genetic manipulation was confirmed through genome sequencing and a PCR method using the primers of SEQ ID NO: 7 and SEQ ID NO: 8, each of which can respectively amplify the external region of the upstream region and downstream region for homologous recombination where the corresponding gene is inserted.

The thus-obtained strain was named as *Corynebacterium glutamicum* ATCC13869::PgapA-Cne.

EXAMPLE 6

Preparation of Microorganism of the Genus *Corynebacterium* Where Gene Derived From *Escherichia coli* str. K-12 Substr. MG1655 is Introduced The gene encoding the membrane protein derived from *Escherichia coli* str K-12 substr. MG1655 selected in Example 1 has the amino add sequence of SEQ ID NO: 24. The informations on the corresponding gene and adjacent nucleotide sequences thereof (Registration No. NC_000913.3) were obtained from NIH GenBank.

Primers for inserting an *Escherichia coli*-derived gene into the genomic DNA of *Corynebacterium glutamicum* were synthesized based on the obtained information of the nucleotide sequences. To amplify the *Escherichia coli*-derived gene, PCR was performed in the same manner as in Example 2 using the chromosomal DNA of the *Escherichia coli* strain as a template along with the primers of SEQ ID NO: 26 and SEQ ID NO: 27.

As a result, a 913 bp gene fragment which includes the 882 bp exporter gene (SEQ ID NO: 25) was obtained.

```
(Eco-1)
                                          SEQ ID NO: 26
TAGAGGAGACACAACATGACACGACAAAAAGCAAC

(Eco-2)
                                          SEQ ID NO: 27
gctcttcctgtttAGTTTAACCACGACGTGTCGCC
```

To obtain the gapA promoter derived from *Corynebacterium glutamicum*, PCR was performed in the same manner as in Example 2 using the genomic DNA of *Corynebacterium glutamicum* as a template along with the primers of SEQ ID NO: 5 and SEQ ID NO: 28.

```
(PgapA(-Eco)-2)
                                    SEQ ID NO: 28
TTTTTGTCGTGTCATGTTGTGTCTCCTCTAAAGATTG
```

The amplified gapA promoter region, gene fragments derived from *Escherichia coli*, and the pDZTn vector, which was cleaved with ScaI restriction enzyme, were cloned by the Gibson assembly method, and thereby a recombinant plasmid was obtained. The recombinant plasmid was named as pDZTn-PgapA-Eco. The cloning was performed by mixing the Gibson assembly reagent and each of the gene fragments in a calculated number of moles followed by incubating at 50° C. for one hour.

The prepared pDZTn-PgapA-Eco vector was transformed into a wild-type *Corynebacterium glutamicum* ATCC13869 strain by electroporation and then subjected to a secondary crossover to obtain a strain in which one copy of the PgapA-Eco gene is inserted between transposon genes in the chromosome. The corresponding genetic manipulation was confirmed through genome sequencing and a PCR method using the primers of SEQ ID NO: 7 and SEQ ID NO: 8, each of which can respectively amplify the external region of the upstream region and downstream region for homologous recombination where the corresponding gene is inserted.

The thus-obtained strain was named as *Corynebacterium glutamicum* ATCC13869::PgapA-Eco.

EXAMPLE 7

Measurement of MICs in Microorganism Strains of the Genus *Corynebacterium* Where Genes Derived From Various Microorganisms are Introduced To confirm the presence of tryptophan-exporting activity in the five types of *Corynebacterium glutamicum* strains prepared in Examples 2 to 6 (i.e., ATCC13869::PgapA-Hrh, ATCC13869::PgapA-Pst, ATCC13869::PgapA-Afa, ATCC13869::PgapA-Cne, and ATCC13869::PgapA-Eco), the minimum inhibitory concentration (MIC) experiment was performed using a tryptophan analogue and an analogue of phenylalanine (i.e., another aromatic amino add). The 5 different strains of *Corynebacterium glutamicum*, each introduced with a gene encoding a membrane protein, were cultured in the minimal liquid medium at 30° C. for 24 hours, diluted to a concentration of $3\times10^3$ cells and $3\times10^4$ cells, respectively, and then spot-cultured in a minimal solid medium where a tryptophan analogue or a phenylalanine analogue was added.

For the minimum inhibitory concentration (MIC) experiment, p-fluoro-DL-phenylalanine (2.5 mg/mL) or 5-fluoro-DL-tryptophan (0.25 μg/mL) was added to the minimal solid medium, and the cell growth was observed after 60 hours (Table 2).

All of the introductions of the selected five types of genes enabled cell growth under a condition where the phenylalanine analogue was added at a concentration of 2.5 mg/mL. Among them, the introduction of genes derived from *Herbaspirillum rhizosphaerae, Alcaligenes faecalis*, and *Escherichia coli* showed the highest cell growth. The introduction of the gene derived from *Pseudomonas stutzeri* showed slightly reduced cell growth compared to the above three kinds of strains, and the introduction of the gene derived from *Cupriavidus necator* showed the lowest cell growth. Under the same condition, the wild-type ATCC13869 strain did not grow. Additionally, under the condition where a tryptophan analogue was added at a concentration of 0.25 μg/mL, only the introduction of the gene derived from *Herbaspirillum rhizosphaerae* enabled cell growth.

From the above results, it was observed that all of the introductions of the selected five types of genes showed resistance to phenylalanine and the phenylalanine analogue even though there were differences in activity among the introductions. In contrast, with regard to tryptophan and the tryptophan analogue, only the introduction of the gene derived from *Herbaspirillum rhizosphaera* showed specific and excellent resistance thereto. Based on these results, it can be interpreted that only the membrane protein encoded by the gene derived from *Herbaspirillum rhizosphaera* can act as an exporter protein for tryptophan.

Minimal Medium (pH 7.2)

Glucose 10 g, $KH_2PO_4$ 1 g, $K_2HPO_4$ 2 g, $MgSO_4.7H_2O$ 0.4 g, Urea 2 g, $(NH_4)_2SO_4$ 5 g, NaCl 0.5 g, Nicotinamide 5 μg, Calcium pantothenate 0.1 μg, Biotin 0.2 μg, Thiamine HCl 3 μg, Trace elements solution 1 mL (based on 1 L of distilled water)

Trace Elements Solution $Na_2B_4O_7$ $10H_2O$ 0.09 g, $(NH_4)_6Mo_7O_{27}$ $4H_2O$ 0.04 g, $ZnSO_4.7H_2O$ 0.01 g, $CuSO_4$ $5H_2O$ 0.27 g, $MnCl_2.4H_2O$ 0.01 g, $FeCl_3.6H_2O$ 1 g, $CaCl_2$ 0.01 g (based on 1 L of distilled water)

TABLE 2

Growth of *Corynebacterium glutamicum* strains, in which genes derived from various microorganisms are introduced, in minimal medium containing a phenylalanine analogue or tryptophan analogue

| Strain | Growth: p-Fluoro phenylalanine (2.5 mg/mL) | Growth: 5'-Fluoro tryptophan (0.25 μg/mL) |
|---|---|---|
| ATCC13869 | − | − |
| ATCC13869::PgapA-Hrh | ++ | +++ |
| ATCC13869::PgapA-Pst | ++ | − |
| ATCC13869::PgapA-Afa | +++ | − |
| ATCC13869::PgapA-Cne | + | − |
| ATCC13869::PgapA-Eco | +++ | − |

EXAMPLE 8

Preparation of Expression Vector for *Escherichia coli* in Which Genes Derived From Various Microorganisms are Introduced To confirm the resistance of the genes derived from various microorganisms selected in Example 1 to tryptophan or an analogue thereof in *Escherichia coli*, each of the genes was cloned into pCL1920 (i.e., an *E. coli* expression vector) and expressed by the yccA promoter of *E. coli* W3110.

To obtain a fragment of the gene derived from *Herbaspirillum rhizosphaerae*, PCR was performed using the chromosomal DNA of a *Herbaspirillum rhizosphaerae* strain as a template along with the primers of SEQ ID NO: 29 and SEQ ID NO: 30. Solg™ Pfu-X DNA polymerase (SolGent Co., Ltd.) was used as the polymerase, and PCR was performed as follows: denaturation at 95° C. for 2 minutes; 27 cycles of denaturation at 95° C. for 20 seconds, annealing at 62° C. for 40 seconds, and polymerization at 72° C. for 1 minute; and polymerization at 72° C. for 5 minutes.

(Hrh-3)
SEQ ID NO: 29
ATAGAGAGTGACTCAATGAATAGCAAGAAGGCCAC (Hrh-4)
SEQ ID NO: 30
TCGAGCTCGGTACCCCTACWCAGTCCGCCAC

To obtain the yccA promoter derived from *E. coli* W3110, PCR was performed using the genomic DNA of the *E. coli* W3110 as a template along with the primers of SEQ ID NO: 31 and SEQ ID NO: 32. Solg™ Pfu-X DNA polymerase (SolGent Co., Ltd.) was used as the polymerase, and PCR was performed as follows: denaturation at 95° C. for 2 minutes; 27 cycles of denaturation at 95° C. for 20 seconds, annealing at 62° C. for 40 seconds, and polymerization at 72° C. for 10 seconds; and polymerization at 72° C. for 5 minutes.

(PyccA - 1)
SEQ ID NO: 31
CTCTAGAGGATCCCCTTCCAGATCAAATGCGTAA (PyccA(-Hrh)-2)
SEQ ID NO: 32
CTTCTTGCTATTCATTGAGTCACTCTCTATGACAG The amplified yccA promoter region, gene fragments derived from *Herbaspirillum rhizosphaerae*, and the pCL1920 vector (pSC101 ori, $Sp^r$), which was cleaved with SmaI restriction enzyme, were cloned by the Gibson assembly method, and thereby a recombinant plasmid was obtained. The recombinant plasmid was named as pCL1920-PyccA-Hrh. The cloning was performed by mixing the Gibson assembly reagent and each of the gene fragments in a calculated number of moles followed by incubating at 50° C. for one hour. The obtained pCL1920-PyccA-Hrh was introduced into the wild-type *E. coli* W3110, and thereby W3110/pCL1920-PyccA-Hrh (i.e., a transformant where the gene is expressed) was prepared.

To obtain a fragment of the gene derived from *Pseudomonas stutzeri*, PCR was performed using the chromosomal DNA of the *Pseudomonas stutzeri* strain as a template along with the primers of SEQ ID NO: 33 and SEQ ID NO: 34. Additionally, PCR was performed in the same manner as in obtaining the gene fragment from *Herbaspirillum rhizosphaerae* strain described above except that the primer of SEQ ID NO: 35, which was used to obtain the *E. coli* W3110-derived yccA promoter for use, was used.

(Pst-3)
SEQ ID NO: 33
ATAGAGAGTGACTCAATGAAAAACCAGCGTAAAGC (Pst-4)
SEQ ID NO: 34
TCGAGCTCGGTACCCTTATCCGTTTCGACGCGG (PyccA(-Pst)-2)
SEQ ID NO: 35
ACGCTGGTTTTTCATTGAGTCACTCTCTATGACAG As such, the recombinant plasmid was obtained and named as pCL1920-PyccA-Pst. The expression vector pCL1920-PyccA-Pst was transformed into wild-type *E. coli* W3110, and thereby W3110/pCL1920-PyccA-Pst (i.e., a transformant where the gene is expressed) was prepared.

The process of preparing a transformant, where the gene derived from an *Alcaligenes faecalis* strain is expressed, was the same as described above except that PCR was performed using the chromosomal DNA of an *Alcaligenes faecalis* strain as a template along with the primers of SEQ ID NO: 36 and SEQ ID NO: 37, and the primer of SEQ ID NO: 38 for obtaining the yccA promoter were used.

(Afa-3)
SEQ ID NO: 36
ATAGAGAGTGACTCAATGAAGCAATCTGATAAGGC (Afa-4)
SEQ ID NO: 37
TCGAGCTCGGTACCCTCAGGCAGCGCTTTTTAGT (PyccA(-Afa)-2)
SEQ ID NO: 38
ATCAGATTGCTTCATTGAGTCACTCTCTATGACAG As such, a recombinant plasmid into which the gene derived from *Alcaligenes faecalis* is cloned was obtained and named as pCL1920-PyccA-Afa. The expression vector pCL1920-PyccA-Afa was transformed into the wild-type *E. coli* W3110, and thereby W3110/pCL1920-PyccA-Afa (i.e., a transformant) was prepared.

To obtain a fragment of the gene derived from *Cupriavidus necator* strain, PCR was performed using the chromosomal DNA of the *Cupriavidus necator* strain as a template along with the primers of SEQ ID NO: 39 and SEQ ID NO: 40. Additionally, PCR was performed in the same manner as in obtaining the gene fragment from *Herbaspirillum rhizosphaerae* strain described above except that the primer of SEQ ID NO: 41, which was used to obtain the *E. coli* W3110-derived yccA promoter for use, was used.

(Cne-3)
SEQ ID NO: 39
ATAGAGAGTGACTCAATGCAAAGCAAGAGCAAAGC (Cne-4)
SEQ ID NO: 40
TCGAGCTCGGTACCCTCACGGTTCCTGGACACG (PyccA(-Cne)-2)
SEQ ID NO: 41
GCTCTTGCTTTGCATTGAGTCACTCTCTATGACAG As such, a recombinant plasmid was obtained and named as pCL1920-PyccA-Cne. The expression vector pCL1920-PyccA-Cne was transformed into the wild-type *E. coli* W3110, and thereby W3110/pCL1920-PyccA-Cne (i.e., a transformant where the gene is expressed) was prepared.

To obtain a fragment of the gene derived from *Escherichia coli* strain, PCR was performed using the chromosomal DNA of the *Escherichia coli* str. K-12 substr. MG1655 strain as a template along with the primers of SEQ ID NO: 42 and SEQ ID NO: 43. Additionally, PCR was performed in the same manner as in obtaining the gene fragment from *Herbaspirillum rhizosphaerae* strain described above except that the primer of SEQ ID NO: 44, which was used to obtain the *E. coli* W3110-derived yccA promoter for use, was used.

(Eco-3)
SEQ ID NO: 42
ATAGAGAGTGACTCAATGACACGACAAAAAGCAAC (Eco-4)
SEQ ID NO: 43
TCGAGCTCGGTACCCTTAACCACGACGTGTCGCC (PyccA(-Eco)-2)
SEQ ID NO: 44
TTTTTGTCGTGTCATTGAGTCACTCTCTATGACAG As such, a recombinant plasmid was obtained and named as pCL1920-PyccA-Eco. The expression vector pCL1920-PyccA-Eco was introduced into the wild-type *E. coli* W3110, and thereby W3110/pCL1920-PyccA-Cne (i.e., a transformant where the gene is expressed) was prepared.

EXAMPLE 9

Measurement of MIC of *E. coli* in Which Genes for Membrane Proteins Derived From Various Microorganisms are Overexpressed To confirm the resistance of *E. coli* strains where the five types of genes prepared in Example 8 are overexpressed (i.e., W3110/pCL1920-PyccA-Hrh, W3110/pCL1920-PyccA-Pst, W3110/pCL1920-PyccA-Afa, W3110/pCL1920-PyccA-Cne, and W3110/pCL1920-PyccA-Eco), the minimum inhibitory concentration (MIC) experiment was performed using a tryptophan analogue and a phenylalanine analogue. The *E. coli* strains where the five types of genes are overexpressed were cultured in M9 minimal liquid medium containing spectinomycin (50 μg/mL) at 37° C. for 15 hours, diluted at concentrations of $10^4$ cells and $10^5$ cells, respectively, and then spot-cultured in M9 glucose minimal solid medium containing spectinomycin (50 μg/mL) where a tryptophan analogue or phenylalanine analogue was added. For the minimum inhibitory concentration (MIC) experiment, p-fluoro-DL-phenylalanine (2 mg/mL) or 5-fluoro-DL-tryptophan (0.7 μg/mL) was added to the M9 minimal solid medium, and the cell growth was observed after 48 hours (Table 3).

As in *Corynebacterium glutamicum* strains, *E. coli* strains showed excellent growth under the condition where a phenylalanine analogue was added when the genes derived from *E. coli* were overexpressed, and the overexpression of the gene derived from *Alcaligenes faecalis* also showed significant growth. However, the overexpression of the genes derived from *Herbaspirillum rhizosphaerae, Pseudomonas stutzeri*, and *Cupriavidus necator* failed to show comparable growth as in W3110/pCL1920 (i.e., the control group). In contrast, the overexpression of all of the five types of selected genes enabled all of the cells to grow under the condition where the tryptophan analogue was added. Among them, the overexpression of the *Herbaspirillum rhizosphaerae*-derived gene enabled the highest growth, and the overexpression of the exporter genes derived from *Alcaligenes faecalis* and *E. coli* enabled the second highest growth. The overexpression of the exporter genes derived from *Pseudomonas stutzeri* and *Cupriavidus necator* showed negligible growth.

The results of the MIC experiment about the five types of genes in *E. coli* strain were similar to those observed in *Corynebacterium glutamicum*. The *Herbaspirillum rhizosphaerae*-derived gene showed specific and excellent resistance to tryptophan and its analogue in both *Corynebacterium glutamicum* and *E. coli* strains, and the exporter gene derived from *E. coli* showed higher resistance of exportation to phenylalanine and its analogue than to tryptophan. From these results, it was determined that the *Herbaspirillum rhizosphaerae*-derived gene shows a specific and excellent exporting ability for tryptophan in both *Corynebacterium glutamicum* and *E. coli* strains.

TABLE 3

Growth of *E. coli* strains where each gene is overexpressed in a minimal medium containing a phenylalanine analogue or a tryptophan analogue

| Strain | Growth: p-Fluorophenylalanine (2.5 mg/mL) | Growth: 5'-Fluoro tryptophan (0.7 μg/mL) |
|---|---|---|
| W3110/pCL 1920 | – | – |
| W3110/pCL 1920-PyccA-Hrh | – | ++++ |
| W3110/pCL 1920-PyccA-Pst | – | + |
| W3110/pCL 1920-PyccA-Afa | ++ | ++ |
| W3110/pCL 1920-PyccA-Cne | – | + |
| W3110/pCL 1920-PyccA-Eco | +++ | ++ |

REFERENCE EXAMPLE 1

Preparation of L-Tryptophan-Producing Microorganism of the Genus *Corynebacterium*

The L-tryptophan-producing strains were developed from wild-type *Corynebacterium glutamicum* ATCC13869. Since the wild-type *Corynebacterium glutamicum* cannot produce L-tryptophan or can produce only a very small amount even when it is possible, an attempt was made to use the strain where the biosynthesis pathway essential for the production of L-tryptophan is enhanced as the parent strain. Specifically, the expression of the operon of L-tryptophan biosynthetic genes was increased by enhancing the promoter. Additionally, to release the feedback inhibition of the TrpE protein, the 38$^{th}$ amino add of TrpE (i.e., serine) was substituted with arginine (*Journal of Bacteriology*, November 1987, p. 5330 to 5332).

For the above genetic manipulation, first, the upstream region of the trpE promoter and the downstream region of the 38$^{th}$ amino add mutation of TrpE were obtained for homologous recombination in the chromosome. Specifically, the genetic fragment of the upstream region of the trpE promoter was obtained by performing PCR using the chromosomal DNA of *Corynebacterium glutamicum* as a template along with the primers of SEQ ID NO: 45 and SEQ ID NO: 46, whereas the genetic fragment of the downstream region of the 38$^{th}$ amino add mutation of TrpE was obtained by performing PCR using the chromosomal DNA of *Corynebacterium glutamicum* as a template along with the primers of SEQ ID NO: 47 and SEQ ID NO: 48.

```
(Pspl7-trpE(S38R)_L-1)
                                          SEQ ID NO: 45
TCGAGCTCGGTACCCAAACAACTGCGACGTGTGTC

(Pspl7-trpE(S38R)_L-2)
                                          SEQ ID NO: 46
CATGAAGCGCCGGTACCTTAATCATTTTTGGGTTC

(Pspl7-trpE(S38R)_R-1)
                                          SEQ ID NO: 47
GCCCTGTTGGAACGCGCTGATATCACCACCAAGAA

(Pspl7-trpE(S38R)_R-2)
                                          SEQ ID NO: 48
CTCTAGAGGATCCCCAGATGTCACCGTTGTAAATG
```

Solg™ Pfu-X DNA polymerase (SolGent Co., Ltd.) was used as the polymerase, and PCR was performed as follows: denaturation at 95° C. for 5 minutes; 30 cycles of denaturation at 95° C. for 30 seconds, annealing at 60° C. for 30 seconds, and polymerization at 72° C. for 60 seconds; and polymerization at 72° C. for 5 minutes.

The PCR was performed using the synthesized promoter SPL7 (SEQ ID NO: 49) as a template along with the primers of SEQ ID NO: 50 and SEQ ID NO: 51.

```
(Psp17 - 1)
                                        SEQ ID NO: 50
CCCAAAAATGATTAAGGTACCGGCGCTTCATGTCA

(Psp17 - 2)
                                        SEQ ID NO: 51
GGGATTCGTGCTCATGATATCTGTTTTGATCTCCTCC
```

Solg™ Pfu-X DNA polymerase (SolGent Co., Ltd.) was used as the polymerase, and PCR was performed as follows: denaturation at 95° C. for 5 minutes; 30 cycles of denaturation at 95° C. for 30 seconds, annealing at 60° C. for 30 seconds, and polymerization at 72° C. for 30 seconds; and polymerization at 72° C. for 5 minutes.

To obtain an upstream fragment of *Corynebacterium glutamicum*-derived TrpE, including the amino add sequence from the 1$^{st}$ amino add to the mutated 38$^{th}$ amino add, PCR was performed using the genomic DNA of *Corynebacterium glutamicum* as a template along with the primers of SEQ ID NO: 52 and SEQ ID NO: 53.

```
(trpE (S38R) - 1)
                                        SEQ ID NO: 52
ATCAAAACAGATATCATGAGCACGAATCCCCATGT

(trpE (S38R) - 2)
                                        SEQ ID NO: 53
GTGGTGATATCAGCGCGTTCCAACAGGGCTGCATC
```

Solg™ Pfu-X DNA polymerase (SolGent Co., Ltd.) was used as the polymerase, and PCR was performed as follows: denaturation at 95° C. for 5 minutes; 30 cycles of denaturation at 95° C. for 30 seconds, annealing at 60° C. for 30 seconds, and polymerization at 72° C. for 30 seconds; and polymerization at 72° C. for 5 minutes.

A recombinant plasmid was obtained by cloning the amplified upstream region of the trpE promoter and the downstream region of the mutated 38$^{th}$ amino add of TrpE, the SPL7 promoter and the upstream fragment of TrpE, and the pDZ vector which was cleaved with SmaI restriction enzyme using the Gibson assembly method. The recombinant plasmid was named as pDZ-PSPL7-trpE (S38R). The cloning was performed by mixing the Gibson assembly reagent and each of the gene fragments in a calculated number of moles followed by incubating at 50° C. for one hour.

The prepared pDZ-PSPL7-trpE (S38R) vector was transformed into the *Corynebacterium glutamicum* ATCC13869 strain by electroporation and then subjected to a secondary crossover. Then, a strain, in which a promoter of the trpE is replaced with SPL7 promoter (i.e., a stronger promoter) and the 38$^{th}$ amino add of TrpE (i.e., serine) is replaced with arginine in the chromosome, was obtained. The corresponding genetic manipulation was confirmed through genome sequencing and a PCR method using the primers of SEQ ID NO: 54 and SEQ ID NO: 55, which can amplify the upstream region and downstream region for homologous recombination where the gene is inserted, and the resulting strain was named as CA04-8325.

```
(Confirm_Psp17-trpE(S38R) - 1)
                                        SEQ ID NO: 54
GAAGAAGAGGCTGCAGATG

(Confirm_Psp17-trpE(S38R) - 2)
                                        SEQ ID NO: 55
GATCAGCGCCATCATGTT
```

Tryptophan production occurs from the aromatic amino add metabolic pathway, and this metabolic pathway starts from the condensation reaction between phosphoenolpyruvate and erythrose 4-phosphate. Accordingly, a smooth supply of these two precursors is essential for the production of tryptophan, and the overexpression of the tkt gene was performed for the smooth supply of erythrose 4-phosphate, which is known to be relatively deficient.

For the above genetic manipulation, PCR was performed using the chromosomal DNA of *Corynebacterium glutamicum* as a template along with the primers of SEQ ID NO: 56 and SEQ ID NO: 57 to obtain the upstream region for the additional insertion of the tkt gene, and along with the primers of SEQ ID NO: 58 and SEQ ID NO: 59 to obtain the downstream region for the additional insertion of the tkt gene.

```
(Pn-tkt_L - 1)
                                        SEQ ID NO: 56
TCGAGCTCGGTACCCAAACTTTGAGTGGGTGCGTG

(Pn-tkt_L - 2)
                                        SEQ ID NO: 57
TCGAGCTACGAGGGCGGTTCCCAGCCCTTCATTAG

(Pn-tkt_R - 1)
                                        SEQ ID NO: 58
ATTAACGGTTAATTGATTCTGGACGTCATGACTAC

(Pn-tkt_R - 2)
                                        SEQ ID NO: 59
CTCTAGAGGATCCCCGCCTCGATGATGCAGTCGTC
```

Solg™ Pfu-X DNA polymerase was used as the polymerase, and PCR was performed as follows: denaturation at 95° C. for 2 minutes; 27 cycles of denaturation at 95° C. for 20 seconds, annealing at 62° C. for 40 seconds, and polymerization at 72° C. for 30 seconds; and polymerization at 72° C. for 5 minutes.

To obtain the tkt gene and its promoter, PCR was performed using the chromosomal DNA of wild-type *Corynebacterium glutamicum* ATCC13869 as a template along with the primers of SEQ ID NO: 60 and SEQ ID NO: 61, and thereby the tkt gene including its promoter was obtained.

```
(Pn-tkt - 1)
                                        SEQ ID NO: 60
GAAGGGCTGGGAACCGCCCTCGTAGCTCGAGAGTT

(Pn-tkt - 2)
                                        SEQ ID NO: 61
CATGACGTCCAGAATCAATTAACCGTTAATGGAGTCC
```

Solg™ Pfu-X DNA polymerase was used as the polymerase, and PCR was performed as follows: denaturation at 95° C. for 2 minutes; 27 cycles of denaturation at 95° C. for 20 seconds, annealing at 62° C. for 40 seconds, and polymerization at 72° C. for 1 minute and 20 seconds; and polymerization at 72° C. for 5 minutes.

A recombinant plasmid was obtained by cloning the amplified upstream region for the additional insertion of the tkt gene and downstream region for the additional insertion of the tkt gene, the tkt gene including tkt promoter, and the pDZ vector for chromosomal transformation, which is cleaved by SmaI restriction enzyme using the Gibson assembly method, and the resultant recombinant plasmid was named as pDZ-Pn-tkt. The cloning was performed by mixing the Gibson assembly reagent and each of the gene fragments in a calculated number of moles followed by incubating at 50° C. for one hour.

The prepared pDZ-Pn-tkt vector was transformed into the CA04-8325 strain by electroporation and then subjected to a secondary crossover to obtain a strain in which the tkt gene including tkt promoter is inserted into the chromosome. The corresponding genetic manipulation was confirmed through genome sequencing and a PCR method using the primers of SEQ ID NO: 62 and SEQ ID NO: 63, which can respectively amplify the external region of the upstream region and downstream region for homologous recombination where the corresponding gene is inserted. The resulting strain was named as CA04-8352. The CA04-8352 strain was internationally deposited at the Korean Culture Center of Microorganisms (KCCM), an international depositary, on Feb. 2, 2018, under the provisions of the Budapest Treaty and assigned accession number KCCM 12218.

```
(Confirm_Pn-tkt - 1)
                                        SEQ ID NO: 62
ACCCAGAACCCCAAATTTTC

(Confirm_Pn-tkt - 2)
                                        SEQ ID NO: 63
TTGAGTTCGACAACTTTGG
```

EXAMPLE 10

Tryptophan Production by Microorganism of the Genus *Corynebacterium* Where Genes Derived from *Herbaspirillum rhizosphaerae* and *E. coli* are Introduced The *Herbaspirillum rhizosphaerae*-derived gene, which showed excellent activity in the minimum inhibitory concentration of the tryptophan analogue in Example 7, was introduced into CA04-8352, which is a tryptophan-producing strain prepared in Reference Example 1. For this purpose, the pDZTn-PgapA-Hrh vector for the introduction of the *Herbaspirillum rhizosphaerae*-derived gene prepared in Example 2 was transformed into CA04-8352 (i.e., a tryptophan-producing strain) by electroporation and subjected to the process as in Example 2, and thereby a strain was obtained in which one copy of the *Herbaspirillum rhizosphaerae*-derived gene is inserted between transposon genes. The resulting strain was named as CA04-8405.

Additionally, the *E. coli*-derived gene was introduced into the CA04-8352 (i.e., a tryptophan-producing strain) as the control group. The pDZTn-PgapA-Eco vector for the introduction of the *E. coli*-derived gene prepared in Example 6 was transformed into CA04-8352 (i.e., a tryptophan-producing strain) by electroporation and subjected to the process as in Example 6, and thereby a strain was obtained in which one copy of the *E. coli*-derived gene is inserted between transposon genes. The resulting strain was named as CA04-8406.

The strains CA04-8405 and CA04-8406 obtained by the processes described above were cultured by the following method so as to confirm the amount of tryptophan production relative to the CA04-8352 strain, which was prepared in Reference Example 1 as the control group. Each strain was inoculated into a 250 mL corner-baffle flask containing seed medium (25 mL) and cultured with shaking at 30° C. at 200 rpm for 20 hours. Then, each seed culture solution (1 mL) was inoculated into a 250 mL corner-baffle flask containing production medium (25 mL) and cultured with shaking at 30° C. at 200 rpm for 24 hours. After completion of the culture, the amount of L-tryptophan production was measured by HPLC.

Seed Medium (pH 7.0)

Glucose 20 g, Peptone 10 g, Yeast extract 5 g, Urea 1.5 g, $KH_2PO_4$ 4 g, $K_2HPO_4$ 8 g, $MgSO_4.7H_2O$ 0.5 g, Biotin 100 μg, Thiamine HCl 1,000 μg, Calcium pantothenate 2,000 μg, Nicotinamide 2,000 μg (based on 1 L of distilled water)

Production Medium (pH 7.0)

Glucose 30 g, $(NH_4)_2SO_4$ 15 g, $MgSO_4.7H_2O$ 1.2 g, $KH_2PO_4$ 1 g, Yeast extract 5 g, Biotin 900 μg, Thiamine HCl 4,500 μg, Calcium pantothenate 4,500 μg, $CaCO_3$ 30 g (based on 1 L of distilled water).

TABLE 4

Confirmation of amount of L-tryptophan production by CA04-8352 (a *Corynebacterium glutamicum* strain producing L-tryptophan), CA04-8405 (a strain where a gene derived from *Herbaspirillum rhizosphaerae* is inserted), and CA04-8406 (a strain where a gene derived from *E. coli* is inserted)

| | $OD_{562}$ | Amount of Tryptophan Production (g/L) | Tryptophan Yield (g/g glc, %) |
|---|---|---|---|
| CA04-8352 | 56.5 | 0.25 | 0.83 |
| CA04-8405 | 52.3 | 1.52 | 5.07 |
| CA04-8406 | 56.1 | 0.24 | 0.80 |

The results of the L-tryptophan production by CA04-8352, CA04-8405, and CA04-8406 strains in the medium are shown in Table 4 above. The CA04-8405 strain in which the *Herbaspirillum rhizosphaerae*-derived gene is introduced produced L-tryptophan at a final concentration of 1.52 g/L in flask cultivation, and this is an about 5-fold improvement compared to that of the CA04-8352 strain (i.e., the control group). This indicates that the *Herbaspirillum rhizosphaerae*-derived gene can significantly improve L-tryptophan production in a *Corynebacterium glutamicum* strain. In contrast, the CA04-8406 strain in which an *E. coli*-derived gene was introduced produced L-tryptophan at a concentration of 0.23 g/L, which is almost the same as the amount of L-tryptophan production by the CA04-8352 strain (i.e., the parent strain of the CA04-8406 strain). As confirmed in the minimum inhibitory concentration (MIC) experiment of the tryptophan analogue and the phenylalanine analogue in Examples 7 and 9, the *E. coli*-derived gene is considered to be an exporter gene that shows higher specificity to phenylalanine than to tryptophan. The CA04-8405 strain was internationally deposited at the Korean Culture Center of Microorganisms (KCCM), an international depositary, on Aug. 21, 2017, under the provisions of the Budapest Treaty and assigned accession number KCCM12099P (CA04-8405).

EXAMPLE 11

Analysis of Intracellular Tryptophan Metabolites in *Corynebacterium glutamicum* Where a Gene Derived From *Herbaspirillum rhizosphaerae* is Introduced To explicitly confirm whether the intracellular tryptophan concentration decreases as the tryptophan-exporting ability of the CA04-8405 strain (i.e., a tryptophan-producing strain) improves, the intracellular tryptophan concentration was measured in the CA04-8405 strain and the CA04-8352 strain (i.e., the parent strain of the CA04-8405 strain) by an extraction method using an organic solvent.

The method for analyzing the intracellular metabolites was performed according to the method described in the reference (Nakamura J et al., *Appl. Environ. Microbiol* 73(14): 4491 to 4498, 2007).

First, with regard to the mutated *Corynebacterium glutamicum* strains of CA04-8352 and CA04-8405, each strain was inoculated into a 250 mL corner-baffle flask containing seed medium (25 mL) and cultured with shaking at 30° C. at 200 rpm for 20 hours. Then, each seed culture solution (1 mL) was inoculated into a 250 mL corner-baffle flask containing production medium (25 mL) and cultured with shaking at 30° C. at 200 rpm. The intracellular tryptophan concentration was analyzed three times according to glucose consumption. The cultured cells in each step were separated from the culture solution by rapid vacuum filtration (Durapore HV, 0.45 m; Millipore, Billerica, Mass.). The filter to which cells were adsorbed was washed twice with distilled water (10 mL) and soaked in methanol containing 5 μM morpholine ethanesulfonic acid and 5 μM methionine sulfone for 10 minutes. Chloroform (1.6 mL) and distilled water (0.64 μL) were added to the cell extract (1.6 mL) obtained above and thoroughly mixed, and only the aqueous phase was applied to the spin column to remove protein impurities. The filtered extract was analyzed using the capillary electrophoresis mass spectrometry, and the results are shown in FIG. 1.

As shown in FIG. 1, it was confirmed that the CA04-8405 strain showed a decrease of the intracellular tryptophan concentration to a level of 33% to 41%, compared to its parent strain, CA04-8352. These results indicate that as the tryptophan produced within the cells of a *Corynebacterium glutamicum* strain was smoothly exported extracellularly due to the expression of the *Herbaspirillum rhizosphaerae*-derived gene, the intracellular tryptophan concentration of the CA04-8405 strain decreased. From these results, it was confirmed that the *Herbaspirillum rhizosphaerae*-derived gene is a gene encoding a membrane protein having an exporting ability specific to tryptophan.

REFERENCE EXAMPLE 2

Preparation of L-Tryptophan-Producing Microorganism of the Genus *Escherichia*

The L-tryptophan-producing microorganism of the genus *Escherichia* was developed from the wild-type *E. coli* W3110. To confirm whether the amount of tryptophan production significantly increases as the protein having an L-tryptophan-exporting activity is modified to be expressed, the strain prepared to produce L-tryptophan was used as the parent strain. Specifically, the expression of the L-tryptophan biosynthesis genes (trpEDCBA), which are involved in the production of L-tryptophan from chorismate, is inhibited by TrpR. Accordingly, the trpR gene encoding TrpR was removed. Additionally, to release the feedback inhibition of the TrpE polypeptide according to the improvement of L-tryptophan production, the $21^{st}$ amino acid from the N-terminus of TrpE (i.e., proline) was substituted with serine (*J. Biochem. Mol. Biol.* 32, 20 to 24 (1999)).

The Mtr membrane protein has the role of introducing extracellular L-tryptophan into a cell, and the TnaA protein has the role of decomposing the intracellular L-tryptophan and water molecules into indole, pyruvate, and ammonia ($NH_3$). Accordingly, the mtr and tnaA genes that inhibit L-tryptophan production and decompose the same were removed.

For the removal of these genes, the λ-red recombination method (One-step inactivation of chromosomal genes in *Escherichia coli* K-12 using PCR products, Datsenko K A, Wanner B L., *Proc Natl Aced Sci USA.* 2000 Jun. 6; 97(12): 6640 to 6645) was used. For the removal of the mtr gene, PCR was performed using the pKD4 vector as a template along with the primers of SEQ ID NO: 64 and SEQ ID NO: 65. As a result, a 1,580 bp gene fragment, in which an FRT-kanamycin-FRT cassette is bound to a pair of 50 bp homologous nucleotides flanking the mtr gene, where chromosomal homologous recombination occurs therebetween, was obtained. The kanamycin antibiotic marker of the pKD4 vector was used for the confirmation of removal of a target gene and insertion of an antibiotic gene, and the FRT region has the role of removing the antibiotic marker after the removal of the target gene.

Solg™ Pfu-X DNA polymerase was used as the polymerase, and PCR was performed as follows: denaturation at 95° C. for 2 minutes; 27 cycles of denaturation at 95° C. for 20 seconds, annealing at 62° C. for 40 seconds, and polymerization at 72° C. for 1 minute; and polymerization at 72° C. for 5 minutes.

```
(Δmtr cassette - 1)
                                              SEQ ID NO: 64
TGCAATGCATAACAACGCAGTCGCACTATTTTTCACTGGAGAGAAGCCCTG

TGTAGGCTGGAGCTGCTTC

(Δmtr cassette - 2)
                                              SEQ ID NO: 65
TGCAATGCATAACAACGCAGTCGCACTATTTTTCACTGGAGAGAAGCCCTG

TCCATATGAATATCCTCCT
```

The pKD46 vector which expresses lambda red recombinase (gam, bet, and exo genes) was transformed into the *E. coli* W3110 strain by electroporation, and the strain was spread on LB solid medium containing kanamycin (50 mg/L). The *E. coli* W3110 strain in which the transformation of the pKD46 vector was confirmed induced the expression of a recombinant enzyme by the addition of 10 mM L-arabinose when the $OD_{600}$ reached about 0.1. When the $OD_{600}$ reached about 0.6, the strain was prepared into a competent cell, and the linear gene fragment obtained in the above process, in which an FRT-kanamycin-FRT cassette is bound to a pair of 50 bp homologous nucleotides flanking the mtr gene, was transformed by electroporation. For the colonies grown on LB solid medium containing kanamycin (25 mg/L), colony PCR was performed using the primers of SEQ ID NO: 66 and SEQ ID NO: 67, and the colonies where the 782 bp gene fragment is prepared were selected.

```
(Confirm_Cassette - 1)
                                              SEQ ID NO: 66
GGGCAGGATCTCCTGTCATC

(Confirm_Δmtr - 2)
                                              SEQ ID NO: 67
AAATGTCGGATAAGGCACCG
```

The strain in which the mtr gene was removed due to the occurrence of homologous recombination was prepared into a competent cell so as to remove the kanamycin antibiotic marker and then transformed with the pCP20 vector by electroporation. The pCP20 vector expresses the FLP protein and thereby recognizes the FRT sites flanking the kanamycin antibiotic and binds thereto in the chromosome, thereby removing the antibiotic marker between the FRT sites. The pCP20 vector-transformed strain grown in LB solid medium containing ampicillin (100 mg/L) and chloramphenicol (25 mg/L) was cultured in LB liquid medium at 30° C. for one hour, further cultured at 42° C. for 15 hours, and spread on LB solid medium. The grown colonies were cultured in LB solid medium containing ampicillin (100 mg/L) and chloramphenicol (25 mg/L); LB solid medium containing kanamycin (12.5 mg/L); and LB solid medium containing no antibiotic. Only the colonies which grew in LB solid medium containing no antibiotic were selected. The removal of the mtr gene was finally confirmed by genome sequencing and the strain was named as CA04-9300.

Genetic manipulation was performed by the method described above so as to remove the tnaA gene. PCR was performed using the pKD4 vector as a template along with the primers of SEQ ID NO: 68 and SEQ ID NO: 69, and thereby a 1,580 bp gene fragment, in which an FRT-kanamycin-FRT cassette is bound to a pair of 50 bp homologous nucleotides flanking the tnaA gene, where chromosomal homologous recombination occurs therebetween, was obtained. Solg™ Pfu-X DNA polymerase was used as the polymerase, and PCR was performed as follows: denaturation at 95° C. for 2 minutes; 27 cycles of denaturation at 95° C. for 20 seconds, annealing at 62° C. for 40 seconds, and polymerization at 72° C. for 1 minute; and polymerization at 72° C. for 5 minutes.

(ΔtnaA cassette - 1)

SEQ ID NO: 68

TGTAATATTCACAGGGATCACTGTAATTAAAATAAATGAAGGATTATGTAG

TGTAGGCTGGAGCTGCTTC (ΔtnaA cassette - 2)

SEQ ID NO: 69

TGTAGGGTAAGAGAGTGGCTAACATCCTTATAGCCACTCTGTAGTATTAAG

TCCATATGAATATCCTCCT

The transformation of pKD46 vector was confirmed. The CA04-9300, in which the recombinases were expressed by the addition of 10 mM L-arabinose was transformed by electroporation with the linear gene fragment obtained in the above process, in which an FRT-kanamycin-FRT cassette is bound to a pair of 50 bp homologous nucleotides flanking the tnaA gene. For the colonies grown on LB solid medium containing kanamycin (25 mg/L), colony PCR was performed using the primers of SEQ ID NO: 66 and SEQ ID NO: 70, and the colonies where the 787 bp gene fragment is prepared were selected.

(Confirm_ΔtnaA - 2)

SEQ ID NO: 70

ACATCCTTATAGCCACTCTG

The strain in which the tnaA gene was removed due to homologous recombination was prepared into a competent cell so as to remove the kanamycin antibiotic marker and then transformed with the pCP20 vector, and a strain where the kanamycin antibiotic marker was removed by the expression of the FLP protein was prepared. The removal of the tnaA gene was finally confirmed by genome sequencing and the strain was named as CA04-9301.

To remove the trpR gene, PCR was performed using the pKD4 vector as a template along with the primers of SEQ ID NO: 71 and SEQ ID NO: 72, and thereby the gene fragment (1,580 bp), in which an FRT-kanamycin-FRT cassette is bound to a pair of 50 bp homologous nucleotides flanking the trpR gene, where chromosomal homologous recombination occurs therebetween, was obtained. Solg™ Pfu-X DNA polymerase was used as the polymerase, and PCR was performed as follows: denaturation at 95° C. for 2 minutes; 27 cycles of denaturation at 95° C. for 20 seconds, annealing at 62° C. for 40 seconds, and polymerization at 72° C. for 1 minute; and polymerization at 72° C. for 5 minutes.

(ΔtrpR cassette - 1)

SEQ ID NO: 71

TACAACCGGGGGAGGCATTTTGCTTCCCCCGCTAACAATGGCGACATATTG

TGTAGGCTGGAGCTGCTTC (ΔtrpR cassette - 2)

SEQ ID NO: 72

GCATTCGGTGCACGATGCCTGATGCGCCACGTCTTATCAGGCCTACAAAAG

TCCATATGAATATCCTCCT

The transformation of pKD46 vector was confirmed. The CA04-9301 in which the recombinases were expressed by the addition of 10 mM L-arabinose was transformed by electroporation with the linear gene fragment obtained in the above process, in which an FRT-kanamycin-FRT cassette is bound to a pair of 50 bp homologous nucleotides flanking the trpR gene. For the colonies grown on LB solid medium containing kanamycin (25 mg/L), colony PCR was performed using the primers of SEQ ID NO: 66 and SEQ ID NO: 73, and the colonies where the 838 bp gene fragment is prepared were selected.

(Confirm_ΔtrpR-2)

SEQ ID NO: 73

AGGACGGATAAGGCGTTCAC

The strain in which the trpR gene was removed due to homologous recombination was prepared into a competent cell so as to remove the kanamycin antibiotic marker and then transformed with the pCP20 vector, and a strain where the kanamycin antibiotic marker was removed by the expression of the FLP protein was prepared. The removal of the trpR gene was finally confirmed by genome sequencing and the strain was named as CA04-9307.

To provide the CA04-9307 strain with a feedback resistant trpE trait, PCR was performed using the *E. coli* W3110 gDNA as a template along with the primers of SEQ ID NO: 74 and SEQ ID NO: 75 (both of which include an EcoRI restriction site), and thereby a 1,575 bp trpE gene fragment containing an EcoRI restriction site was obtained. Solg™ Pfu-X DNA polymerase was used as the polymerase, and PCR was performed as follows: denaturation at 95° C. for 2 minutes; 27 cycles of denaturation at 95° C. for 20 seconds, annealing at 62° C. for 1 minute, and polymerization at 72° C. for 1 minute; and polymerization at 72° C. for 5 minutes.

(trpE-1)

SEQ ID NO: 74

GAATTCATGCWCACAAWCCGAC (trpE-2)

SEQ ID NO: 75

GAATTCTCAGAAAGTCTCCTGTGCA

Cloning was performed after treating the trpE gene fragment obtained by the above method and the pSG76-C plasmid (*Journal of Bacteriology*, July 1997, p. 4426 to 4428) with EcoRI restriction enzyme, respectively. The cloned plasmid was transformed into *E. coli* DH5α by electroporation, and the transformed *E. coli* DH5α strains were selected on LB plates containing chloramphenicol (25 μg/mL) and thereby the pSG76-C-trpE plasmid was obtained.

A pSG76-C-trpE(P21S) was prepared using the pSG76-C-trpE plasmid obtained above along with the primers of SEQ ID NO: 76 and SEQ ID NO: 77 by site-directed mutagenesis (Stratagene, USA).

```
(trpE(P21S)-1)
                                        SEQ ID NO: 76
CGCTTATCGCGACAATTCCACCGCGCTTTTTCACCAG

(trpE(P21S)-2)
                                        SEQ ID NO: 77
CTGGTGAAAAAGCGCGGTGGAATTGTCGCGATAAGCG
```

The pSG76-C-trpE(P21S) plasmid was transformed into the CA04-9307 strain, cultured in LB-Cm medium (yeast extract 10 g/L, NaCl 5 g/L, tryptone 10 g/L, and chloramphenicol 25 μg/L), and colonies having resistance to chloramphenicol were selected. The selected transformants are strains in which the pSG76-C-trpE(P21S) plasmid is inserted into the trpE region of the genome by first insertion. The strain into which the obtained trpE(P21S) gene is inserted was transformed with the pAScep plasmid (*Journal of Bacteriology*, July 1997, p. 4426 to 4428), which expresses restriction enzyme I-SceI that cleaves the I-SceI regions present in the pSG76-C plasmid, and the strain which grew in the LB-Ap (yeast extract 10 g/L, NaCl 5 g/L, tryptone 10 g/L, and ampicillin 100 μg/L) was selected. The trpE gene in the selected strain was amplified using the primers of SEQ ID NO: 74 and SEQ ID NO: 75, and it was confirmed that the amplified trpE gene was replaced with the trpE(P21S) gene by sequencing. The thus-prepared strain was named as CA04-4303.

EXAMPLE 12

L-Tryptophan Production by Microorganism of the Genus *Escherichia* in Which a Gene Derived From *Herbaspirillum rhizosphaerae* is Introduced The pCL1920-PyccA-Hrh prepared in Example 8 was introduced into the CA04-4303 strain prepared in Reference Example 2, and thereby a CA04-4306 strain in which a gene derived from *Herbaspirillum rhizosphaerae* is overexpressed was prepared. Additionally, the pCL1920 vector, as a control group, was transformed into the CA04-4303 strain. To confirm the amount of L-tryptophan production in the two strains (i.e., CA04-4303/pCL1920 and CA04-4306), these strains were cultured in LB liquid medium containing spectinomycin (50 mg/L) for 12 hours. Then, these strains were each inoculated into a 250 mL corner-baffle flask containing 25 mL of production medium such that the initial $OD_{600}$ value becomes 0.01 and then cultured with shaking at 37° C. at 200 rpm for 48 hours. After completion of the culture, the amount of L-tryptophan production was measured by HPLC.

The results with regard to the L-tryptophan production in CA04-4303/pCL1920 and CA04-4306 strains in medium are shown in Table 5 below. The strain CA04-4306, in which a *Herbaspirillum rhizosphaerae*-derived gene was introduced and overexpressed, showed a final L-tryptophan concentration of 2.1 g/L in the flask cultivation, which is about 50% higher than that of the control group. This indicates that the *Herbaspirillum rhizosphaerae*-derived gene also exports L-tryptophan in *E. coli* and thereby significantly improves its L-tryptophan production.

Production Medium (pH 7.0)

Glucose 70 g, $(NH_4)_2SO_4$ 20 g, $MgSO_4.7H_2O$ 1 g, $KH_2PO_4$ 2 g, Yeast extract 2.5 g, Na-citrate 5 g, NaCl 1 g, $CaCO_3$ 40 g (based on 1 L of distilled water)

TABLE 5

Confirmation of L-tryptophan production in *E. coli*-derived L-tryptophan-producing strain (CA04-4303) and the L-tryptophan-producing strain where the *Herbaspirillum rhizosphaerae*-derived gene is overexpressed (CA04-4306)

| | $OD_{600}$ | Amount of Tryptophan Production (g/L) | Tryptophan Yield (g/g glc, %) |
|---|---|---|---|
| CA04-4303/pCL1920 | 43.7 | 1.4 | 2.0 |
| CA04-4306 | 42 | 2.1 | 3.0 |

Accordingly, as can be seen in the results of Examples 7 and 9, the *Herbaspirillum rhizosphaerae*-derived gene showed high specificity and excellent resistance to L-tryptophan and its analogue. As can be seen in the results of Examples 10 and 12, the *Herbaspirillum rhizosphaerae*-derived gene improved L-tryptophan production in both *Corynebacterium glutamicum* and *E. coli* strains. Additionally, it was observed in Example 11 that the *Herbaspirillum rhizosphaerae*-derived gene substantially exported tryptophan extracellularly. As a result, the *Herbaspirillum rhizosphaerae*-derived gene was named as wex (tryptophan (W) exporter).

EXAMPLE 13

Improvement of Wex Exporting Ability Using Random Mutagenesis

In this Example, error-prone PCR was performed to apply random mutagenesis to the wild-type wex gene, and at the time of performing the error-prone PCR, the Diversify PCR Random Mutagenesis Kit (Clontech, USA) was used.

In order to obtain a variant of the wex gene where random mutagenesis is introduced, the error-prone PCR was performed using the pCL1920-PyccA-wex prepared in Example 8 as a template along with SEQ ID NO: 78 and SEQ ID NO: 79.

For selection of mutation rate conditions, the error-prone PCR was performed with two compositions according to the concentration of $MnSO_4$ as follows.

```
(wex-1)
                                        SEQ ID NO: 78
ACTCTAGAGGATCCCCTTCCAGATCAAATGCGTAA

(wex-2)
                                        SEQ D NO: 79
ATTCGAGCTCGGTACCCCTACAAACAGTCCGCCAC
```

TABLE 6

| Composition for error-prone PCR (Unit: μL) | | |
|---|---|---|
| Case # | 1 | 2 |
| 10X Titanium Taq Buffer | 5 | 5 |
| $MnSO_4$ (8 mM) | 1 | 2 |
| dGTP (2 mM) | 1 | 1 |
| 50X Diversify dNTP Mix | 1 | 1 |
| Titanium Taq Polymerase | 1 | 1 |
| Primer Mix | 2 | 2 |
| Template DNA (1 ng/μL) | 1 | 1 |
| PCR Grade Water | 38 | 37 |
| Total Volume | 50 | 50 |

TABLE 7

| Error-prone PCR cycle | | |
|---|---|---|
| Cycle | Temperature | Time |
| 1 | 94° C. | 30 sec |
| 25 | 94° C. | 30 sec |
| | 68° C. | 1 min |
| 1 | 68° C. | 1 min |

A recombinant mutant plasmid library was obtained by the Gibson assembly method (D G Gibson et al., *Nature Methods*, VOL. 6 NO. 5, MAY 2009, NEBuilder HiFi DNA Assembly Master Mix) using the products of the error-prone PCR (which was performed under the conditions of Table 6 and Table 7) and the pCL1920 (which was cleaved with an SmaI restriction enzyme). The mutant library obtained by the above method, pCL1920-PyccA-Hrh and pCL1920 were transformed into *Escherichia coli* W3110 cells, cultured in an LB plate medium containing spectinomycin (50 μg/L), and 50 colonies were selected from the mutant library. Sequencing was performed to determine their mutation rate and presence/absence of mutation at various positions. As a result of the sequencing, the mutation rate of Case #1 condition was 1.3 kb-1 and that of Case #2 condition was 2.5 kb-1. Both Cases #1 and #2 were determined to meet the mutation rate suitable for obtaining a mutant library, and a process of screening effective mutations was performed using the library prepared under the above conditions.

300 μL of M9 minimal medium containing 50 μg/mL of 5'-fluoro tryptophan (i.e., an L-tryptophan analogue) was aliquoted into each well of a 96 deep-well plate, followed by inoculation of each colony of the previously transformed mutant libraries (i.e., W3110/pCL1920-PyccA-Hrh, W3110/pCL1920, and W3110/pCL1920-PyccA-wex mutant libraries). The culture was performed at 1,200 rpm/37° C., and OD was measured at a 600 nm wavelength after 16 hours of culture. The growth of most mutant libraries was almost not observed in deep well plates as is the case of the control strains (W3110/pCL1920 and W3110/pCL1920-PyccA-Hrh). Among them, 51 colonies with improved growth were selected, and pCL1920-PyccA-wex mutant plasmids were respectively extracted from the colonies and re-transformed into *E. coli* W3110 strains to evaluate reproducibility. 10 Kinds of strains, which showed specific growth improvement in the M9 minimal media, in which 5'-fluoro tryptophan was commonly contained at a concentration of 50 μg/mL, were observed and their ODs were recorded.

TABLE 8

| A wex library in which growth is improved in minimal medium containing L-tryptophan analogue | |
|---|---|
| | Optical Density ($OD_{600}$) |
| W3110/pCL1920 | 0.189 |
| W3110/pCL1920-PyccA-Hrh | 0.393 |
| W3110/pCL1920-PyccA-wex mutant library (1-3 8G) | 0.791 |
| W3110/pCL1920-PyccA-wex mutant library (1-4 6D) | 1.026 |
| W3110/pCL1920-PyccA-wex mutant library (2-1 10C) | 0.748 |
| W3110/pCL1920-PyccA-wex mutant library (2-12 8C) | 0.773 |
| W3110/pCL1920-PyccA-wex mutant library (2-15 6B) | 0.825 |
| W3110/pCL1920-PyccA-wex mutant library (2-18 3F) | 0.921 |
| W3110/pCL1920-PyccA-wex mutant library (3-3 6D) | 0.831 |
| W3110/pCL1920-PyccA-wex mutant library (3-6 11F) | 0.749 |
| W3110/pCL1920-PyccA-wex mutant library (5-5 10B) | 0.766 |
| W3110/pCL1920-PyccA-wex mutant library (5-18 6B) | 0.783 |

After extracting the pCL1920-PyccA-wex mutant plasmid from the 10 selected mutant strains, sequencing was performed to confirm their mutations, and as a result, it was confirmed that the mutations occurred in the coding sequences (CDS), which are not in the promoter regions. Additionally, it was confirmed that the mutation sites in 8 out of the 10 mutant strains were concentrated in a region from the $79^{th}$ amino add (i.e., leucine) to the $83^{rd}$ amino acid (i.e., isoleucine) of the amino acid sequence of the Wex membrane protein, and that most of the mutations were their substitution with a hydrophobic amino add, an aliphatic amino add, or a relatively small L-amino acid. Therefore, it was determined that the positions from 79 to 83 of the amino add sequence of the Wex membrane protein could be a core region for introducing a mutation to improve the L-tryptophan-exporting ability. In this regard, an attempt was made to improve the activity thereof by substituting the amino acid(s) in the corresponding sequence with various hydrophobic amino acid(s), aliphatic amino acid(s), or with relatively small L-amino acid(s).

EXAMPLE 14

Substitution of the $79^{th}$ Amino Acid of Wex Sequence (Leucine) with Hydrophobic Amino Acid in Microorganism of the Genus *Corynebacterium*

An attempt was made to confirm the improved effectiveness of exporting L-tryptophan through the substitution of the $79^{th}$ amino add, leucine (hereinafter, referred to as the leucine at position 79 or at the $79^{th}$ position), in the amino add sequence of the Wex membrane protein with a different hydrophobic amino add. Site-directed mutagenesis was performed using the pDZTn-PgapA-Hrh prepared in Example 2 as a template so as to generate mutations into three different kinds of amino adds other than leucine. The site-directed mutagenesis was performed by the following method.

TABLE 9

| PCR Composition of site-directed mutagenesis | |
|---|---|
| | Unit (μL) |
| 10X pfu-X Buffer | 5 |
| 10 mM dNTP Mix | 1 |
| pfu-X Polymerase | 1 |
| Mutagenic Forward Primer (5 pmol) | 2 |

TABLE 9-continued

| PCR Composition of site-directed mutagenesis | |
|---|---|
| | Unit (μL) |
| Mutagenic Reverse Primer (5 pmol) | 2 |
| pDZTn-PgapA-Hrh (Template DNA, 200 ng/μL) | 1 |
| $dH_2O$ | 38 |
| Total | 50 |

TABLE 10

PCR cycle of site-directed mutagenesis

| Cycle | Temperature | Time |
|---|---|---|
| 1 | 95° C. | 1 min |
| 18 | 95° C. | 50 sec |
| | 60° C. | 50 sec |
| | 68° C. | 9 min |
| 1 | 68° C. | 7 min |

For the substitution of the amino add at position 79 (i.e., leucine) of the Wex amino add sequence with each of the different hydrophobic amino adds (i.e., alanine (A) (SEQ ID NO: 80, SEQ ID NO: 131), valine (V) (SEQ ID NO: 81, SEQ ID NO: 132), and isoleucine (I) (SEQ ID NO: 82, SEQ ID NO: 133)), a PCR mixture was prepared as shown in Table 9 using each mutagenic primer set indicated in Table 11, and PCR was performed following the method shown in Table 10. After completion of the PCR, 1 μL of a DpnI restriction enzyme was added thereto and the mixture was treated at 37° C. for one hour. 3 μL of the DNA treated with DpnI was transformed into DH5a competent cells to obtain mutant pDZTn-PgapA-wex plasmids, and each of the mutations indicated in Table 11 was confirmed by sequencing.

TABLE 11

Mutagenic primer sets for preparation of mutant plasmids, in which the amino acid at position 79 of the Wex amino acid sequence is respectively mutated, for introduction into a microorganism of the genus *Corynebacterium*

| Mutant Wex Plasmid | SEQ ID NO | Nucleotide Sequence |
|---|---|---|
| pDZTn-PgapA-wex L79A | 83 | GTGTCCTACGAACTCTGC**GCA**TCGCTCTCCATCGGTTATG |
| | 84 | CATAACCGATGGAGAGCGA**TGC**GCAGAGTTCGTAGGACAC |
| pDZTn-PgapA-wex L79V | 85 | GTGTCCTACGAACTCTGC**GTG**TCGCTCTCCATCGGTTATG |
| | 86 | CATAACCGATGGAGAGCGA**CAC**GCAGAGTTCGTAGGACAC |
| pDZTn-PgapA-wex L79I | 87 | GTGTCCTACGAACTCTGC**ATC**TCGCTCTCCATCGGTTATG |
| | 88 | CATAACCGATGGAGAGCGA**GAT**GCAGAGTTCGTAGGACAC |

The pDZTn-PgapA-wex L79A, pDZTn-PgapA-wex L79V, and pDZTn-PgapA-wex L791 vectors prepared as shown in Table 11 were each transformed by electroporation into the CA04-8352 strain, which was prepared in Reference Example 1, and then subjected to a secondary crossover to obtain three kinds of strains, in which a mutant wex gene is inserted into the chromosome, respectively. The corresponding genetic manipulation was confirmed through genome sequencing and a PCR method using the primers of SEQ ID NO: 7 and SEQ ID NO: 8, each of which can respectively amplify the external region of the upstream region and downstream region for homologous recombination where the corresponding gene is inserted.

The obtained mutant strains were named as CA04-8352 (wex L79A), CA04-8352(wex L79V), and CA04-8352(wex L791), respectively.

To confirm the amount of tryptophan production in the CA04-8352, CA04-8405, CA04-8352(wex L79A), CA04-8352(wex L79V), and CA04-8352(wex L791) strains, these strains were cultured by the same method as in Example 10. After completion of the culture, the amount of L-tryptophan production in each strain was measured by HPLC.

TABLE 12

Confirmation of amount of L-tryptophan production in *Corynebacterium glutamicum*-derived L-tryptophan-producing strain (CA04-8352), strain (CA04-8405) in which an L-tryptophan-exporting gene (Wex) is inserted, and mutant strains (CA04-8352(wex L79A), CA04-8352(wex L79V), and CA04-8352(wex L79I)), in which the amino acid at position 79 of the Wex amino acid sequence is respectively mutated

| Strain | Amount of Tryptophan Production (g/L) | Tryptophan Yield (g/g glc, %) | Yield Improvement Compared to Wild-type Wex (Δ, % p) |
|---|---|---|---|
| CA04-8352 | 0.25 | 0.83 | — |
| CA04-8405 | 1.52 | 5.07 | — |
| CA04-8352(wex L79A) | 2.41 | 8.02 | 2.95 |
| CA04-8352(wex L79V) | 2.02 | 6.73 | 1.66 |
| CA04-8352(wex L79I) | 2.00 | 6.66 | 1.59 |

As shown in the results of Table 12, all of the three kinds of mutants, in which the leucine at position 79 of the Wex amino add sequence is respectively substituted with a different hydrophobic amino acid, showed an improvement in fermentation yield by 1.59% p to 2.95% p, compared to the CA04-8405 strain, to which the wild-type Wex is introduced. In particular, the wex L79A mutant strain showed the greatest improvement in L-tryptophan fermentation yield, and these results indicate that the substitution of the leucine at position 79 of the Wex amino acid sequence with a different hydrophobic amino acid can significantly increase the activity of L-tryptophan-exporting ability of the Wex.

EXAMPLE 15

Substitution of the 80$^{th}$ Amino Acid of Wex Sequence (Serine) with Hydrophobic Amino Acid in Microorganism of the Genus *Corynebacterium*

An attempt was made to confirm the improved effectiveness of exporting L-tryptophan through the substitution of the 80$^{th}$ amino add, serine (hereinafter, referred to as the serine at position 80), in the amino acid sequence of the Wex membrane protein with a hydrophobic amino acid. Site-directed mutagenesis was performed using the pDZTn-PgapA-wex as a template by the same method as in Example 14 so as to generate mutations into four different kinds of hydrophobic amino adds.

In addition, the serine at position 80 of the Wex amino acid sequence was substituted with each of the different hydrophobic amino acids (i.e., alanine (A) (SEQ ID NO: 89, SEQ ID NO: 134), valine (V) (SEQ ID NO: 90, SEQ ID NO: 135), leucine (L) (SEQ ID NO: 91, SEQ ID NO: 136), and isoleucine (I) (SEQ ID NO: 92, SEQ ID NO: 137)) using the same method as in Example 14. The mutagenic primer sets and the mutation forms used to obtain the pDZTn-PgapA-wex mutant plasmids are the same as shown in Table 13 below.

TABLE 13

Mutagenic primer sets for preparation of mutant plasmids, in which the amino acid at position 80 of the Wex amino acid sequence is respectively mutated, for introduction into a microorganism of the genus *Corynebacterium*

| Mutant Wex Plasmid | SEQ ID NO | Nucleotide Sequence |
|---|---|---|
| pDZTn-PgapA-wex S80A | 93 | GTCCTACGAACTCTGCCTG**GCA**CTCTCCATCGGTTATGCC |
| | 94 | GGCATAACCGATGGAGAG**TGC**CAGGCAGAGTTCGTAGGAC |
| pDZTn-PgapA-wex S80V | 95 | GTCCTACGAACTCTGCCTG**GTG**CTCTCCATCGGTTATGCC |
| | 96 | GGCATAACCGATGGAGAG**CAC**CAGGCAGAGTTCGTAGGAC |
| pDZTn-PgapA-wex S80L | 97 | GTCCTACGAACTCTGCCTG**CTG**CTCTCCATCGGTTATGCC |
| | 98 | GGCATAACCGATGGAGAG**CAG**CAGGCAGAGTTCGTAGGAC |
| pDZTn-PgapA-wex S80I | 99 | GTCCTACGAACTCTGCCTG**ATC**CTCTCCATCGGTTATGCC |
| | 100 | GGCATAACCGATGGAGAG**GAT**CAGGCAGAGTTCGTAGGAC |

The pDZTn-PgapA-wex S80A, pDZTn-PgapA-wex S80V, pDZTn-PgapA-wex S80L, and pDZTn-PgapA-wex S80I vectors, which were prepared as shown in Table 13, were each transformed by electroporation into the CA04-8352 strain, and then subjected to a secondary crossover to obtain four kinds of strains, in which a mutant wex gene is inserted into the chromosome, respectively. The corresponding genetic manipulation was confirmed through genome sequencing and a PCR method using the primers of SEQ ID NO: 7 and SEQ ID NO: 8, each of which can respectively amplify the external region of the upstream region and downstream region for homologous recombination where the corresponding gene is inserted.

The obtained mutant strains were named as CA04-8352 (wex S80A), CA04-8352(wex S80V), CA04-8352(wex S80L), and CA04-8352(wex S80I), respectively.

To confirm the amount of tryptophan production in the CA04-8352, CA04-8405, CA04-8352(wex S80A), CA04-8352(wex S80V), CA04-8352(wex S80L), and CA04-8352 (wex S80I) strains, these strains were cultured by the same method as in Example 10. After completion of the culture, the amount of L-tryptophan production in each strain was measured by HPLC.

TABLE 14

Confirmation of amount of L-tryptophan production in *Corynebacterium glutamicum*-derived L-tryptophan-producing strain (CA04-8352), strain (CA04-8405) in which an L-tryptophan-exporting gene (wex) is inserted, and mutant strains (CA04-8352(wex S80A), CA04-8352(wex S80V), CA04-8352(wex S80L), and CA04-8352(wex S80I)), in which the amino acid at position 80 of the Wex amino acid sequence is respectively mutated

| Strain | Amount of Tryptophan Production (g/L) | Tryptophan Yield (g/g glc, %) | Yield Improvement Compared to Wild-type Wex (Δ, % p) |
|---|---|---|---|
| CA04-8352 | 0.25 | 0.83 | — |
| CA04-8405 | 1.52 | 5.07 | — |
| CA04-8352(wex S80A) | 2.21 | 7.36 | 2.29 |
| CA04-8352(wex S80V) | 2.31 | 7.69 | 2.62 |
| CA04-8352(wex S80L) | 2.28 | 7.61 | 2.54 |
| CA04-8352(wex S80I) | 2.12 | 7.06 | 1.99 |

As shown in the results of Table 14, all of the four kinds of mutants, in which the amino add at position 80 of the Wex amino add sequence is respectively substituted with a different hydrophobic amino acid, showed an improvement in fermentation yield by 1.99% p to 2.62% p, compared to the CA04-8405 strain, to which the wild-type Wex is introduced. In particular, the wex S80V mutant strain showed the greatest improvement in L-tryptophan fermentation yield, and these results indicate that the substitution of the serine at position 80 of the Wex amino add sequence with a different hydrophobic amino add can significantly increase the activity of L-tryptophan-exporting ability of the Wex.

EXAMPLE 16

Substitution of the 81st Amino Acid of Wex Sequence (Leucine) with Hydrophobic Amino Acid in Microorganism of the Genus *Corynebacterium*

An attempt was made to confirm the improved effectiveness of exporting L-tryptophan through the substitution of the 81st amino add, leucine (hereinafter, referred to as the leucine at position 81), in the amino add sequence of the Wex membrane protein with a different hydrophobic amino add. Site-directed mutagenesis was performed using the pDZTn-PgapA-wex as a template by the same method as in Example 14 so as to generate mutations into three different kinds of hydrophobic amino adds other than leucine.

In addition, the leucine at position 81 of the Wex amino acid sequence was substituted with each of the different hydrophobic amino acids (i.e., alanine (A) (SEQ ID NO: 101, SEQ ID NO: 138), valine (V) (SEQ ID NO: 102, SEQ ID NO: 139), and isoleucine (I) (SEQ ID NO: 103, SEQ ID NO: 140)) using the same method as in Example 14. The mutagenic primer sets and the mutation forms used to obtain the pDZTn-PgapA-wex mutant plasmids are the same as shown in Table 15 below.

TABLE 15

Mutagenic primer sets for preparation of mutant plasmids, in which the amino acid at position 81 of the Wex amino acid sequence is respectively mutated, for introduction into microorganism of the genus *Corynebacterium*

| Mutant Wex Plasmid | SEQ ID NO | Nucleotide Sequence |
|---|---|---|
| pDZTn-PgapA-wex L81A | 104 | CCTACGAACTCTGCCTGTCG**GCA**TCCATCGGTTATGCCAATAC |
| | 105 | GTATTGGCATAACCGATGGA**TGC**CGACAGGCAGAGTTCGTAGG |
| pDZTn-PgapA-wex L81V | 106 | CCTACGAACTCTGCCTGTCG**GTG**TCCATCGGTTATGCCAATAC |
| | 107 | GTATTGGCATAACCGATGGA**CAC**CGACAGGCAGAGTTCGTAGG |
| pDZTn-PgapA-wex L81I | 108 | CCTACGAACTCTGCCTGTCG**ATC**TCCATCGGTTATGCCAATAC |
| | 109 | GTATTGGCATAACCGATGGA**GAT**CGACAGGCAGAGTTCGTAGG |

The pDZTn-PgapA-wex L81A, pDZTn-PgapA-wex L81V, and pDZTn-PgapA-wex L81I vectors prepared as shown in Table 15 were each transformed by electroporation into the CA04-8352 strain, and then subjected to a secondary crossover to obtain three kinds of strains, in which a mutant wex gene is inserted into the chromosome, respectively. The corresponding genetic manipulation was confirmed through genome sequencing and a PCR method using the primers of SEQ ID NO: 7 and SEQ ID NO: 8, each of which can respectively amplify the external region of the upstream region and downstream region for homologous recombination where the corresponding gene is inserted.

The obtained mutant strains were named as CA04-8352 (wex L81A), CA04-8352(wex L81V), and CA04-8352(wex L81I), respectively.

To confirm the amount of tryptophan production in CA04-8352, CA04-8405, CA04-8352(wex L81A), CA04-8352 (wex L81V), and CA04-8352(wex L81I), these strains were cultured by the same method as in Example 10. After completion of the culture, the amount of L-tryptophan production in each strain was measured by HPLC.

TABLE 16

Confirmation of amount of L-tryptophan production in *Corynebacterium glutamicum*-derived L-tryptophan-producing strain (CA04-8352), strain (CA04-8405) in which an L-tryptophan-exporting gene (wex) is inserted, and mutant strains (CA04-8352(wex L81A), CA04-8352(wex L81V), and CA04-8352(wex L81I)), in which the amino acid at position 81 of the Wex amino acid sequence is respectively mutated

| Strain | Amount of Tryptophan Production (g/L) | Tryptophan Yield (g/g glc, %) | Yield Improvement Compared to Wild-type Wex (Δ, % p) |
|---|---|---|---|
| CA04-8352 | 0.25 | 0.83 | — |
| CA04-8405 | 1.52 | 5.07 | — |
| CA04-8352(wex L81A) | 2.38 | 7.94 | 2.87 |
| CA04-8352(wex L81V) | 2.13 | 7.10 | 2.03 |
| CA04-8352(wex L81I) | 2.21 | 7.36 | 2.29 |

As shown in the results of Table 16, all of the three kinds of mutants, in which the amino acid at position 81 of the Wex amino add sequence is respectively substituted with a different hydrophobic amino acid, showed an improvement in fermentation yield by 2.03% p to 2.87% p, compared to the CA04-8405 strain, to which the wild-type Wex is introduced. In particular, the wex L81A mutant strain showed the greatest improvement in L-tryptophan fermentation yield, and these results indicate that the substitution of the leucine at position 81 of the Wex amino acid sequence with a different hydrophobic amino acid can significantly increase the activity of L-tryptophan-exporting ability of the Wex.

EXAMPLE 17

Substitution of the 82nd Amino Acid of Wex Sequence (Serine) with Hydrophobic Amino Acid in Microorganism of the Genus *Corynebacterium*

An attempt was made to confirm the improved effectiveness of exporting L-tryptophan through the substitution of the 82nd amino add, serine (hereinafter, the serine at position 82), in the amino add sequence of the Wex membrane protein with a hydrophobic amino add. Site-directed mutagenesis was performed using the pDZTn-PgapA-wex as a template by the same method as in Example 14 so as to generate mutations into four different kinds of hydrophobic amino adds.

In addition, the serine at position 82 of the Wex amino add sequence was substituted with each of the different hydrophobic amino acids (i.e., alanine (A) (SEQ ID NO: 110, SEQ ID NO: 141), valine (V) (SEQ ID NO: 111, SEQ ID NO: 142), leucine (L) (SEQ ID NO: 112, SEQ ID NO: 143), and isoleucine (I) (SEQ ID NO: 113, SEQ ID NO: 144)) using the same method as in Example 14. The mutagenic primer sets and the mutation forms used to obtain the pDZTn-PgapA-wex mutant plasmids are the same as shown in Table 17 below.

TABLE 17

Mutagenic primer sets for preparation of mutant plasmids, in which the amino acid at position 82 of the Wex amino acid sequence is respectively mutated, for introduction into a microorganism of the genus *Corynebacterium*

| Mutant Wex Plasmid | SEQ ID NO | Nucleotide Sequence |
|---|---|---|
| pDZTn-PgapA-wex S82A | 114 | CGAACTCTGCCTGTCGCTC**GCA**ATCGGTTATGCCAATACAG |
| | 115 | CTGTATTGGCATAACCGAT**TGC**GAGCGACAGGCAGAGTTCG |
| pDZTn-PgapA-wex S82V | 116 | CGAACTCTGCCTGTCGCTC**GTG**ATCGGTTATGCCAATACAG |
| | 117 | CTGTATTGGCATAACCGA**TCAC**GAGCGACAGGCAGAGTTCG |
| pDZTn-PgapA-wex S82L | 118 | CGAACTCTGCCTGTCGCTC**CTG**ATCGGTTATGCCAATACAG |
| | 119 | CTGTATTGGCATAACCGAT**CAG**GAGCGACAGGCAGAGTTCG |
| pDZTn-PgapA-wex S82I | 120 | CGAACTCTGCCTGTCGCT**CATC**ATCGGTTATGCCAATACAG |
| | 121 | CTGTATTGGCATAACCGAT**GAT**GAGCGACAGGCAGAGTTCG |

The pDZTn-PgapA-wex S82A, pDZTn-PgapA-wex S82V, pDZTn-PgapA-wex S82L, and pDZTn-PgapA-wex S82I vectors prepared as shown in Table 17 were each transformed by electroporation into the CA04-8352 strain, and then subjected to a secondary crossover to obtain four kinds of strains, in which a mutant wex gene is inserted into the chromosome, respectively. The corresponding genetic manipulation was confirmed through genome sequencing and a PCR method using the primers of SEQ ID NO: 7 and SEQ ID NO: 8, each of which can respectively amplify the external region of the upstream region and downstream region for homologous recombination where the corresponding gene is inserted.

The obtained mutant strains were named as CA04-8352 (wex S82A), CA04-8352(wex S82V), CA04-8352(wex S82L), and CA04-8352(wex S82I), respectively.

To confirm the amount of tryptophan production in the CA04-8352, CA04-8405, CA04-8352(wex S82A), CA04-8352(wex S82V), CA04-8352(wex S82L), and CA04-8352 (wex S82I) strains, these strains were cultured by the same method as in Example 10. After completion of the culture, the amount of L-tryptophan production in each strain was measured by HPLC.

TABLE 18

Confirmation of amount of L-tryptophan production in *Corynebacterium glutanicum*-derived L-tryptophan-producing strain (CA04-8352), strain (CA04-8405) in which an L-tryptophan-exporting gene (wex) is inserted, and mutant strains (CA04-8352(wex S82A), CA04-8352(wex S82V), CA04-8352(wex S82L), and CA04-8352(wex S82I)), in which the amino acid at position 82 of the Wex amino acid sequence is respectively mutated

| Strain | Amount of Tryptophan Production (g/L) | Tryptophan Yield (g/g glc, %) | Yield Improvement Compared to Wild-type Wex (Δ, % p) |
|---|---|---|---|
| CA04-8352 | 0.25 | 0.83 | — |
| CA04-8405 | 1.52 | 5.07 | — |
| CA04-8352(wex S82A) | 2.35 | 7.83 | 2.76 |
| CA04-8352(wex S82V) | 2.18 | 7.28 | 2.21 |
| CA04-8352(wex S82L) | 1.94 | 6.47 | 1.40 |
| CA04-8352(wex S82I) | 2.00 | 6.66 | 1.59 |

As shown in the results of Table 18, all of the four kinds of mutants, in which the amino add at position 82 of the Wex amino add sequence is respectively substituted with a different hydrophobic amino acid, showed an improvement in fermentation yield by 1.40% p to 2.76% p, compared to the CA04-8405 strain, to which the wild-type Wex is introduced. In particular, the wex S82A mutant strain showed the greatest improvement in L-tryptophan fermentation yield, and these results indicate that the substitution of the serine at position 82 of the Wex amino add sequence with a different hydrophobic amino add can significantly increase the activity of L-tryptophan-exporting ability of the Wex.

EXAMPLE 18

Substitution of the 83$^{rd}$ Amino Acid of Wex Sequence (Isoleucine) with Hydrophobic Amino Acid in Microorganism of the Genus *Corynebacterium*

An attempt was made to confirm the improved effectiveness of exporting L-tryptophan through the substitution of the 83$^{rd}$ amino add, isoleucine (hereinafter, referred to as the isoleucine at position 83), in the amino add sequence of the Wex membrane protein with a different hydrophobic amino add. Site-directed mutagenesis was performed using the pDZTn-PgapA-wex as a template by the same method as in Example 14 so as to generate mutations into three different kinds of hydrophobic amino adds other than isoleucine.

In addition, the isoleucine at position 83 of the Wex amino add sequence was substituted with each of the different hydrophobic amino acids (i.e., alanine (A) (SEQ ID NO: 122, SEQ ID NO: 145), valine (V) (SEQ ID NO: 123, SEQ ID NO: 146), and leucine (L) (SEQ ID NO: 124, SEQ ID NO: 147)) using the same method as in Example 14. The mutagenic primer sets and the mutation forms used to obtain the pDZTn-PgapA-wex mutant plasmids are the same as shown in Table 19 below.

TABLE 19

Mutagenic primer sets for preparation of mutant plasmids, in which the amino acid at position 83 of the Wex amino acid sequence is respectively mutated, for introduction into a microorganism of the genus *Corynebacterium*

| Mutant Wex Plasmid | SEQ ID NO | Nucleotide Sequence |
|---|---|---|
| pDZTn-PgapA-wex I83A | 125 | GAACTCTGCCTGTCGCTCTCC**GCA**GGTTATGCCAATACAGGCAGG |
| | 126 | CCTGCCTGTATTGGCATAACC**TGC**GGAGAGCGACAGGCAGAGTTC |
| pDZTn-PgapA-wex I83V | 127 | GAACTCTGCCTGTCGCTCTCC**GTG**GGTTATGCCAATACAGGCAGG |
| | 128 | CCTGCCTGTATTGGCATAACC**CAC**GGAGAGCGACAGGCAGAGTTC |
| pDZTn-PgapA-wex I83L | 129 | GAACTCTGCCTGTCGCTCTCC**CTG**GGTTATGCCAATACAGGCAGG |
| | 130 | CCTGCCTGTATTGGCATAACC**CAG**GGAGAGCGACAGGCAGAGTTC |

The pDZTn-PgapA-wex I83A, pDZTn-PgapA-wex I83V, and pDZTn-PgapA-wex I83L vectors prepared as shown in Table 19 were each transformed by electroporation into the CA04-8352 strain, and then subjected to a secondary crossover to obtain three kinds of strains, in which a mutant wex gene is inserted into the chromosome, respectively. The corresponding genetic manipulation was confirmed through genome sequencing and a PCR method using the primers of SEQ ID NO: 7 and SEQ ID NO: 8, each of which can respectively amplify the external region of the upstream region and downstream region for homologous recombination where the corresponding gene is inserted.

The obtained mutant strains were named as CA04-8352 (wex I83A), CA04-8352(wex I83V), and CA04-8352(wex I83L), respectively.

To confirm the amount of tryptophan production in the CA04-8352, CA04-8405, CA04-8352(wex I83A), CA04-8352(wex I83V), and CA04-8352(wex I83L) strains, these strains were cultured by the same method as in Example 10. After completion of the culture, the amount of L-tryptophan production in each strain was measured by HPLC.

TABLE 20

Confirmation of amount of L-tryptophan production in *Corynebacterium glutamicum*-derived L-tryptophan-producing strain (CA04-8352), strain (CA04-8405) into which an L-tryptophan-exporting gene (wex) is inserted, and mutant strains (CA04-8352(wex I83A), CA04-8352(wex I83V), and CA04-8352(wex I83L)), in which the amino acid at position 83 of the Wex amino acid sequence is respectively mutated

| Strain | Amount of Tryptophan Production (g/L) | Tryptophan Yield (g/g glc, %) | Yield Improvement Compared to Wild-type Wex (Δ, % p) |
|---|---|---|---|
| CA04-8352 | 0.25 | 0.83 | — |
| CA04-8405 | 1.52 | 5.07 | — |
| CA04-8352(wex I83A) | 2.04 | 6.80 | 1.73 |
| CA04-8352(wex I83V) | 2.22 | 7.39 | 2.32 |
| CA04-8352(wex I83L) | 2.23 | 7.43 | 2.36 |

As shown in the results of Table 20, all of the three kinds of mutants, in which the amino acid at position 83 of the Wex amino add sequence is respectively substituted with a different hydrophobic amino acid, showed an improvement in fermentation yield by 1.73% p to 2.36% p, compared to the CA04-8405 strain, to which the wild-type Wex is introduced. In particular, the wex 183 L mutant strain showed the greatest improvement in L-tryptophan fermentation yield, and these results indicate that the substitution of the isoleucine at position 83 of the Wex amino add sequence with a different hydrophobic amino acid can significantly increase the activity of L-tryptophan-exporting ability of the Wex. Through the results shown in Examples 2-6 above, it was confirmed that the substitution of the amino adds at positions from 79 to 83 in the amino add sequence of the Wex membrane protein with a different hydrophobic amino acid can significantly increase the activity of L-tryptophan-exporting ability in a *Corynebacterium glutamicum* strain.

The CA04-8352(wex L79I), CA04-8352(wex S80V), CA04-8352(wex L81V), CA04-8352(wex S82V), and CA04-8352(wex I83L) strains, into which the mutant wex of the present disclosure is introduced, were named as CM05-9022, CM05-9023, CM05-9024, CM05-9025, and CM05-9026, respectively. These strains were internationally deposited at the Korean Culture Center of Microorganisms (KCCM), an international depositary, on Mar. 29, 2019, under the provisions of the Budapest Treaty and assigned accession numbers KCCM12475P, KCCM12476P, KCCM12477P, KCCM12478P, and KCCM12479P, respectively.

EXAMPLE 19

Substitution of the Amino Acid at Position 79 of Wex Sequence (Leucine) with Hydrophobic Amino Acid in Microorganism of the Genus *Escherichia*

The effect of improving the activity of L-tryptophan-exporting ability according to the introduction of Wex mutation in a microorganism of the genus *Corynebacterium* shown in Examples 14 to 18 above was confirmed again in a microorganism of the genus *Escherichia*.

As in the microorganism of the genus *Corynebacterium*, an attempt was made in a microorganism of the genus *Escherichia* to confirm the improved effectiveness of exporting L-tryptophan through the substitution of the amino acid at position 79 (i.e., leucine) in the amino add sequence of the Wex membrane protein with a different hydrophobic amino add. Site-directed mutagenesis was performed using the pCL1920-PyccA-Hrh prepared in Example 8 as a template so as to generate mutations into three different kinds of hydrophobic amino adds other than leucine. The site-directed mutagenesis was performed by the following method.

TABLE 21

PCR Composition of site-directed mutagenesis

| | Unit (μL) |
|---|---|
| 10X pfu-X Buffer | 5 |
| 10 mM dNTP Mix | 1 |
| pfu-X Polymerase | 1 |
| Mutagenic Forward Primer (5 pmol) | 2 |
| Mutagenic Reverse Primer (5 pmol) | 2 |
| pDZTn-PgapA-Hrh (template DNA, 200 ng/μL) | 1 |
| $dH_2O$ | 38 |
| Total | 50 |

TABLE 22

PCR cycle of site-directed mutagenesis

| Cycle | Temperature | Time |
|---|---|---|
| 1 | 95° C. | 1 min |
| 18 | 95° C. | 50 sec |
| | 60° C. | 50 sec |
| | 68° C. | 6 min |
| 1 | 68° C. | 7 min |

For the substitution of the amino add at position 79 of the Wex amino acid sequence (i.e., leucine) with each of the different hydrophobic amino acids (i.e., alanine (A) (SEQ ID NO: 80, SEQ ID NO: 131), valine (V) (SEQ ID NO: 81, SEQ ID NO: 132), and isoleucine (I) (SEQ ID NO: 82, SEQ ID NO: 133)), a PCR mixture was prepared as shown in Table 21 using each mutagenic primer set indicated in Table 23, and PCR was performed following the method shown in Table 22. After completion of PCR, 1 μL of a DpnI restriction enzyme was added thereto and the mixture was treated at 37° C. for one hour. 3 μL of the DNA treated with DpnI was transformed into DH5a competent cells to obtain mutant pCL1920-PgapA-wex plasmids, and each of the mutations indicated in Table 23 was confirmed by sequencing.

TABLE 23

Mutagenic primer sets for preparation of mutant plasmids, in which the amino acid at position 79 of the Wex amino acid sequence is respectively mutated, for expression in a microorganism of the genus *Escherichia*

| Mutant Wex Plasmid | SEQ ID NO | Nucleotide Sequence |
|---|---|---|
| pCL1920-PyccA-wex L79A | 83 | GTGTCCTACGAACTCTGC**GCA**TCGCTCT CCATCGGTTATG |
| | 84 | CATAACCGATGGAGAGCGA**TGC**GCAGA GTTCGTAGGACAC |
| pCL1920-PyccA-wex L79V | 85 | GTGTCCTACGAACTCTGC**GTG**TCGCTCT CCATCGGTTATG |
| | 86 | CATAACCGATGGAGAGCGA**CAC**GCAGA GTTCGTAGGACAC |

TABLE 23-continued

Mutagenic primer sets for preparation of mutant plasmids, in which the amino acid at position 79 of the Wex amino acid sequence is respectively mutated, for expression in a microorganism of the genus *Escherichia*

| Mutant Wex Plasmid | SEQ ID NO | Nucleotide Sequence |
|---|---|---|
| pCL1920-PyccA-wex L79I | 87 | GTGTCCTACGAACTCTGC**ATC**TCGCTCT CCATCGGTTATG |
| | 88 | CATAACCGATGGAGAGCGA**GAT**GCAGA GTTCGTAGGACAC |

The pCL1920-PyccA-wex L79A, pCL1920-PyccA-wex L79V, and pCL1920-PyccA-wex L79I vectors prepared as shown in Table 23 were each transformed by electroporation into the CA04-4303 strain, and thereby, three kinds of strains where each of the mutant wex genes that differ from one another in the amino add at position 79 is introduced were obtained. The obtained mutant strains were named as CA04-4303(wex L79A), CA04-4303(wex L79V), and CA04-4303 (wex L79I), respectively.

To confirm the amount of tryptophan production in the CA04-4303(wex L79A), CA04-4303(wex L79V), and CA04-4303(wex L79I) strains, using the CA04-4303 (pCL1920) and CA04-4306 strains prepared in Example 12 as the control groups, these strains were cultured by the same method in Example 12. After completion of the culture, the amount of L-tryptophan production in each strain was measured by HPLC.

TABLE 24

Confirmation of amount of L-tryptophan production in *E. coli*-derived L-tryptophan-producing strain (CA04-4303(pCL1920)), strain (CA04-4306) in which an L-tryptophan-exporting gene (wex) is expressed, and mutant strains (CA04-4303(wex L79A), CA04-4303(wex L79V), and CA04-4303(wex L79I)), in which the amino acid at position 79 of the Wex amino add sequence is respectively mutated

| Strain | Amount of Tryptophan Production (g/L) | Tryptophan Yield (g/g glc, %) | Yield Improvement Compared to Wild-type Wex (Δ, % p) |
|---|---|---|---|
| CA04-4303(pCL1920) | 1.4 | 2.0 | — |
| CA04-4306 | 2.1 | 3.0 | — |
| CA04-4303(wex L79A) | 3.2 | 4.5 | 1.5 |
| CA04-4303(wex L79V) | 2.5 | 3.6 | 0.6 |
| CA04-4303(wex L79I) | 2.7 | 3.9 | 0.9 |

As shown in the results of Table 24, all of the three kinds of mutants, in which the amino acid at position 79 of the Wex amino add sequence is respectively substituted with a different hydrophobic amino acid, showed an improvement in fermentation yield by 0.6% p to 1.5% p, compared to the CA04-4306 strain, to which the wild-type Wex is introduced. In particular, as in the L-tryptophan-producing strain of *Corynebacterium glutamicum*, the *E. coli* strain with a wex L79A mutation also showed the greatest improvement in L-tryptophan fermentation yield, and these results indicate that the substitution of the leucine at position 79 of the Wex amino add sequence with a different hydrophobic amino add can significantly increase the activity of L-tryptophan-exporting ability of the Wex in a microorganism of the genus *Escherichia* as well as in a microorganism of the genus *Corynebacterium.*

EXAMPLE 20

Substitution of the Amino Acid at Position 80 of Wex Sequence (Serine) with Hydrophobic Amino Acid in Microorganism of the Genus *Escherichia*

An attempt was made to confirm the improved effectiveness of exporting L-tryptophan through the substitution of the serine at position 80 in the amino acid sequence of the Wex membrane protein with a different hydrophobic amino add in a microorganism of the genus *Escherichia*. Site-directed mutagenesis was performed using the pCL1920-PyccA-wex as a template by the same method as in Example 19 so as to generate mutations into four different kinds of hydrophobic amino adds.

In addition, the serine at position 80 of the Wex amino acid sequence was substituted with each of the different hydrophobic amino acids (i.e., alanine (A) (SEQ ID NO: 89, SEQ ID NO: 134), valine (V) (SEQ ID NO: 90, SEQ ID NO: 135), leucine (L) (SEQ ID NO: 91, SEQ ID NO: 136), and isoleucine (I) (SEQ ID NO: 92, SEQ ID NO: 137)) using the same method as in Example 19. The mutagenic primer sets and the mutation forms used to obtain the mutant pCL1920-PyccA-wex plasmids are the same as shown in Table 25 below.

TABLE 25

Mutagenic primer sets for preparation of mutant plasmids, in which the amino acid at position 80 of the Wex amino acid sequence is respectively mutated, for expression in a microorganism of the genus *Escherichia*

| Mutant Wex Plasmid | SEQ ID NO | Nucleotide Sequence |
|---|---|---|
| pCL1920-PyccA-wex S80A | 93 | GTCCTACGAACTCTGCCTG**GCA**CTCTC CATCGGTTATGCC |
| | 94 | GGCATAACCGATGGAGAG**TGC**CAGGC AGAGTTCGTAGGAC |
| pCL1920-PyccA-wex S80V | 95 | GTCCTACGAACTCTGCCTG**GTG**CTCTC CATCGGTTATGCC |
| | 96 | GGCATAACCGATGGAGAG**CAC**CAGGC AGAGTTCGTAGGAC |
| pCL1920-FVccA-wex S80L | 97 | GTCCTACGAACTCTGCCTG**CTG**CTCTC CATCGGTTATGCC |
| | 98 | GGCATAACCGATGGAGAG**CAG**CAGGC AGAGTTCGTAGGAC |
| pCL1920-PyccA-wex S80I | 99 | GTCCTACGAACTCTGCCTG**ATC**CTCTC CATCGGTTATGCC |
| | 100 | GGCATAACCGATGGAGAG**GAT**CAGGC AGAGTTCGTAGGAC |

The pCL1920-PyccA-wex S80A, pCL1920-PyccA-wex S80V, pCL1920-PyccA-wex S80L, and pCL1920-PyccA-wex S80I vectors prepared as shown in Table 25 were each transformed by electroporation into the CA04-4303 strain, and thereby, four kinds of strains where each of the mutant wex genes that differ from one another in the amino add at position 80 is introduced were obtained. The obtained mutant strains were named as CA04-4303(wex S80A), CA04-4303(wex S80V), CA04-4303(wex S80L), and CA04-4303(wex S80I), respectively.

To confirm the amount of tryptophan production in the CA04-4303(pCL1920), CA04-4306, CA04-4303(wex S80A), CA04-4303(wex S80V), CA04-4303(wex S80L), and CA04-4303(wex S80I) strains, these strains were cultured by the same method in Example 12. After completion of the culture, the amount of L-tryptophan production in each strain was measured by HPLC.

TABLE 26

Confirmation of amount of L-tryptophan production in *E. coli*-derived L-tryptophan-producing strain (CA04-4303(pCL1920)), strain (CA04-4306) in which an L-tryptophan-exporting gene (wex) is expressed, and mutant strains (CA04-4303(wex S80A), CA04-4303(wex S80V), CA04-4303(wex S80L), and CA04-4303(wex S80I)), in which the amino acid at position 80 of the Wex amino acid sequence is respectively mutated

| Strain | Amount of Tryptophan Production (g/L) | Tryptophan Yield (g/g glc, %) | Yield Improvement Compared to Wild-type Wex (Δ, % p) |
|---|---|---|---|
| CA04-4303(pCL1920) | 1.4 | 2.0 | — |
| CA04-4306 | 2.1 | 3.0 | — |
| CA04-4303(wex S80A) | 2.7 | 3.9 | 0.9 |
| CA04-4303(wex S80V) | 2.9 | 4.2 | 1.2 |
| CA04-4303(wex S80L) | 2.6 | 3.7 | 0.7 |
| CA04-4303(wex S80I) | 2.3 | 3.3 | 0.3 |

As shown in the results of Table 26, all of the four kinds of mutants, in which the amino add at position 80 of the Wex amino add sequence is respectively substituted with a different hydrophobic amino acid, showed an improvement in fermentation yield by 0.3% p to 1.2% p, compared to the CA04-4306 strain, to which the wild-type Wex is introduced. In particular, as in the L-tryptophan-producing strain of *Corynebacterium glutamicum*, the *E. coli* strain with a wex S80V mutation also showed the greatest improvement in L-tryptophan fermentation yield, and these results indicate that the substitution of the serine at position 80 of the Wex amino add sequence with a different hydrophobic amino add can significantly increase the activity of L-tryptophan-exporting ability of the Wex in a microorganism of the genus *Escherichia* as well as in a microorganism of the genus *Corynebacterium.*

EXAMPLE 21

Substitution of the Amino Acid at Position 81 of Wex Sequence (Leucine) with Hydrophobic Amino Acid in Microorganism of the Genus *Escherichia*

An attempt was made to confirm the improved effectiveness of exporting L-tryptophan through the substitution of the leucine at position 81 in the amino add sequence of the Wex membrane protein with a different hydrophobic amino add in a microorganism of the genus *Escherichia*. Site-directed mutagenesis was performed using the pCL1920-PyccA-wex as a template by the same method as in Example 19 so as to generate mutations into three different kinds of hydrophobic amino acids other than leucine.

In addition, the leucine at position 81 of the Wex amino acid sequence was substituted with each of the different hydrophobic amino acids (i.e., alanine (A) (SEQ ID NO: 101, SEQ ID NO: 138), valine (V) (SEQ ID NO: 102, SEQ ID NO: 139), and isoleucine (I) (SEQ ID NO: 103, SEQ ID NO: 140)) using the same method as in Example 19. The mutagenic primer sets and the mutation forms used to obtain the mutant pCL1920-PyccA-wex plasmids are the same as shown in Table 27 below.

TABLE 27

Mutagenic primer sets for preparation of mutant plasmids, in which the amino acid at position 81 of Wex amino acid sequence is respectively mutated, for expression in microorganism of the genus *Escherichia*

| Mutant Wex Plasmid | SEQ ID NO | Nucleotide Sequence |
|---|---|---|
| pCL1920-PyccA-wex L81A | 104 | CCTACGAACTCTGCCTGTCG**GCA**TCCATCGGTTATGCCAATAC |
| | 105 | GTATTGGCATAACCGATGGA**TGC**CGACAGGCAGAGTTCGTAGG |
| pCL1920-PyccA-wex L81V | 106 | CCTACGAACTCTGCCTGTCG**GTG**TCCATCGGTTATGCCAATAC |
| | 107 | GTATTGGCATAACCGATGGA**CAC**CGACAGGCAGAGTTCGTAGG |
| pCL1920-PyccA-wex L81I | 108 | CCTACGAACTCTGCCTGTCG**ATC**TCCATCGGTTATGCCAATAC |
| | 109 | GTATTGGCATAACCGATGGA**GAT**CGACAGGCAGAGTTCGTAGG |

The pCL1920-PyccA-wex L81A, pCL1920-PyccA-wex L81V, and pCL1920-PyccA-wex L81I vectors prepared as shown in Table 27 were each transformed by electroporation into the CA04-4303 strain, and thereby, three kinds of strains where each of the mutant wex genes that differ from one another in the amino add at position 81 is introduced were obtained. The obtained mutant strains were named as CA04-4303(wex L81A), CA04-4303(wex L81V), and CA04-4303 (wex L81I), respectively.

To confirm the amount of tryptophan production in the CA04-4303(pCL1920), CA04-4306, CA04-4303(wex L81A), CA04-4303(wex L81V), and CA04-4303(wex L81I) strains, these strains were cultured by the same method in Example 12. After completion of the culture, the amount of L-tryptophan production in each strain was measured by HPLC.

TABLE 28

Confirmation of amount of L-tryptophan production in E. coli-derived L-tryptophan-producing strain (CA04-4303 (pCL1920)), strain (CA04-4306) in which an L-tryptophan-exporting gene (wex) is expressed, and mutant strains (CA04-4303(wex L81A), CA04-4303(wex L81V), and CA04-4303(wex L81I)), in which the amino acid at position 81 of the Wex amino acid sequence is respectively mutated

| Strain | Amount of Tryptophan Production (g/L) | Tryptophan Yield (g/g glc, %) | Yield Improvement Compared to Wild-type Wex (Δ, %p) |
|---|---|---|---|
| CA04-4303 (pCL1920) | 1.4 | 2.0 | — |
| CA04-4306 | 2.1 | 3.0 | — |
| CA04-4303 (wex L81A) | 3.4 | 4.8 | 1.8 |

TABLE 28-continued

Confirmation of amount of L-tryptophan production in E. coli-derived L-tryptophan-producing strain (CA04-4303 (pCL1920)), strain (CA04-4306) in which an L-tryptophan-exporting gene (wex) is expressed, and mutant strains (CA04-4303(wex L81A), CA04-4303(wex L81V), and CA04-4303(wex L81I)), in which the amino acid at position 81 of the Wex amino acid sequence is respectively mutated

| Strain | Amount of Tryptophan Production (g/L) | Tryptophan Yield (g/g glc, %) | Yield Improvement Compared to Wild-type Wex (Δ, %p) |
|---|---|---|---|
| CA04-4303 (wex L81V) | 2.9 | 4.1 | 1.1 |
| CA04-4303 (wex L81I) | 2.8 | 4.0 | 1.0 |

As shown in the results of Table 28, all of the three kinds of mutants, in which the amino acid at position 81 of the Wex amino add sequence is respectively substituted with a different hydrophobic amino acid, showed an improvement in fermentation yield by 1.0% p to 1.8% p, compared to the CA04-4306 strain, to which the wild-type Wex is introduced. In particular, as in the L-tryptophan-producing strain of *Corynebacterium glutamicum*, the *E. coli* strain with a wex L81A mutation also showed the greatest improvement in L-tryptophan fermentation yield, and these results indicate that the substitution of the leucine at position 81 of the Wex amino add sequence with a different hydrophobic amino add can significantly increase the activity of L-tryptophan-exporting ability of the Wex in a microorganism of the genus *Escherichia* as well as in a microorganism of the genus *Corynebacterium.*

EXAMPLE 22

Substitution of the Amino Acid at Position 82 of Wex Sequence (Serine) with Hydrophobic Amino Acid in Microorganism of the Genus *Escherichia*

An attempt was made to confirm the improved effectiveness of exporting L-tryptophan through the substitution of the amino add at position 82 (i.e., serine) in the amino add sequence of the Wex membrane protein with a different hydrophobic amino add in a microorganism of the genus *Escherichia*. Site-directed mutagenesis was performed using the pCL1920-PyccA-wex as a template by the same method as in Example 19 so as to generate mutations into four different kinds of hydrophobic amino adds.

In addition, the serine at position 82 of the Wex amino acid sequence was substituted with each of the different hydrophobic amino acids (i.e., alanine (A) (SEQ ID NO: 110, SEQ ID NO: 141), valine (V) (SEQ ID NO: 111, SEQ ID NO: 142), leucine (L) (SEQ ID NO: 112, SEQ ID NO: 143), and isoleucine (I) (SEQ ID NO: 113, SEQ ID NO: 144)) using the same method as in Example 19. The mutagenic primer sets and the mutation forms used to obtain the mutant pCL1920-PyccA-wex plasmids are the same as shown in Table 29 below.

TABLE 29

Mutagenic primer sets for preparation of mutant plasmids, in which the amino acid at position 82 of Wex amino acid sequence is respectively mutated, for expression in microorganism of the genus *Escherichia*

| Mutant Wex Plasmid | SEQ ID NO | Nucleotide Sequence |
|---|---|---|
| pCL1920-PyccA-wex S82A | 114 | CGAACTCTGCCTGTCGCTC**GCA**ATCGGTTATGCCAATACAG |
| | 115 | CTGTATTGGCATAACCGAT**TGC**GAGCGACAGGCAGAGTTCG |
| pCL1920-PyccA-wex S82V | 116 | CGAACTCTGCCTGTCGCTC**GTG**ATCGGTTATGCCAATACAG |
| | 117 | CTGTATTGGCATAACCGAT**CAC**GAGCGACAGGCAGAGTTCG |
| pCL1920-PyccA-wex S82L | 118 | CGAACTCTGCCTGTCGCTC**CTG**ATCGGTTATGCCAATACAG |
| | 119 | CTGTATTGGCATAACCGAT**CAG**GAGCGACAGGCAGAGTTCG |
| pCL1920-PyccA-wex S82I | 120 | CGAACTCTGCCTGTCGCTC**ATC**ATCGGTTATGCCAATACAG |
| | 121 | CTGTATTGGCATAACCGAT**GAT**GAGCGACAGGCAGAGTTCG |

The pCL1920-PyccA-wex S82A, pCL1920-PyccA-wex S82V, pCL1920-PyccA-wex S82L, and pCL1920-PyccA-wex S82I vectors prepared as shown in Table 29 were each transformed by electroporation into the CA04-4303 strain, and thereby, four kinds of strains where each of the mutant wex genes that differ from one another in the amino add at position 82 is introduced were obtained. The obtained mutant strains were named as CA04-4303(wex S82A), CA04-4303(wex S82V), CA04-4303(wex S82L), and CA04-4303(wex S82I), respectively.

To confirm the amount of tryptophan production in the CA04-4303(pCL1920), CA04-4306, CA04-4303(wex S82A), CA04-4303(wex S82V), CA04-4303(wex S82L), and CA04-4303(wex S82I) strains, these strains were cultured by the same method in Example 12. After completion of the culture, the amount of L-tryptophan production in each strain was measured by HPLC.

TABLE 30

Confirmation of amount of L-tryptophan production in *E. coli*-derived L-tryptophan-producing strain (CA04-4303(pCL1920)), strain (CA04-4306) in which an L-tryptophan-exporting gene (wex) is expressed, and mutant strains (CA04-4303(wex S82A), CA04-4303(wex S82V), CA04-4303(wex S82L), and CA04-4303(wex S82I)), in which the amino acid at position 82 of the Wex amino acid sequence is respectively mutated

| Strain | Amount of Tryptophan Production (g/L) | Tryptophan Yield (g/g glc, %) | Yield Improvement Compared to Wild-type Wex (Δ, % p) |
|---|---|---|---|
| CA04-4303(pCL1920) | 1.4 | 2.0 | — |
| CA04-4306 | 2.1 | 3.0 | — |
| CA04-4303(wex S82A) | 2.9 | 4.2 | 1.2 |
| CA04-4303(wex S82V) | 3.1 | 4.4 | 1.4 |
| CA04-4303(wex S82L) | 2.4 | 3.4 | 0.4 |
| CA04-4303(wex S82I) | 2.2 | 3.2 | 0.2 |

As shown in the results of Table 30, all of the four kinds of mutants, in which the amino add at position 82 of the Wex amino add sequence is respectively substituted with a different hydrophobic amino acid, showed an improvement in fermentation yield by 0.2% p to 1.4% p, compared to the CA04-4306 strain, to which the wild-type Wex is introduced. Unlike the L-tryptophan-producing strain of *Corynebacterium glutamicum*, the *E. coli* strain with a wex S82V mutation showed the greatest improvement in L-tryptophan fermentation yield, and these results indicate that the substitution of the serine at position 82 of the Wex amino add sequence with a different hydrophobic amino add can significantly increase the activity of L-tryptophan-exporting ability of the Wex in a microorganism of the genus *Escherichia* as well as in a microorganism of the genus *Corynebacterium.*

EXAMPLE 23

Substitution of the Amino Acid at Position 83 of Wex Sequence (Isoleucine) with Hydrophobic Amino Acid in Microorganism of the Genus *Escherichia*

An attempt was made to confirm the improved effectiveness of exporting L-tryptophan through the substitution of the amino add at position 83 (i.e., isoleucine) in the amino add sequence of the Wex membrane protein with a different hydrophobic amino add in a microorganism of the genus *Escherichia*. Site-directed mutagenesis was performed using the pCL1920-PyccA-wex as a template by the same method as in Example 19 so as to generate mutations into three kinds of hydrophobic amino adds other than isoleucine.

In addition, the amino add at position 83 (i.e., isoleucine) of the Wex amino add sequence was substituted with each of the different hydrophobic amino adds (i.e., alanine (A) (SEQ ID NO: 122, SEQ ID NO: 145), valine (V) (SEQ ID NO: 123, SEQ ID NO: 146), and leucine (L) (SEQ ID NO: 124, SEQ ID NO: 147)) using the same method as in Example 19. The mutagenic primer sets and the mutation forms used to obtain the mutant pCL1920-PyccA-wex plasmids are the same as shown in Table 31 below.

TABLE 31

Mutagenic primer sets for preparation of mutant plasmids, in which the amino acid at position 83 of the Wex amino acid sequence is respectively mutated, for expression in a microorganism of the genus *Escherichia*

| Mutant Wex Plasmid | SEQ ID NO | Nucleotide Sequence |
|---|---|---|
| pCL1920-PyccA-wex I83A | 125 | GAACTCTGCCTGTCGCTCTCC**GCA**GGTTATGCCAATACAGGCAGG |
| | 126 | CCTGCCTGTATTGGCATAACC**TGC**GGAGAGCGACAGGCAGAGTTC |
| pCL1920-PyccA-wex I83V | 127 | GAACTCTGCCTGTCGCTCTCC**GTG**GGTTATGCCAATACAGGCAGG |
| | 128 | CCTGCCTGTATTGGCATAACC**CAC**GGAGAGCGACAGGCAGAGTTC |
| pCL1920-PyccA-wex I83L | 129 | GAACTCTGCCTGTCGCTCTCC**CTG**GGTTATGCCAATACAGGCAGG |
| | 130 | CCTGCCTGTATTGGCATAACC**CAG**GGAGAGCGACAGGCAGAGTTC |

The pCL1920-PyccA-wex I83A, pCL1920-PyccA-wex I83V, and pCL1920-PyccA-wex I83L vectors prepared as shown in Table 31 were each transformed by electroporation into the CA04-4303 strain, and thereby, three kinds of strains where each of the mutant wex genes that differ from one another in the amino add at position 83 is introduced were obtained. The obtained mutant strains were named as CA04-4303(wex I83A), CA04-4303(wex I83V), and CA04-4303 (wex I83L), respectively.

To confirm the amount of tryptophan production in the CA04-4303(pCL1920), CA04-4306, CA04-4303(wex I83A), CA04-4303(wex I83V), and CA04-4303(wex I83L) strains, these strains were cultured by the same method in Example 12. After completion of the culture, the amount of L-tryptophan production in each strain was measured by HPLC.

TABLE 32

Confirmation of amount of L-tryptophan production in *E. coli*-derived L-tryptophan-producing strain (CA04-4303(pCL1920)), strain (CA04-4306) in which an L-tryptophan-exporting gene (wex) is expressed, and mutant strains (CA04-4303(wex I83A), CA04-4303(wex I83V), and CA04-4303(wex I83L)), in which the amino acid at position 83 of the Wex amino acid sequence is respectively mutated

| Strain | Amount of Tryptophan Production (g/L) | Tryptophan Yield (g/g glc, %) | Yield Improvement Compared to Wild-type Wex (Δ, % p) |
|---|---|---|---|
| CA04-4303(pCL1920) | 1.4 | 2.0 | — |
| CA04-4306 | 2.1 | 3.0 | — |
| CA04-4303(wex I83A) | 2.2 | 3.2 | 0.2 |
| CA04-4303(wex I83V) | 2.3 | 3.3 | 0.3 |
| CA04-4303(wex I83L) | 2.6 | 3.7 | 0.7 |

As shown in the results of Table 32, all of the three kinds of mutant strains, in which the amino acid at position 83 of the Wex amino acid sequence is respectively substituted with a different hydrophobic amino add, showed an improvement in fermentation yield by 0.2% p to 0.7% p, compared to the CA04-4306 strain, to which the wild-type Wex is introduced. In particular, as in the L-tryptophan-producing strain of *Corynebacterium glutamicum*, the *E. coli* strain with a wex I83L mutation also showed the greatest improvement in L-tryptophan fermentation yield, and these results indicate that the substitution of the isoleucine at position 83 of the Wex amino acid sequence with a different hydrophobic amino add can significantly increase the activity of L-tryptophan-exporting ability of the Wex in a microorganism of the genus *Escherichia* as well as in a microorganism of the genus *Corynebacterium.*

From the foregoing, those skilled in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. The scope of the present disclosure should be construed as including the meaning and scope of the following claims and all changed or modified forms derived from the equivalent concepts thereof, rather than the detailed description above.

The invention claimed is:

1. A protein variant having L-tryptophan-exporting activity and comprising an amino acid sequence having at least 80% sequence identity to the amino acid sequence of SEQ ID NO: 1, wherein the protein variant comprises an amino acid substitution at a position corresponding to positions 79 to 83 of the amino acid sequence of SEQ ID NO: 1, wherein the substitution is with an amino acid selected from the group consisting of glycine, methionine, alanine, valine, leucine, and isoleucine.

2. The protein variant according to claim 1, wherein the amino acid sequence of the protein variant has at least 90% sequence identity to the amino acid sequence of SEQID NO: 1.

3. The protein variant according to claim 1, wherein the substitution is with an amino acid selected from the group consisting of glycine, alanine, valine, leucine, and isoleucine.

4. The protein variant according to claim 1, wherein the substitution is with an amino acid selected from the group consisting of alanine, valine, leucine, and isoleucine.

5. The protein variant according to claim 1, wherein the protein variant comprises any one amino acid sequence selected from the group consisting of SEQ ID NOS: 131 to 147.

6. A polynucleotide comprising a nucleotide sequence encoding the protein variant of claim 1.

7. A vector comprising the polynucleotide of claim 6.

8. An L-tryptophan-producing microorganism which expresses the protein variant of claim 1.

9. The microorganism according to claim 8, wherein the microorganism belongs to the genus *Corynebacterium* or the genus *Escherichia*.

10. A method for producing L-tryptophan, comprising:

culturing the microorganism of claim 8 in a culture medium to produce L-tryptophan; and recovering the L-tryptophan from the culture medium or the cultured microorganism.

* * * * *